(12) United States Patent
Sorelle et al.

(10) Patent No.: US 12,377,635 B2
(45) Date of Patent: Aug. 5, 2025

(54) FLOW CELL SYSTEMS AND METHODS

(71) Applicant: Nautilus Subsidiary, Inc., Seattle, WA (US)

(72) Inventors: Elliott Sorelle, Redwood City, CA (US); Pierre Indermuhle, Berkeley, CA (US); Parag Mallick, San Mateo, CA (US)

(73) Assignee: Nautilus Subsidiary, Inc., Seattle, WA (US)

( * ) Notice: Subject to any disclaimer, the term of this patent is extended or adjusted under 35 U.S.C. 154(b) by 297 days.

(21) Appl. No.: 17/772,484

(22) PCT Filed: Oct. 30, 2020

(86) PCT No.: PCT/US2020/058416
§ 371 (c)(1),
(2) Date: Apr. 27, 2022

(87) PCT Pub. No.: WO2021/087402
PCT Pub. Date: May 6, 2021

(65) Prior Publication Data
US 2022/0379582 A1    Dec. 1, 2022

Related U.S. Application Data

(60) Provisional application No. 62/928,025, filed on Oct. 30, 2019.

(51) Int. Cl.
*B32B 7/10* (2006.01)
*B01L 3/00* (2006.01)
(Continued)

(52) U.S. Cl.
CPC .......... *B32B 7/10* (2013.01); *B01L 3/502707* (2013.01); *B01L 3/502761* (2013.01);
(Continued)

(58) Field of Classification Search
CPC ......... C03C 27/00; C03C 27/06; B32B 17/06; B32B 37/10; B32B 37/18
See application file for complete search history.

(56) References Cited

U.S. PATENT DOCUMENTS

| 5,445,934 A | 8/1995 | Fodor et al. |
| 6,737,236 B1 | 5/2004 | Pieken et al. |

(Continued)

FOREIGN PATENT DOCUMENTS

| CN | 104627953 B | 6/2016 |
| WO | WO-2005065814 A1 | 7/2005 |

(Continued)

OTHER PUBLICATIONS

Zhang, M. et al. Glass wafers bonding via Diels-Alder reaction at mild temperature. Sensors and Actuators A: Physical, 2008, vol. 141, Issue 1, pp. 213-216. (Year: 2008).*

(Continued)

*Primary Examiner* — Carson Gross
(74) *Attorney, Agent, or Firm* — Morgan, Lewis & Bockius LLP

(57) ABSTRACT

Systems and methods for flow cells are provided. Flow cells may encompass a range of fluidic devices for various applications ranging from microfluidic systems to bulk phase flow systems. Flow cells may comprise one or more components for passive or active fluid transfer. Descriptions are provided for advantageous methods of fabricating flow cells for particular applications such as biological assays. Provided is a composition, comprising a first substrate comprising a first covalently-bound ligand; and a second substrate comprising a second covalently-bound ligand; wherein the first covalently-bound ligand and the second covalently-bound ligand are covalently bonded to form a heterocyclic compound. Also provided is a flow cell device, comprising: a first substrate comprising a microfabricated (Continued)

surface; and a second substrate comprising a non-patterned surface; wherein the first substrate is joined to the second substrate to form an enclosure; and wherein the microfabricated surface comprises at least one chamber, wherein the chamber comprises a microarray of active sites with specific functionalization separated by an optically resolvable distance and a functionalized surface comprising a passivating group or a blocking group; and wherein each active site of the microarray of active sites comprises a capture agent.

16 Claims, 32 Drawing Sheets

(51) Int. Cl.
- *B32B 9/04* (2006.01)
- *B32B 17/06* (2006.01)
- *B32B 37/10* (2006.01)
- *B32B 37/18* (2006.01)
- *C03C 27/06* (2006.01)

(52) U.S. Cl.
CPC ............... *B32B 9/04* (2013.01); *B32B 17/06* (2013.01); *B32B 37/10* (2013.01); *B32B 37/18* (2013.01); *C03C 27/06* (2013.01); *B01L 2200/0647* (2013.01); *B01L 2200/12* (2013.01); *B32B 2250/02* (2013.01); *B32B 2255/20* (2013.01); *B32B 2255/24* (2013.01); *B32B 2255/26* (2013.01); *B32B 2309/027* (2013.01); *B32B 2313/00* (2013.01); *B32B 2315/08* (2013.01)

(56) References Cited

U.S. PATENT DOCUMENTS

| | | |
|---|---|---|
| 7,252,954 B2 | 8/2007 | Wang et al. |
| 7,259,258 B2 | 8/2007 | Kozlov et al. |
| 7,375,234 B2 | 5/2008 | Sharpless et al. |
| 7,427,678 B2 | 9/2008 | Pieken et al. |
| 7,763,736 B2 | 7/2010 | Sharpless et al. |
| 9,528,984 B2 | 12/2016 | Mitra |
| 9,880,175 B2 | 1/2018 | Mitra |
| 10,175,248 B2 | 1/2019 | Mitra |
| 10,473,654 B1 | 11/2019 | Mallick |
| 10,571,473 B2 | 2/2020 | Mitra |
| 10,829,816 B2 | 11/2020 | Staker et al. |
| 11,203,612 B2 | 12/2021 | Gremyachinskiy et al. |
| 11,282,585 B2 | 3/2022 | Patel et al. |
| 2015/0330974 A1 | 11/2015 | Staker et al. |
| 2020/0082914 A1 | 3/2020 | Patel et al. |
| 2020/0090785 A1 | 3/2020 | Patel et al. |
| 2020/0232994 A1 | 7/2020 | Mitra |
| 2021/0239705 A1 | 8/2021 | Mallick |
| 2021/0355483 A1 | 11/2021 | Chee et al. |

FOREIGN PATENT DOCUMENTS

| | | |
|---|---|---|
| WO | WO-2014078855 A1 | 5/2014 |
| WO | WO-2019195633 A1 | 10/2019 |
| WO | WO-2020223368 A1 | 11/2020 |

OTHER PUBLICATIONS

Click! That's how modern chemistry bonds nanoparticles to a substrate. 2015. Institute of Physical Chemistry of the Polish Academy of Sciences (Year: 2015).*

Saharil, F. et al. Biocompatible "click" wafer bonding for microfluidic devices. Lab chip, 2012, 12, 3032-3035. (Year: 2012).*

Bhairamadgi, Nagendra S. et al. Efficient functionalization of oxide-free silicon(111) surfaces: thiol-yne versus thiol-ene click chemistry. Langmuir : the ACS journal of surfaces and colloids 29 14 (2013): 4535-42.

Bocking, Till et al., Thiol-Terminated Monolayers on Oxide-Free Si: Assembly of Semiconductor-Alkyl-S-Metal Junctions. Langmuir vol. 23,6 (2007): 3236-41.

Kim, M.K., et al. Biological Functionalization of the Amine-Terminated Si(100) Surface by Glycine. Surf. Sci., 604 (2010).

Sieval, A.B., et al. Amino-Terminated Organic Monolayers on Hydrogen-Terminated Silicon Surfaces. Langmuir, 17 (2001).

Veerbeek, J. and Huskens, J. Applications of Monolayer-Functionalized H-Terminated Silicon Surfaces: A Review. Small Methods, 1 (2017).

Yu, W.H., et al. Controlled Grafting of Well-Defined Epoxide Polymers on Hydrogen-Terminated Silicon Substrates by Surface-Initiated ATRP at Ambient Temperature. Langmuir, 20 (2004).

Zhu, Zhen et al. A Versatile Bonding Method for PDMS and SU-8 and Its Application Towards a Multifunctional Microfluidic Device. Micromachines vol. 7, 230 (2016).

Fodor, et al. Light-Directed, Spatially Addressable Parallel Chemical Synthesis. Science vol. 251 (1991): 767-773.

\* cited by examiner a)

b)

c)

d)

e)

a)

b)

c)

d)

e)

a)

b)

c)

d)

e)

a)

b)

c)

d)

e)

Day 0

Day 7

Day 49

Day 444

Day 0

Day 7

Day 14

Day 422

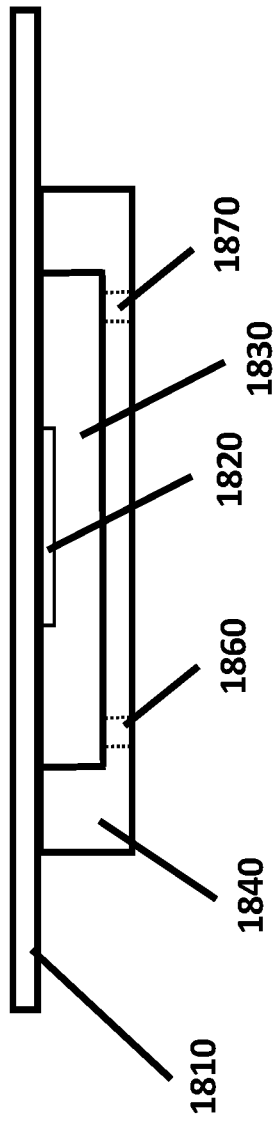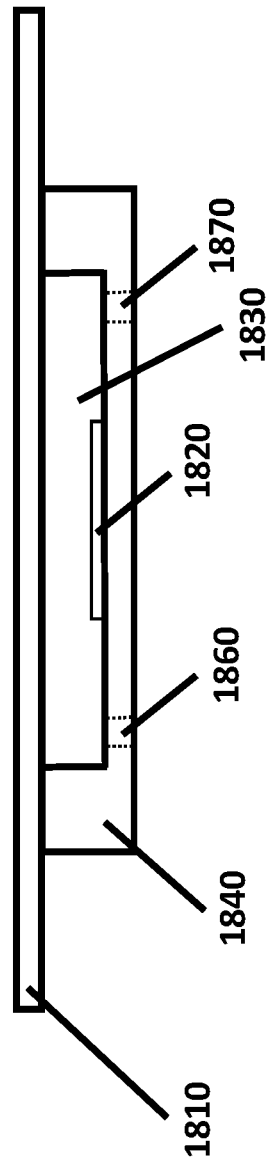

FLOW CELL SYSTEMS AND METHODS

CROSS REFERENCE

This application claims the benefit of U.S. Provisional Patent Application No. 62/928,025, filed on Oct. 30, 2019, which is incorporated herein in its entirety by reference.

BACKGROUND

Flow cells encompass a range of devices for fluidic handling, processing, control and assay. Flow cell devices may include microfluidic devices. Flow cell devices may be utilized for various chemical or biological assays, including single-molecule detection techniques. Flow cells may be fabricated from one or more components. Additionally, methods of joining those components may be dictated by the nature of the fluid transfer process to be performed.

SUMMARY

Characterization and quantitation of heterogeneous polypeptide samples is often hindered by the co-existence of proteins and/or peptides in widely varying quantities. For example, the signal from a low-copy number protein may be drowned out by the signal from a high-copy number protein in a quantitative characterization assay. Accuracy of a polypeptide characterization assay that is performed at a proteomic level (i.e. tens of thousands of unique protein species) can benefit from a combination of high-sensitivity analysis techniques and high-confidence prediction techniques.

The systems and methods described herein may be configured to achieve high-confidence characterization of polypeptides through the overlay or combination of data to narrow or refine characterizing predictions. Typical polypeptide detection methods, such as enzyme linked immunosorbent assay (ELISA), achieve high-confidence characterization of an individual polypeptide in a sample by exploiting very high specificity detection of the polypeptide in a given sample while ignoring all other polypeptides in the sample. In contrast, the systems and methods described herein can be configured to include multiple lower specificity detection assays that are performed on a sample such that the individual assays may detect multiple polypeptides while not necessarily distinguish one of the detected polypeptides from another. However, using compositions and methods set forth herein, the multiple assay results can be combined to achieve high-confidence identification or characterizations of a plurality of individual polypeptides in the sample. In many embodiments, one or more of the individual assays yield ambiguous results with regard to distinguishing the identity of a subset of polypeptides that produce detectable signal; however, characterizing the signals across the multiple assays allows individual polypeptides to be individually and unambiguously identified. The resulting set of identified polypeptides can be larger than the number of polypeptides that produce signal from any of the individual assays.

In some embodiments, a method described herein may be configured analogously to the children's game "20 Questions." An objective of this game is to identify a target answer by asking a limited number of questions. An effective tactic is to ask questions on characteristics ranging from broad characteristics (e.g., "Is it a person, place, or thing?", "Is the person in this room?") to narrow characteristics (e.g., "Is the person named 'Wayne'?"). In general, it is possible to identify a target answer in the game by asking substantially fewer questions (N) than the possible number of possible answers (M), i.e. $N \ll M$. By analogy, affinity reagents may have a broad range of interactions with respect to a population of polypeptides. For example, an affinity reagent may be considered to be a 'broad-spectrum' affinity reagent due to its affinity for a single epitope that is present in a plurality of different polypeptides in a sample or due to its affinity for a plurality of different epitopes that are present in one or more polypeptides in the sample. By testing for the interaction of an affinity reagent with a polypeptide, information is acquired regardless of whether an interaction is observed. For example, a failure of an affinity reagent to bind a polypeptide is indicative of the polypeptide lacking the epitope for the affinity reagent.

In the above-described example of 20 Questions, the outcome relies upon clear articulation of queries and answers, and also relies upon accurate and reliable answers (e.g., type, size, attributes, etc.). By analogy, polypeptide characterization by the measurement of affinity reagent interactions may be more difficult when the measurements are prone to a degree of systematic or random error or uncertainty. For example, measurement accuracy of affinity reagent (e.g., antibody) interactions with binding targets (e.g. epitopes) may be affected by numerous factors such as system detection limits or sensitivity, non-specific interactions between epitopes and affinity reagents (false positives), or stochastic, time-dependent reversal of an interaction (false negatives).

In the common situation where polypeptide characterization measurements contain a degree of uncertainty, high-confidence characterization may be achieved by utilizing a probabilistic decoding approach. The overlaying or combining of binary polypeptide interaction data (e.g., affinity reagent A1, which interacts with epitope X, was not observed to interact with unknown polypeptide P, therefore, polypeptide P does not contain epitope X) may lead to improper polypeptide characterization due to the inclusion or exclusion of possible candidate states due to measurement error. By contrast, overlaying or combining probabilistic polypeptide interaction data may permit an algorithm to converge to a high-confidence prediction of polypeptide identity without excluding any candidate states. For example, if affinity reagents A1 to A6 are known to interact with a known polypeptide P1 with interaction probabilities (95%, 85%, 80%, 10%, 10%, 5%), and measurable interactions of affinity reagents A2, A5 and A6 are observed against an unknown polypeptide P, it may be concluded that polypeptide P is likely not polypeptide P1 (2 of 3 likely interactions were not observed; 2 of 3 unlikely interactions were observed). Moreover, a probability-based characterization may be assigned a degree of confidence such that a prediction for each observed polypeptide may be made when the degree of confidence rises above a threshold degree of confidence. For example, in the above observation of polypeptide P, the six described observations may not provide a high enough degree of confidence to eliminate polypeptide P1 as a possible identity, but similar trends over 20 or more affinity reagents may provide sufficient degree of confidence to eliminate P1 as a possible identity. Accordingly, polypeptide P1 can be subjected to binding reactions with a series of broad-spectrum affinity reagents, and although the observation from each binding reaction taken individually may be ambiguous with regard to identifying the polypeptide, decoding the observations from the series of binding reactions may identify polypeptide P1 with an acceptable level of confidence.

The systems, methods, and compositions of the present disclosure may be configured to permit polypeptide characterization at an individual or single-molecule level. Polypeptides to be characterized may be provided on a substrate containing unique, optically resolvable characterization sites. Such characterization sites may be spaced, arrayed, or otherwise ordered to allow individual sites to be distinguished one from another when detecting their interactions with affinity reagents. A substrate may comprise a sufficient number of unique, optically resolvable characterization sites to accommodate a plurality, majority, or all polypeptides from a sample, such as at least about $1\times10^4$, $1\times10^5$, $1\times10^6$, $1\times10^7$, $1\times10^8$, $1\times10^9$, $1\times10^{10}$, $1\times10^{11}$, $1\times10^{12}$, or more than $1\times10^{12}$ sites.

Each site may contain a known number of polypeptides that are to be characterized. In some cases, a characterization site may contain a single polypeptide molecule to be detected, identified or characterized. In other cases, a site may contain multiple polypeptide molecules, with at least one molecule to be detected. For example, the polypeptide molecule to be detected can be one subunit in a larger protein having multiple different subunits.

In some cases, detection, identification or characterization of polypeptides may utilize affinity reagents such as antibodies (or functional fragments thereof), aptamers, mini protein binders, or any other suitable binding reagent. Affinity reagents of the present disclosure may be broad-spectrum affinity reagents that possess a likelihood to interact with (e.g., bind to) more than one polypeptide in a sample. In some cases, the affinity reagents may possess a likelihood to interact with two or more unique, structurally dissimilar proteins in a sample. For example, an affinity reagent may bind with near-equal probability to a particular membrane protein and a particular cytoplasmic protein based upon a region of structural similarity. In some cases, a binding affinity reagent may possess a likelihood of binding to a particular amino acid epitope or family of epitopes regardless of the sequence context (e.g., amino acid sequence upchain and/or downchain from the epitope).

An affinity reagent of the present disclosure may be characterized such that it has an identified, determined, or assessed probability-based binding profile. An affinity reagent may have the property of binding to a first polypeptide with an identified, determined, or assessed binding probability of greater than about 50% (e.g., at least about 50%, 60%, 70%, 80%, 90%, 95%, 99%, 99.9%, 99.99%, 99.999% or greater than about 99.999%) and binding to a second structurally non-identical polypeptide with an identified, determined, or assessed binding probability of less than about 50% (e.g., no more than about 50%, 40%, 30%, 20%, 10%, 5%, 1%, 0.1%, 0.01%, 0.001% or less than about 0.001%). In a particular case, the difference in observed binding probabilities of the affinity reagent to the first and second polypeptides may be due to the presence, absence, or inaccessibility of a particular epitope or family of epitopes in either the first or second polypeptide. Probabilistic affinity reagent binding profiles may be determined or identified by in vitro measurements or in silico predictions.

The polypeptide characterization methods and systems disclosed herein may further incorporate computational decoding approaches that are optimized for the above-described affinity reagents. The decoding approaches may overlay or combine data from multiple rounds of detecting affinity reagent interaction with individual polypeptides, and can assign a degree of confidence for detection of signal from each polypeptide. For example, affinity reagent interactions can be detected for each site in an array of sites, and a degree of confidence can be assigned to detection of each signal at each site. Similarly, a degree of confidence can be assigned to a series of detection events at each site. A polypeptide may be considered identified or characterized if the degree of confidence for a prediction based upon overlayed or combined affinity agent interaction data exceeds a threshold degree of confidence. The threshold degree of confidence for a polypeptide characterization prediction may depend upon the nature of the characterization. The threshold degree of confidence may fall in a range from about 50% to about 99.999%, such as about 50%, 60%, 70%, 80%, 90%, 95%, 99%, 99.99%, or about 99.999%. In some cases, the threshold degree of confidence may be outside this range. In some cases, the computational decoding approaches may incorporate machine learning or training algorithms to update or refine the determined or identified probabilistic interaction profile for the affinity reagents or polypeptides with increased information or in ever widening contexts.

Particularly useful methods and algorithms that can be used for detecting, identifying or characterizing polypeptides in accordance with the teachings herein are set forth, for example, in U.S. Pat. No. 10,473,654; or PCT Publication No. WO 2019/236749 A2; or US Pat. App. Pub. Nos. 2020/0082914 A1 or 2020/0090785 A1, each of which is incorporated herein by reference.

Recognized herein is for fluidic devices with properties that are compatible with biological processes and assays. Fluidic devices as disclosed herein may be produced by methods that carefully control the structure and surface chemistry of the fluidic device to produce rational architectures for biological processes and assays. In some cases, methods as disclosed herein may be used to produce patterned microarrays or nanoarrays that permit the controlled localization of biomolecules to a surface of the fluidic device.

Advantageously, the methods of the present disclosure may permit the synthesis and assembly of fluidic devices with discrete, localized surface chemistries. The surface chemistries may, in some instances, limit adhesion or binding of a particular species to a surface of the fluidic device. In some instances, the surface chemistries may prevent adhesion or binding of a particular species to a surface of the fluidic device. In some embodiments, the surface chemistries may encourage binding of a particular species to a surface of the fluidic device at a location. Further, the methods of the present disclosure may permit the synthesis and assembly of fluidic devices under ambient and/or benign processing conditions (e.g., moderate temperatures, moderate pH). Ambient and/or benign processing conditions may prevent the production and/or deposition of species that are deleterious to biological processes or assays on surfaces of the fluidic device. Ambient and/or benign processing conditions may also prevent alterations of chemistries or materials that were emplaced on the flow cell components before their assembly into a finalized flow cell apparatus.

In a first aspect, described herein is a composition, comprising a first substrate comprising a first covalently-bound ligand, and a second substrate comprising a second covalently-bound ligand, where the first covalently-bound ligand and the second covalently-bound ligand are covalently bonded to form a heterocyclic compound.

In some configurations, the heterocyclic compound is formed by a bioorthongal reaction or a click reaction selected from the group consisting of metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norborene cycloaddition, oxanobornadiene cycloaddition, tetrazine ligation, and tetrazole photoclick reaction.

In some configurations, the first substrate comprises an inorganic substrate. In some configurations, the inorganic substrate comprises glass, fused silica, or silicon. In some configurations, the inorganic substrate comprises a metal or metal oxide. In some configurations, the second substrate comprises an inorganic substrate. In some configurations, the inorganic substrate comprises glass, fused silica, or silicon. In some configurations, the inorganic substrate comprises a metal or metal oxide.

In some configurations, the first covalently-bound ligand or the second covalently-bound ligand comprises a silane derivative. In some configurations, the first covalently-bound ligand or the second covalently-bound ligand comprises a phosphate or phosphonate group.

In some configurations, the first covalently-bound ligand comprises a first functional group before the click reaction, where the first functional group is selected from the group consisting of alkenes, alkynes, azides, epoxides, amines, thiols, nitrones, isonitriles, isocyanides, aziridines, activated esters, and tetrazines. In some configurations, the second covalently-bound ligand comprises a second functional group before the click reaction, where the second functional group is selected from the group consisting of alkenes, alkynes, azides, epoxides, amines, thiols, nitrones, isonitriles, isocyanides, aziridines, activated esters, and tetrazines. In some configurations, the click reaction is selected from the group consisting of dibenzocyclooctyne (DBCO)-azide, methyltetrazine (mTz)-transcyclooctylene (TCO), and epoxide-thiol. In some configurations, the first covalently-bound ligand comprises a silane derivative comprising the first functional group, where the first functional group is selected from the group consisting of DBCO, azide, mTz, NHS ester, TCO, epoxide, and thiol. In some configurations, the second covalently-bound ligand comprises a silane derivative comprising the second functional group, where the second functional group is selected from the group consisting of DBCO, azide, mTz, NHS ester, TCO, epoxide, and thiol.

In some configurations, the first covalently-bound ligand comprises a first linear organic chain. In some configurations, the second covalently-bound ligand comprises a second linear organic chain. In some configurations, the first linear organic chain comprises at least 5 atoms. In some configurations, the second linear organic chain comprises at least 5 atoms. In some configurations, the first linear organic chain or the second organic chain comprises polyethylene glycol or polyethylene oxide. In some configurations, the first organic chain is a different length than the second organic chain. In some configurations, the first covalently-bound ligand or the second covalently-bound ligand comprises a branched chain. In some configurations, the first covalently-bound ligand or the second covalently-bound ligand comprises a hydrophobic chain. In some configurations, the first covalently-bound ligand or the second covalently-bound ligand comprises a hydrophilic chain.

In some configurations, the heterocyclic compound comprises nitrogen. In some configurations, the heterocyclic compound comprises 2 or more nitrogens. In some configurations, the heterocyclic compound comprises 3 or more nitrogens.

In another aspect, described herein is a composition comprising a first substrate comprising a first covalently-bound ligand, where the first covalently-bound ligand comprises a first functional group, and a second substrate comprising a second covalently-bound ligand, where the second covalently-bound ligand comprises a second functional group, where the first covalently-bound ligand and the second covalently-bound ligand are conjugated by one or more covalent bonds formed by a bioorthogonal reaction or click reaction.

In some configurations, the bioorthogonal reaction or click reaction is selected from the group consisting of metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norborene cycloaddition, oxanobornadiene cycloaddition, tetrazine ligation, and tetrazole photoclick reaction.

In some configurations, the bioorthogonal reaction or click reaction forms a heterocyclic compound. In some configurations, the heterocyclic compound comprises 2 or more nitrogen atoms.

In some configurations, the bioorthogonal reaction or click reaction occurs in the presence of a fluid medium. In some configurations, the fluid medium is configured to facilitate the click reaction. In some configurations, the fluid medium is an aqueous fluid. In some configurations, the fluid medium has a pH of between about 6.5 to 7.5.

In another aspect, described herein is a composition comprising a first substrate comprising a first covalently-bound ligand, where the first covalently-bound ligand comprises a first functional group, and a second substrate comprising a second covalently-bound ligand, where the second covalently-bound ligand comprises a second functional group, where the first functional group and the second functional group are configured to form a covalent bond by a bioorthogonal reaction or a click reaction.

In some configurations, the first substrate comprises an inorganic substrate. In some configurations, the inorganic substrate comprises glass, fused silica, or silicon. In some configurations, the inorganic substrate comprises a metal or metal oxide. In some configurations, the second substrate comprises an inorganic substrate. In some configurations, the inorganic substrate comprises glass, fused silica, or silicon. In some configurations, the inorganic substrate comprises a metal or metal oxide. In some configurations, the first covalently-bound ligand or the second covalently-bound ligand comprises a silane derivative. In some configurations, the first covalently-bound ligand or the second covalently-bound ligand comprises a phosphate or phosphonate group.

In some configurations, the first functional group is selected from the group consisting of alkenes, alkynes, azides, epoxides, amines, thiols, nitrones, isonitriles, isocyanides, aziridines, activated esters, and tetrazines. In some configurations, the second functional group is selected from the group consisting of alkenes, alkynes, azides, epoxides, amines, thiols, nitrones, isonitriles, isocyanides, aziridines, activated esters, and tetrazines.

In some configurations, the click reaction is selected from the group consisting of metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1]cycloaddition, nucleophilic substitution, dihydroxylation, thiol-yne reaction, photoclick, nitrone dipole cycloaddition, norborene cycloaddition, oxanobornadiene cycloaddition, tetrazine ligation, and tetrazole photoclick reaction. In some configurations, the click reaction is selected from the group consisting of dibenzocyclooctyne (DBCO)-azide, methyltetrazine (mTz)-transcyclooctylene (TCO), and epoxide-thiol.

In some configurations, the first covalently-bound ligand comprises a silane derivative comprising the first functional group, where the first functional group is selected from the group consisting of DBCO, azide, mTz, NHS ester, TCO, epoxide, and thiol. In some configurations, the second covalently-bound ligand comprises a silane derivative comprising the second functional group, where the second functional group is selected from the group consisting of DBCO, azide, mTz, NHS ester, TCO, epoxide, and thiol.

In some configurations, the composition further comprises a fluid medium. In some configurations, the fluid medium is configured to facilitate the click reaction. In some configurations, the fluid medium is an aqueous fluid. In some configurations, the fluid medium has a pH of between about 6.5 to 7.5.

In some configurations, the first covalently-bound ligand comprises a first linear organic chain. In some configurations, the second covalently-bound ligand comprises a second linear organic chain. In some configurations, the first linear organic chain comprises at least 5 atoms. In some configurations, the second linear organic chain comprises at least 5 atoms. In some configurations, the first organic chain is a different length than the second organic chain. In some configurations, the first covalently-bound ligand or the second covalently-bound ligand comprises a branched chain. In some configurations, the first covalently-bound ligand or the second covalently-bound ligand comprises a hydrophobic chain. In some configurations, the first covalently-bound ligand or the second covalently-bound ligand comprises a hydrophilic chain.

In another aspect, described herein is a method of joining a first substrate to a second substrate, comprising providing a first substrate comprising a first covalently-bound ligand and a second substrate comprising a second covalently-bound ligand, contacting the first substrate to the second substrate, and joining the first substrate to the second substrate by forming a bond between the first covalently-bound ligand and the second covalently-bound ligand, where the first covalently-bound ligand comprises a first functional group and the second covalently-bound ligand comprises a second functional group, and where the first functional group and the second functional group react via a bioorthogonal reaction or a click reaction to form the bond between the first covalently-bound ligand and the second covalently-bound ligand.

In some configurations, the first substrate comprises an inorganic substrate. In some configurations, the inorganic substrate comprises glass, fused silica, or silicon. In some configurations, the inorganic substrate comprises a metal or metal oxide. In some configurations, the second substrate comprises an inorganic substrate. In some configurations, the inorganic substrate comprises glass, fused silica, or silicon. In some configurations, the inorganic substrate comprises a metal or metal oxide. In some configurations, the first covalently-bound ligand or the second covalently-bound ligand comprises a silane derivative. In some configurations, the first covalently-bound ligand or the second covalently-bound ligand comprises a phosphate or phosphonate group. In some configurations, the first functional group is selected from the group consisting of alkenes, alkynes, azides, epoxides, amines, thiols, nitrones, isonitriles, isocyanides, aziridines, activated esters, and tetrazines. In some configurations, the second functional group is selected from the group consisting of alkenes, alkynes, azides, epoxides, amines, thiols, nitrones, isonitriles, isocyanides, aziridines, activated esters, and tetrazines.

In some configurations, the click reaction is selected from the group consisting of metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1]cycloaddition, nucleophilic substitution, dihydroxylation, thiol-yne reaction, photoclick, nitrone dipole cycloaddition, norborene cycloaddition, oxanobornadiene cycloaddition, tetrazine ligation, and tetrazole photoclick reaction. In some configurations, the click reaction is selected from the group consisting of dibenzocyclooctyne (DBCO)-azide, methyltetrazine (mTz)-transcyclooctylene (TCO), and epoxide-thiol.

In some configurations, the first covalently-bound ligand comprises a silane derivative comprising the first functional group, where the first functional group is selected from the group consisting of DBCO, azide, mTz, NHS ester, TCO, epoxide, and thiol. In some configurations, the second covalently-bound ligand comprises a silane derivative comprising the second functional group, where the second functional group is selected from the group consisting of DBCO, azide, mTz, NHS ester, TCO, epoxide, and thiol.

In some configurations, the click reaction occurs in the presence of a fluid medium. In some configurations, the fluid medium is configured to facilitate the click reaction. In some configurations, the fluid medium is an aqueous fluid. In some configurations, the fluid medium has a pH of between about 6.5 to 7.5.

In some configurations, the first covalently-bound ligand comprises a first linear organic chain. In some configurations, the second covalently-bound ligand comprises a second linear organic chain. In some configurations, the first linear organic chain comprises at least 5 atoms. In some configurations, the second linear organic chain comprises at least 5 atoms. In some configurations, the first organic chain is a different length than the second organic chain. In some configurations, the first covalently-bound ligand or the second covalently-bound ligand comprises a branched chain. In some configurations, the first covalently-bound ligand or the second covalently-bound ligand comprises a hydrophobic chain. In some configurations, the first covalently-bound ligand or the second covalently-bound ligand comprises a hydrophilic chain. In some configurations, the joining occurs at a temperature of no more than about 150° C. In some configurations, the joining occurs at a temperature of no more than about 80° C. In some configurations, the joining occurs at a temperature of no more than about 30° C.

In some configurations, the joining occurs under an exerted pressure. In some configurations, the joining occurs under vacuum. In some configurations, the joining occurs in the presence of a catalyst.

In another aspect, a flow cell device is provided comprising a first substrate comprising a microfabricated surface, and a second substrate comprising a non-patterned surface, where the first substrate is joined to the second substrate to form an enclosure, and where the microfabricated surface comprises at least one chamber, where the chamber comprises a microarray of active sites with specific functionalization separated by an optically resolvable distance and a functionalized surface comprising a passivating group or a blocking group, and where each active site of the microarray of active sites comprises a capture agent.

In another aspect, a method is provided for fabricating a flow cell device, comprising providing a first substrate comprising a microfabricated surface, where the microfabricated surface comprises a first surface and a second surface, providing a second substrate comprising a non-patterned surface, joining the first substrate to the second substrate, linking a capture agent to the first surface, and linking a blocking group or passivating group to the second surface, where the first surface comprises a microarray of active sites with a specific functionalization separated by an optically resolvable distance.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

Novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 18E shows a cross-sectional schematic of a fluidic device containing a substrate configured to display a plurality of peptides, in accordance with some embodiments.

FIG. 18F shows a cross-sectional schematic of a fluidic device containing a substrate configured to display a plurality of peptides, in accordance with some embodiments.

DETAILED DESCRIPTION

Figure 1A:
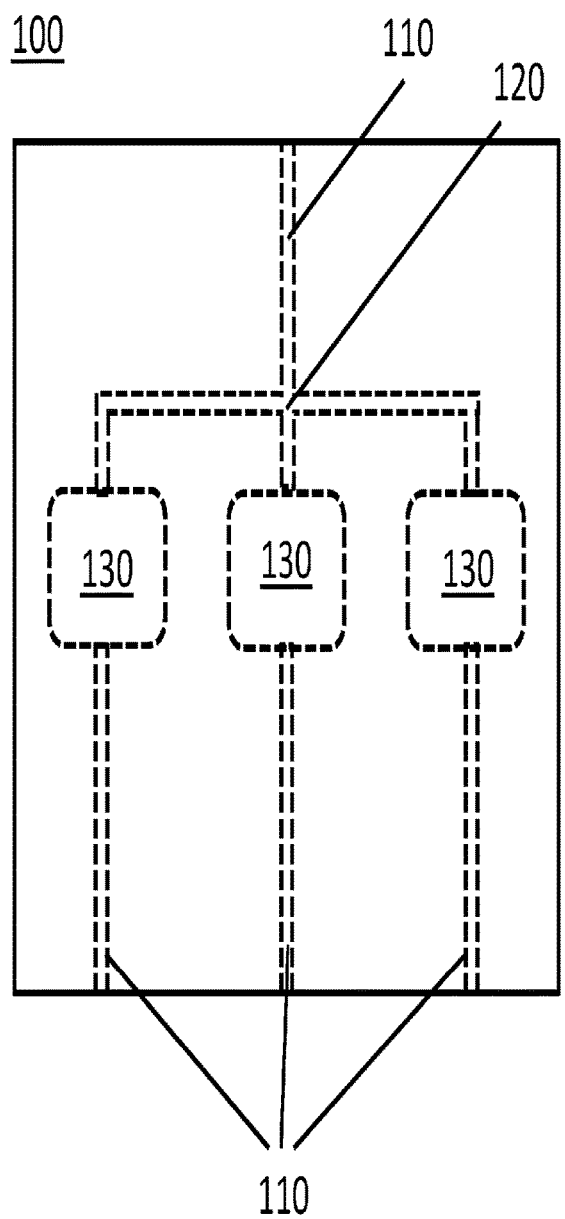
FIG. 1A shows an exemplary schematic of a top-down view of a fluidic device of the present disclosure, in accordance with some embodiments.

Recognized herein is a need for fluidic devices that are compatible with biological assays under a broad range of processing conditions. In some embodiments, fluidic devices that contain selectively patterned surface chemistries may be used to control specific chemical interactions that occur at varying regions of a given surface. In some cases, the fluidic devices may be configured to bind a plurality of biomolecules (e.g., polypeptides, nucleic acids) at individual, optically observable addresses. It may prevent biomolecule adsorption or deposition at a particular area of a substrate while encouraging the biomolecule adsorption or deposition at another area of the substrate. Additionally, it may be beneficial to utilize fabrication techniques for fluidic devices that minimize or eliminate the availability of biologically-incompatible contaminants or molecules. For example, high-temperature fabrication methods may generate surface contaminants or modify surface chemistries in a way that may affect biological assays. The fluidic devices fabricated via low-temperature processes may be used and biologically-compatible materials and chemicals may be utilized. Several configurations for the methods and devices of the present disclosure are exemplified herein with respect to their application to detection or manipulation of polypeptides and affinity reagents that bind those polypeptides; however, it will be understood by those skilled in the art that the methods and devices can be applied to the detection or manipulation of a variety of other analytes and reagents. Accordingly, the methods and devices of the present disclosure can be used to detect, synthesize or manipulate biomolecules such as nucleic acids (e.g. DNA or RNA), saccharides, lipids, and metabolites; biological cells or organelles such as nuclei, mitochondria or chloroplasts; synthetic molecules such as therapeutics or candidate therapeutics, or the like. In particular configurations a method or device of the present disclosure can omit or be devoid of one or more of the analytes or reagents set forth above or elsewhere herein.

Provided herein are embodiments of a multifunctional system for fabricating fluidic devices for various applications, including chemical and biological assays. The system may utilize a substrate with differing surface chemistries or with one or more surfaces coated in a metal or metal oxide coating to form a fluidic component. The substrate, surface chemistries and/or metal oxide may be patterned by various microfabrication techniques to create functional structures such as channels, chambers, and reservoirs on the fluidic component. After microfabrication, the fluidic component may comprise regions of metal or metal oxide and/or regions of exposed substrate, thereby permitting specific surface chemistries to be applied to the differing regions. A fluidic component may include multiple regions containing one or more specific surface chemistries. Specific surface chemistries may be utilized for differing specific applications. For example, a first region may be modified with a binding agent that permits the capture of biomolecules in that region, while a second region may be modified with a surface adhesive that permits the joining of other fluidic device components. In some configurations, a single region may have more than one surface chemistry co-localized to permit multiple forms of surface modification to be formed. For example, a single surface region of a fluidic component may have binding agents and blocking molecules co-localized to permit highly-controlled binding at surface locations containing a binding agent.

Provided herein are systems and methods for chemically modifying surfaces within a fluidic device to encourage specific surface interactions at the device surface. In some configurations, a surface may be modified with a passivating agent or a blocking molecule to prevent the adhesion, adsorption, or deposition of biomolecules or reagents at the surface. In other configurations, a surface within a fluidic device may be modified with a binding agent or reactive ligand that encourages the adhesion, adsorption, deposition or bonding of biomolecules or reagents at the surface. Passivating agents, blocking molecules, binding agents, and reactive ligands may be attached to a surface of a fluidic device by a surface-bound ligand. In some configurations, a surface of a fluidic device may comprise multiple surface-bound ligands of differing chemical compositions, thereby permitting control over the location and extent of surface alteration.

Provided herein are systems and methods for adhering components of a fluidic device. In some configurations, a bond may be formed between a first substrate comprising a surface-bound ligand and a second substrate comprising a surface bound ligand. A bond may be formed between two surface-bound ligands by a chemical mechanism such as a nucleophilic substitution reaction. Also provided herein are systems and methods for adhering components of a fluidic device when the components have a characterized surface roughness or camber. In some configurations, joined surfaces may be modified with reactive ligands of sufficient length to overcome the average surface roughness or camber. In other configurations, a chemical cross-linker may be utilized to increase adhesion in areas of limited bonding due to surface roughness or camber.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

As used herein, the term "functional group" generally refers to a portion of a molecule with a recognizable or classified chemical structure. A functional group may comprise one atom (e.g., —F) or more than one atom (e.g., —COOH). A functional group may be organic or inorganic. A functional group may comprise one or more electrically charged species such as cations, carbocations, anions, carbanions, or radicals. Exemplary functional groups may include, without limitation, alkyl, alkenyl, alkynyl, phenyl, halide, hydroxyl, carbonyl, aldehyde, acyl halide, ester, carboxylate, carboxyl, carboalkoxy, methoxy, hydroperoxy, ether, hemiacetal, hemiketal, acetal, ketal, orthoester, epoxide, carboxylic anhydride, carboxamide, amine, ketimine, aldimine, imide, azide, azo, cyanate, isocyanate, nitrate, nitrile, isonitrile, nitrosoxy, nitro, nitroso, oxime, pyridyl, carbamate, sulfhydryl, sulfide, disulfide, sulfinyl, sulfonyl, sulfinom, sulfo, thiocyanate, isothiocyanate, carbonothioyl, thioester, thionoester, phosphino, phosphono, phosphonate, phosphate, borono, boronate, and borinate.

As used herein, the term "silane" generally refers to a broad class of tetravalent silicon compounds, including $SiH_4$ as well as substituted compounds. A silane may comprise up to four hydrogen atoms bonded to the central silicon atom. A silane may be substituted with one or more functional groups, e.g., APTES (3-aminopropyltriethoxysilane). Silanes may include compounds with a chain of two or more bonded tetravalent silicon atoms that are saturated with hydrogens or substituted functional groups. A silane chain with multiple silicon atoms may include substituted or bridging atoms between silicon atoms (e.g., $H_3Si$—O—$SiH_3$)

As used herein, the term "phosphate" generally refers to a phosphorus atom bonded to four oxygen atoms. A phosphate molecule may comprise a salt (e.g., sodium phosphate) or an acid (e.g. phosphoric acid). A phosphate molecule may comprise a functional group in a larger molecule.

As used herein, the term "phosphonate" generally refers to a functional group with the structure —$PO(OH)_2$ or —$PO(OR)_2$, where R may comprise a functional group covalently linked to the oxygen atom. A phosphonate group may be covalently bound to an organic molecule. Phosphonates may include bisphosphonates and thiophosphonates.

As used herein, the terms "surface functionalization" or "ligand" generally refer to a permanent or semi-permanent surface-linked molecule. A molecule comprising a ligand may be linked to a surface by covalent bonding, ionic bonding, coordinate bonding, physisorption or chemisorption. A ligand may be considered permanent if it is linked to the surface via a covalent bond or is otherwise stable over a wide range of environmental or chemical conditions. A ligand may be considered semi-permanent if it may be disrupted or removed, partially or in whole, by a specific process or method. An exemplary ligand may comprise an APTES molecule bonded to a silica substrate.

As used herein, the term "cross-linking molecule" generally refers to a molecule, functional group, or ligand that links together two molecular chains or two portions of a molecular chain. A cross-linking molecule may link together two molecular chains or two portions of a molecular chain via covalent or ionic bonding. A cross-linking molecule may comprise a moiety or functional group within a first chain that forms a link with a moiety or functional group of a second chain. A cross-linking molecule may comprise a moiety or functional group within a molecule that forms a link with a moiety or functional group within the same molecule. A cross-linking molecule may comprise a separate molecule with two or more functional groups that forms a link between two separate molecules or between two separate portions of the same molecule.

As used herein, the terms "blocking molecule" or "blocking group" generally refer to a surface-bound molecule that prevents a specific interaction between a second molecule and a surface. A blocking molecule may prevent a second molecule from deposition, adsorption, absorption, reaction, diffusion, or other unwanted surface interaction. A blocking molecule may prevent a surface interaction by certain physical mechanism including, without limitation, steric repulsion, electrostatic repulsion, magnetic repulsion, hydrophobicity, and hydrophilicity. A blocking molecule may comprise a ligand, e.g., a surface-bound phosphonate. A blocking molecule may comprise a macromolecule, e.g., polyethylene glycol (PEG).

As used herein, the term "fluidic device" generally refers to a system that actively or passively contains a moving liquid or gaseous fluid medium. Fluidic devices may include devices from a broad range of length scales from macroscale to nanoscale or smaller. Fluidic devices include microfluidic devices as used herein. Fluidic devices encompass flow cell devices. A fluidic device may contain active elements for fluid transfer such as pumps, compressors, and blowers. A fluidic device may permit passive fluid transfer by mechanisms such as gravitational flow or capillary flow. A fluidic device may contain regions of hydrostatic or quiescent fluid, such as reservoirs or chambers.

As used herein, the terms "microfabricating" and "microfabrication" generally refer to processes of forming nanoscale features (i.e. a characteristic length of less than 1 µm) or microscale features (i.e. a characteristic length of less than 1 mm) on a substrate or surface. Microfabrication techniques may include, without limitation, lithography, patterning, machining, deposition techniques, forming, embossing, imprinting and extrusion. Microfabrication may entail the formation of surface features such as, without limitation, channels, tunnels, holes, wells, depressions, edges, seams, chambers, reservoirs, pillars, posts, walls, and paths.

As used herein, the term "channel" generally refers to a void space or path within a substrate or material that is primarily configured to permit the passage of fluids or other transportable materials from one portion of the substrate to another. A channel may be characterized as having a larger length than width or depth. A channel may have a particular cross-sectional profile shape, such as rectangular, square, circular, oval, or irregular. A channel can have microfluidic dimensions, for example, having a channel diameter of at most about 500 micrometers, 100 micrometers, 1 micrometer, 500 nanometers or 100 nanometers. Alternatively, a channel can have microfluidic dimensions, for example, having a diameter greater than 500 micrometers.

As used herein, the term "chamber" generally refers to a void space or opening within a substrate or material that is primarily configured to hold fluids or other transportable materials for processes or methods other than fluid transport. A chamber may comprise a reservoir for fluid storage. A chamber may comprise a functional region for performing processes such as chemical reactions, assays, or detections, or characterizations.

As used herein, the terms "solid support" or "substrate" refer to a rigid material that is insoluble in aqueous liquid. The material can be non-porous or porous. The material can optionally be capable of taking up a liquid (e.g. due to porosity) but will typically be sufficiently rigid that the material does not swell substantially when taking up the liquid and does not contract substantially when the liquid is removed by drying. A nonporous solid support or substrate is generally impermeable to liquids or gases. Exemplary solid supports and materials include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor™, silica or silica-based materials including silicon and modified silicon, carbon, metals, inorganic glasses, optical fiber bundles, and polymers. A solid support or substrate can optionally be macroscopic in size or microscopic in size. A solid support or substrate that is too small to be resolved by a light microscope need not be used for particular embodiments of the present disclosure.

As used herein, the term "bioorthogonal reaction" refers to a chemical reaction that can occur within a biological system (in vitro and/or in vivo) without interfering with the native biological processes, functions, or activities of the biological system. A bioorthogonal reaction may include a click reaction. Bioorthogonal reactions may include Staudinger ligation, copper-free click reactions, nitrone dipole cycloaddition, norborene cycloaddition, oxanorbornadiene cycloaddition, tetrazine ligation, [4+1] cycloaddition, tetrazole photoclick reactions, and quadricyclane ligation. As used herein, the term "click reaction" refers to single-step, thermodynamically-favorable conjugation reaction utilizing biocompatible reagents. A click reaction may utilize no toxic or biologically incompatible reagents (e.g., acids, bases, heavy metals) or generate no toxic or biologically incompatible byproducts. A click reaction may utilize an aqueous solvent or buffer (e.g., phosphate buffer solution, Tris buffer, saline buffer, MOPS, etc.). A click reaction may be thermodynamically favorable if it has a negative Gibbs free energy of reaction, for example a Gibbs free energy of reaction of less than about −5 kiloJoules/mole (kJ/mol), −10 kJ/mol, −25 kJ/mol, −50 kJ/mol, −100 kJ/mol, −200 kJ/mol, −300 kJ/mol, −400 kJ/mol, or less than −500 kJ/mol. Exemplary bioorthogonal and click reactions are described in detail in WO 2019/195633A1, which is herein incorporated by reference in its entirety.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered.

A fluidic device may include a modular assembly for fluidic operations. A fluidic device may comprise at least one channel for passage of a fluid into the fluidic device or out of the fluidic device. In some configurations, a fluidic device may utilize a particular channel as both a fluid inlet and outlet. A fluidic device may comprise reservoirs for the temporary or permanent storage of fluids. A fluidic device may comprise other features such as pumps, heaters, valves, drains, plugs, and caps. A fluidic device may include ports or fittings that permit the connection of fluid lines to the fluidic device. Ports may be threaded to permit the manual connection of a fitting or connection. Fittings may include compression fittings and quick connect fittings. A fluidic device may include fixtures for connecting the fluidic device to a larger system. A fluidic device may include electronic components such as sensors, heating elements, wires, electrical ports, and microprocessors.

A fluidic device may comprise a cartridge that can be placed into a system that includes fluid delivery systems and detection or analysis systems in operative connectivity with the fluidic device. A fluidic device may connect to a larger system using eyelets, grommets, pegs, rods, snaps, bolts, screws, clamps, straps, or other fixtures for securement. A fluidic device may be intended for liquid-phase fluids, gas-phase fluids, or multiphase flows, such as gas bubbles, emulsions, or slurry flows. A fluidic device may include macrofluidic components or microfluidic components. A fluidic device may include both microfluidic and macrofluidic components. A fluidic device may be designed for operation in a laminar flow regime, a turbulent flow regime, or a combination of flow regimes. A fluidic device may be designed to be a permanent fixture in a fluid transfer system or be a removable component. A fluidic device may be a disposable cartridge. A fluidic device may be designed for multiple uses or cyclical uses.

Figure 1B:
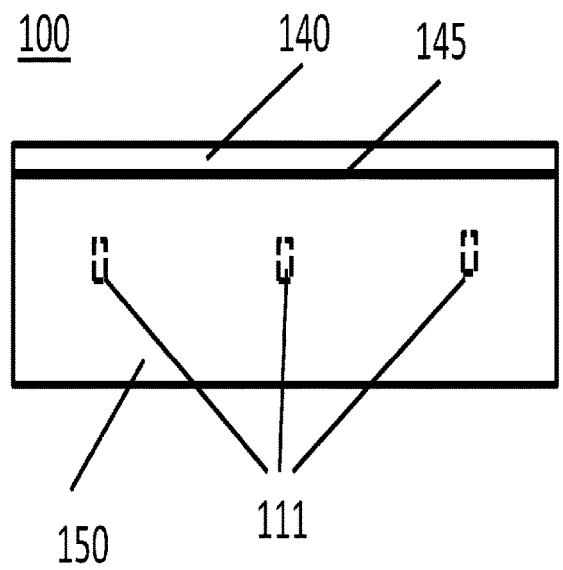
FIG. 1B shows an exemplary schematic of a side view of a fluidic device of the present disclosure, in accordance with some embodiments.

FIG. 1A presents a schematic view of an exemplary fluidic device 100. The fluidic device 100 may comprise one or more flow channels 110. Flow channels 110 may merge or split at a junction 120. Flow channels 110 may serve various functions in the fluidic device 100 including, but not limited to, fluid transfer, separation processes, heat transfer, reactive processes, fluid analysis, and particle detection and/or analysis. A fluidic device 100 may also comprise one or more chambers or reservoirs 130. Chamber or reservoirs 130 may serve various function in the fluidic device 100 including, but not limited to, fluid storage, flow quiescence, fluid mixing, separation processes, heat transfer, reactive processes, fluid analysis, and detection and/or analysis. FIG. 1B presents a side-view of the exemplary fluidic device 100 depicted in FIG. 1A. The fluidic 100 comprises an first fluidic component 140 that is connected to a second component 150 by a bonded interface 145. Fluid ports 111 provide paths for fluid flow into and out of the flow channels 110 of the fluidic device. In some configurations, the ports or channels 110 may be located at the surface of a fluidic device component such that the joining of a second fluidic component encloses the port or channel. In the present disclosure, fluidic structures and other functional areas of the fluidic device may be created on some or all of the fluidic components that comprise the fluidic device.

Fluidic devices of the present disclosure may be designed for fluid transfer and control at various length scales, including macrofluidic and microfluidic length scales. A fluidic device may be a particular shape including square, rectangular, oval, or circular. A fluidic device may be designed to be a fixed or removable piece of a larger fluid transfer system, with a shape, size, or footprint that is customized to the needs of the larger fluid transfer system. A fluidic device may have a particular length, width, or height depending upon the application of the fluidic. A fluidic device may have a length, width, or height of about 1 centimeter (cm), 10 cm, 15 cm, 20 cm, 30 cm, 40 cm, 50, or about 100 cm. A fluidic device may have a length, width, or height of at least about 1 cm, 10 cm, 15 cm, 20 cm, 30 cm, 40 cm, 50 cm, or about 100 cm or more. A fluidic device may have a length, width, or height of no more than about 100 cm, 50 cm, 40 cm, 30 cm, 20 cm, 15 cm, 10 cm, or 1 cm or less.

Substrates

A fluidic device may be fabricated using a suitable material or combination of suitable materials. A suitable material may comprise a material with characteristics such as hydrophobicity or hydrophilicity, amphipathicity, low adhesion of particular chemical or biological species, and particular chemical, optical, electrical, or mechanical properties. In some configurations, a material may be chosen for incorporation into a fluidic device due to its compatibility with a detection technique or method. For example, a material may be selected due to its low autofluorescence characteristic if a fluorescent detection method is to be utilized. A substrate may be a solid surface to which molecules can be covalently or non-covalently attached. Non-limiting examples of solid substrates include slides, surfaces of elements of devices, membranes, flow cells, wells, chambers, and macrofluidic chambers. Solid supports used herein may be flat or curved, or can have other shapes, and can be smooth or textured. In some configurations, solid support surfaces may contain microwells. In some configurations, substrate surfaces may contain nanowells. In some configurations, solid support surfaces may contain one or more microwells in combination with one or more nanowells. Fluidic device components may be fabricated from polymers, glasses, semiconductors (e.g., silicon, germanium), ceramics, metals, minerals, or other materials. In some instances, a fluidic device may comprise components made of a glass such as borosilicate glass, fused silica, or quartz. In other instances, a fluidic device component may comprise an optical glass or a photochromatic glass. In some configurations, a glass with a high sodium or potassium content may be selected as a material for a fluidic device component. Fluidic device components may be fabricated from polymers or plastics such as polycarbonate, polyethylene, polypropylene, polyethylene terephthalate, polyvinyl chloride, polymethyl methacrylate, polydimethylsiloxane, polystyrene acrylics, latex and others. Fluidic device components may comprise metals and metal alloys such as stainless steel, gold, chromium, titanium, titanium oxide, tin oxide, zirconium oxide or aluminum. Fluidic device components may comprise carbohydrates such as dextrans or cellulose. Steel components may be integrated into fluidic devices as fittings for connections and other components such as valves and drains. In some configurations, a fluidic device may comprise two or more components with different (e.g. plastic vs. glass) or differing (e.g. borosilicate vs. quartz glass) material types. In some configurations, a fluidic device component may comprise one or more surface functionalities or surface treatments that permit or facilitate the joining of fluidic device components. Such treatments may include the deposition of materials such as plastics or metal species, or the functionalization of the surface with organic or inorganic ligands, moieties, or functional groups.

A substrate in a fluidic device may be characterized by a thickness or depth. The thickness of a substrate may be uniform or may vary over the body of the substrate. The thickness of the substrate may be altered by a fabrication, forming or machining process. In some configurations, a substrate may have a thickness of about 1 micrometer (μm), 10 μm, 50 μm, 100 μm, 250 μm, 500 μm, 750 μm, 1 millimeter (mm), 5 mm, 1 centimeter (cm), 10 cm or more. In some configurations, a substrate may have a thickness of at least about 1 micrometer (μm), 10 μm, 50 μm, 100 μm, 250 μm, 500 μm, 750 μm, 1 millimeter (mm), 5 mm, 1 centimeter (cm), 10 cm or more. Alternatively or additionally, a substrate may have a thickness of no more than about 10 cm, 1 cm, 5 mm, 1 mm, 750 μm, 500 μm, 250 μm, 100 μm, 50 μm, 10 μm, 1 μm or less.

A fluidic device substrate may comprise one or more surface coatings. A surface coating may be organic or inorganic. In some configurations, a surface coating may be deposited by a suitable deposition process, e.g., atomic layer deposition, chemical vapor deposition, chemical, liquid deposition, self-assembling monolayers. In some configurations, a surface coating may be patterned by a suitable patterning process, e.g., dry etch, wet etch, lift-off, deep UV lithography or combination thereof. A deposited surface coating may have a uniform thickness or a variable thickness over a surface of a substrate. In some configurations, a surface coating may comprise an atomic or molecular monolayer. In some configurations, a surface coating may comprise a self-assembled monolayer. In some configurations, a surface coating may comprise a metal or metal oxide layer. In some configurations, a surface coating may comprise a silane layer (e.g., ethoxy-, methoxy- or chloro-silane), a phosphonate layer, or a phosphate layer. In some configurations, a surface coating may comprise a polymer, a mineral, a ceramic, or an ink.

A surface coating on a fluidic device substrate may be characterized by a particular thickness. A surface coating may be at least about 1 Angstrom (Å), 5 Å, 1 nanometer (nm), 5 nm, 10 nm, 20 nm, 30 nm, 40 nm, 50 nm, 100 nm, 250 nm, 500 nm, 1 micrometer (μm), 5 μm, 10 μm, 50 μm, 100 μm or more. Alternatively or additionally, a surface coating may be no more than about 100 μm, 50 μm, 10 μm, 5 μm, 1 μm, 500 nm, 250 nm, 100 nm, 50 nm, 40 nm, 30 nm, 20 nm, 10 nm, 5 nm, 1 nm, 5 Å, 1 Å or less.

A fluidic device component may comprise one or more surfaces that are coated with a layer of metal or metal oxide. A metal or metal oxide layer may be further coated or functionalized with another layer or functionality that facilitates other processes such as the joining of two fluidic device components or passivating a fluidic surface. A metal or metal oxide layer may comprise a particular species depending upon the preferable chemistry. Candidate metals or metal oxides may include zirconium oxide ($ZrO_2$), hafnium (Hf), gold (Au), titanium dioxide ($TiO_2$), aluminum (Al), aluminum oxide ($Al_2O_3$) or a combination thereof.

In some configurations, the substrate may be optically opaque. In some configurations, the solid substrate may be optically clear at one or more wavelengths (e.g. wavelengths in the UV, visible or infrared regions of the radiation spectrum). In some configurations, the solid substrate may be partially optically clear, or may be optically clear in some regions. For example, a solid substrate may be optically opaque in regions that are not functionalized, and optically clear in regions that are functionalized.

Substrate Fabrication

One or more components within a fluidic device may comprise surface features or surface structures for applications such as creating flow paths, creating functional areas (e.g. for mixing fluids), creating active areas (e.g. for performing assays), performing detection or analysis methods, or other intended applications. Surface features or surface structures in a fluidic device component may be created by suitable methods including machining, cutting, depositing materials, molding, casting, and other methods. A fluidic device component may comprise surface features or surface structures fabricated by a method of micromachining, microstructuring, micropatterning, or microfabrication. Such surface structures or surface features may be intended for microfluidic devices. In some configurations, micromachining, microstructuring, micropatterning, or microfabrication may occur over a particular region of a surface on a particular fluidic device component. In some configurations, a fluidic device may comprise one or more components where one or more of the components comprise at least one region of micromachining, microstructuring, micropatterning, or microfabrication.

Micromachining, microstructuring, micropatterning, or microfabrication may occur by a suitable technique, such as material deposition techniques, material etching techniques or lithographic techniques. Deposition techniques may include methods such as physical vapor deposition, sputtering, pulsed laser deposition, ion beam deposition, electrohydrodynamic deposition, solution deposition, electroplating, spin coating, dip coating, chemical vapor deposition, atomic layer deposition, or molecular layer deposition. Etching techniques may include methods such as wet etch, dry etch, laser ablation, physical etch, chemical etch, deep UV exposure or light enhanced chemical reaction. Lithographic techniques may include microlithographic or nanolithographic techniques such as photolithography or extreme ultraviolet lithography, direct laser writing, e-beam lithography, micro- or nano-imprint.

In general, a fluidic device component may be microfabricated or micropatterned by a suitable technique. Fabrication of regions of micromachining, microstructuring, micropatterning, or microfabrication may involve multiple processing steps, including deposition of photo-patternable layers, exposure of such layers by photo-lithography, development of such layers, patterning of materials with different selectivity relative to etching techniques to create masks (e.g. amorphous silicon or poly-crystalline silicon vs glass or fused silica) or photoresists (e.g., Novolac-based i-line positive resist) etching of a substrate comprising a portion of the body of the fluidic component, and removal of masks or other surface layers. Microfabricated fluidic device components may be subsequently placed in other processing steps such as cleaning, surface passivation, and surface functionalization.

A fluidic device may comprise one or more flow channels with a characteristic dimension (e.g. a diameter, circumference, perimeter, height, or width). A flow channel in a fluidic device may have a characteristic dimension of about 1 micrometer (μm), 10 μm, 50 μm, 100 μm, 250 μm, 500 μm, 750 μm, 1 millimeter (mm), 5 mm, or about 1 cm. A flow channel in a fluidic device may have a characteristic dimension of at least about 1 μm, 10 μm, 50 μm, 100 μm, 250 μm, 500 μm, 750 μm, 1 mm, 5 mm, or about 1 cm or more. Alternatively or additionally, a flow channel in a fluidic device may have a characteristic dimension of no more than about 1 cm, 5 mm, 1 mm, 750 μm, 500 μm, 250 μm, 100 μm, 50 μm, 10 μm, or 1 μm or less. A flow channel in a fluidic device may have a cross-sectional profile with a particular shape. A flow channel may have a circular, oval, square, rectangular or other cross-sectional profile. The shape of a flow channel may be affected by the method used to fabricate the flow channel, e.g. wet acid etching. A flow channel may vary in terms of characteristic dimension or shape over its length. For example, a flow channel may expand, constrict, or include flow impediments at particular points along its length. A flow channel may be characterized by a particular cross-sectional aspect ratio. A cross-sectional aspect ratio may be defined as the ratio between the largest width and the narrowest width of a flow channel at a particular cross-section along its length. A cross-sectional aspect ratio may vary along the length of a flow channel. A flow channel may have a cross-sectional aspect ratio of about 1:1, 2:1, 3:1, 4:1, 5:1, 10:1, 25:1, 50:1, or about 100:1. A flow channel may have a cross-sectional aspect ratio of at least about 1:1, 2:1, 3:1, 4:1, 5:1, 10:1, 25:1, 50:1, or about 100:1 or more. Alternatively or additionally, a flow channel may have a cross-sectional aspect ratio of no more than about 100:1, 50:1, 25:1, 10:1, 5:1, 4:1, 3:1, 2:1, or 1:1 or less. A flow channel may have a cross-sectional profile with a particular geometry. A flow channel may have a circular, rectangular, rectangular with rounded corners, triangular, irregular, or otherwise varying cross-sectional profile. A flow channel may have a cross-sectional profile or other characteristic dimension that varies along the length of its path.

A fluidic device may comprise chambers or reservoirs. A chamber or reservoir may be used to store fluids, perform assays, perform detection or analysis methods, reduce flow velocities, sediment, separate, or mix fluids, or other possible operational functions as required for a fluidic device's intended application. A fluidic device may be characterized by a particular volume. A chamber or reservoir in a fluidic device may have a volume of about 1 microliter (μl), 10 μl, 100 μl, 500 μl, 1 milliliter (ml), 5 ml, 10 ml, 50 ml, or 100 ml. A chamber or reservoir in a fluidic device may have a volume of at least about 1 μl, 10 μl, 100 μl, 500 μl, 1 ml, 5 ml, 10 ml, 50 ml, or 100 ml or more. Alternatively or additionally, a chamber or reservoir in a fluidic device may have a volume of no more than about 100 ml, 50 ml, 10 ml, 5 ml, 1 ml, 500 μl, 100 μl, 10 μl, or 1 μl.

Figure 2:
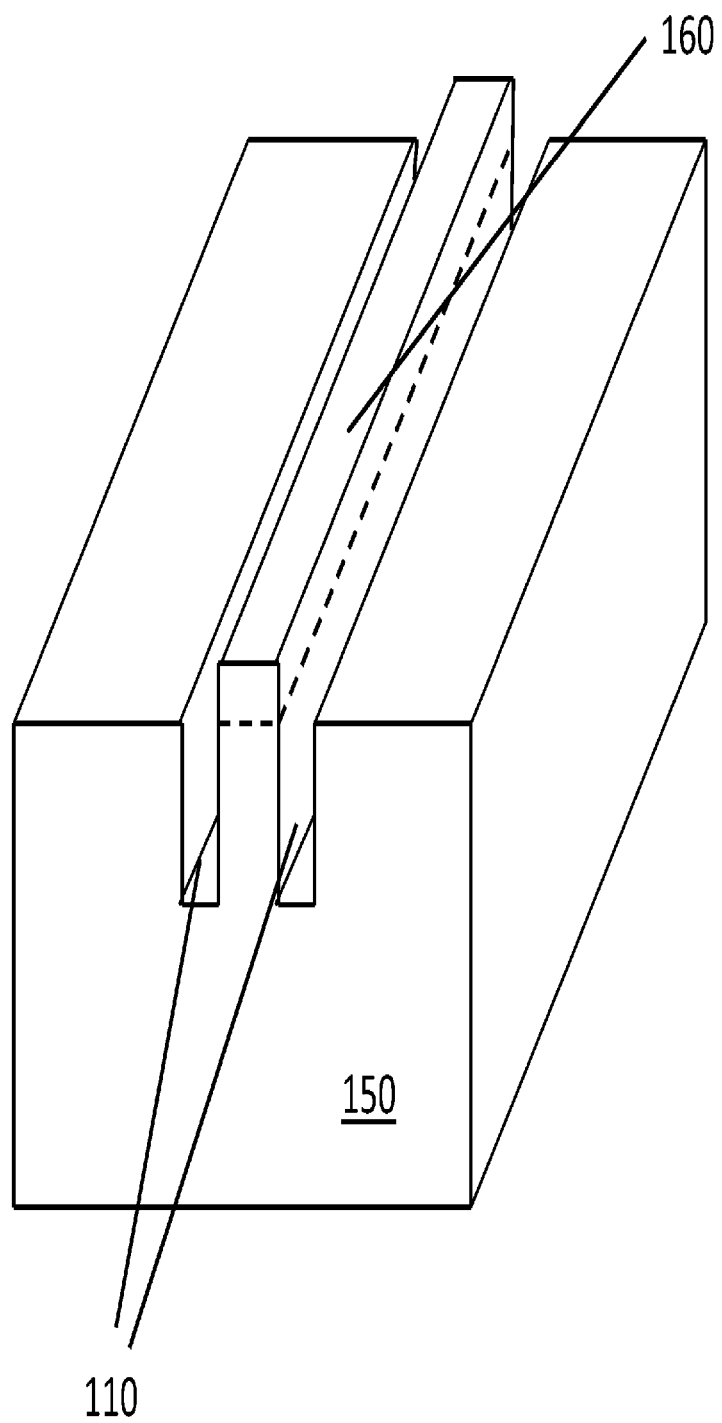
FIG. 2 depicts a schematic of a structured substrate surface containing a ridge or wall structure and multiple channels, in accordance with some embodiments.
Figure 3:
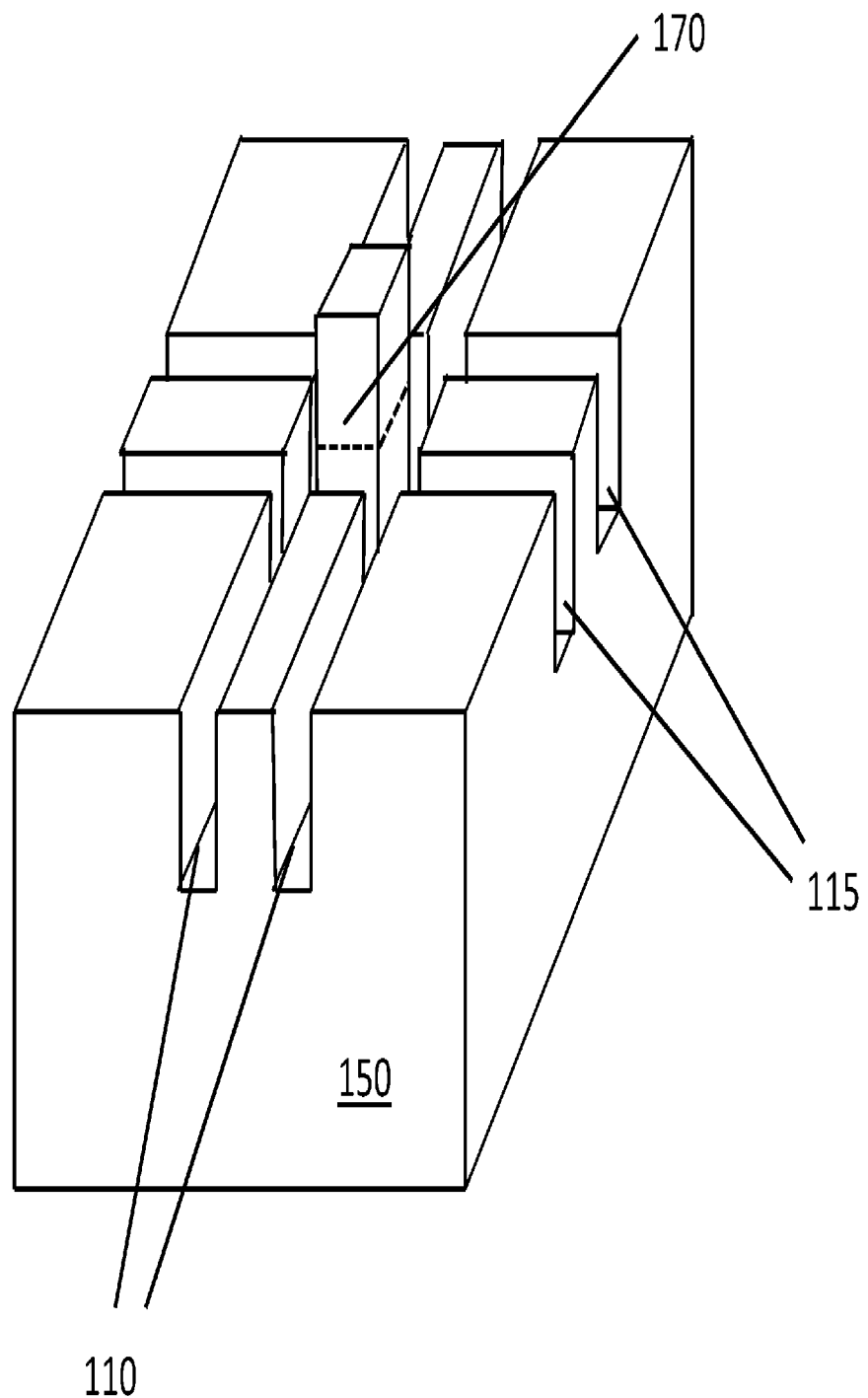
FIG. 3 illustrates a schematic of a structured substrate containing a pillar structure and multiple intersecting channels, in accordance with some embodiments.

A fluidic device component may comprise other structures that are created by micromachining, microstructuring, micropatterning, or microfabrication of a substrate. Exemplary structures may include posts, pillars, wells, holes, ridges, and walls. FIG. 2 depicts an exemplary wall structure 160 formed by a deposited and structured surface deposit (e.g., Au or $ZrO_2$) on a substrate surface 150 between two channels 110 that were also formed by a surface structuring process. FIG. 3 depicts intersecting channels 110 and 115 with a pillar structure 170 formed by a deposited and structured surface deposit (e.g., Au or $ZrO_2$) on a substrate 150. Raised pillar or ridge structures may comprise points of contact for joining fluidic device components or may serve other applications, such as providing binding surfaces for capture agent. Structures on a fluidic device may have a characteristic height, width or depth. A structure on a fluidic device component may have a height, width or depth of at least about 1 nm, 5 nm, 10 nm, 20 nm, 30 nm, 40 nm, 50 nm, 100 nm, 150 nm, 200 nm, 250 nm, 300 nm, 350 nm, 400 nm, 450 nm, 500 nm, 600 nm, 700 nm, 800 nm, 900 nm, 1 μm, 10 μm, 50 μm, 100 μm, 250 μm, 500 μm, 750 μm, 1 mm, 5 mm, or about 1 cm or more. A structure on a fluidic device component may have a height, width, or depth of no more than about 1 cm, 5 mm, 1 mm, 750 µm, 500 µm, 250 µm, 100 µm, 50 µm, 10 µm, 1 µm, 900 nm, 800 nm, 700 nm, 600 nm, 500 nm, 450 nm, 400 nm, 350 nm, 300 nm, 250 nm, 200 nm, 150 nm, 100 nm, 50 nm, 40 nm, 30 nm, 20 nm, 10 nm, 5 nm, 1 nm or less.

Structures on a fluidic device may be patterned or arranged for a particular application. In some configurations, structures may form points of contact for joining to other fluidic device components. In other configurations, structure may be formed or patterned for fluidic functions, e.g., wells for separated biological assays. In some configurations, structures on a fluidic device component may be patterned to create binding sites or capture sites for molecules or other particles. Structures may be arranged in a regular or irregular fashion. Regularly patterned structures may be formed in patterns such as rows, columns, or arrays. Individual structures in an array may be separated by a characteristic distance. The separation distance between structures may be determined by the intended function of the flow device. For example, a distance between structures with assay or detection functions may be sufficient to allow optically distinct or optically resolvable separation.

Figure 17:
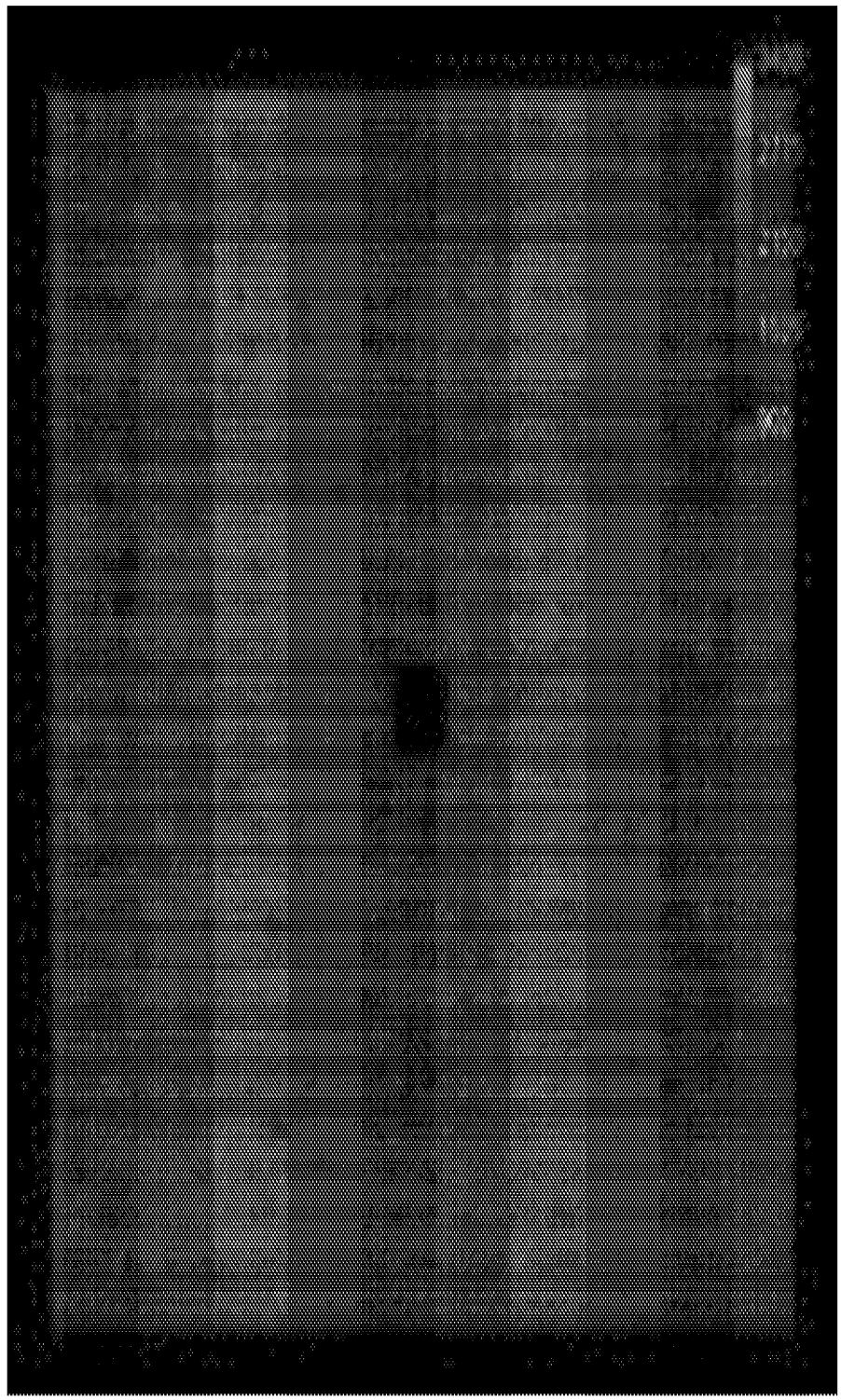
FIG. 17 shows an image of a microarray coated in fluorescent structured nucleic acid particles, in accordance with some embodiments.

A substrate may be patterned in a microarray comprising a plurality of functional sites (sites are also referred to herein as "addresses"). A substrate may be patterned in a regular fashion (e.g., a grid pattern) or may be irregularly patterned within a defined region of a substrate. A regularly patterned microarray may comprise a grid of a particular size, for example 1000000 active sites may be patterned in a 1000× 1000 array. A microarray may comprise multiple domains of differing surface chemistries or surface modifications. FIG. 17 shows an image of an embodiment of a microarray on a glass substrate with fluorescent capture agents conjugated to patterned active sites on a substrate surface. A microarray may also comprise other patterned domains, such as domains of passivated surface, domains of blocking groups, and fiducial domains.

In some configurations, a substrate may be initially cleaned, such as with a piranha cleaning. In some embodiments, a substrate may be cleaned using a strong acid so as to clean the substrate without etching the substrate. In some embodiments, a substrate may be cleaned using a detergent. Alternatively, a substrate may be cleaned with solvent, sonication or with plasma such as $O_2$ or $N_2$ plasma, or with a combination thereof.

Once a substrate has been cleaned, a layer may be deposited on the backside of the substrate. In some configurations, a deposited layer may be chrome or other optically-reflective materials. Deposition methods may include, for example, evaporation or sputtering. In some embodiments, a backside chrome evaporation may not be applied when a substrate is opaque. A backside layer may have a thickness of about one Angstrom, two Angstroms, 10 Angstroms, 10 nanometers, 20 nanometers, 30 nanometers, 40 nanometers, 50 nanometers, 60 nanometers, 70 nanometers, 80 nanometers, 90 nanometers, 100 nanometers, 150 nanometers, 200 nanometers, 250 nanometers, 300 nanometers, 400 nanometers, 500 nanometers, or more than 500 nanometers. A backside layer may have a thickness of at least about one Angstrom, two Angstroms, 10 Angstroms, 10 nanometers, 20 nanometers, 30 nanometers, 40 nanometers, 50 nanometers, 60 nanometers, 70 nanometers, 80 nanometers, 90 nanometers, 100 nanometers, 150 nanometers, 200 nanometers, 250 nanometers, 300 nanometers, 400 nanometers, 500 nanometers, or more than 500 nanometers or more. Alternatively or additionally, a backside layer may have a thickness of no more than about 500 nm, 400 nm, 300 nm, 250 nm, 200 nm, 150 nm, 100 nm, 90 nm, 80 nm, 70 nm, 60 nm, 50 nm, 40 nm, 30 nm, 20 nm, 10 nm, 10 Angstroms, 2 Angstroms or less. Alternatively, other metals can be used for deposition on the backside of a substrate, such as Aluminum, Tungsten, and/or Titanium, among other examples. Alternatively, dielectric mirrors can be used for deposition on the backside of a substrate.

Further, fiducials may be created on the front side of a substrate. Fiducials may be created by adding at least one layer of material and by patterning this at least one layer. In some embodiments, such material can be chrome, and/or such materials may be other metals like tungsten or gold. Alternatively, dielectric mirrors may be used as a material for fiducials. Alternatively, metal oxide may be used for a fiducial as for example $ZrO_2$. Patterning of such materials can be performed in a variety of ways. A first way to pattern a fiducial material is to deposit a blanket layer of the material, then to protect this material in selected areas and remove the material in the areas where it is not protected. This can for example be achieved by coating a front side of the substrate with photosensitive material (e.g. photoresist), patterning this photoresist by exposing it to UV light through a mask and then developing it. Etching of the fiducial material can then be performed by wet etch (for example acid) or dry etch (for example Reactive Ion Etching, RIE). Alternatively, a photoresist may be deposited and patterned first. In some embodiments where a photoresist is deposited and patterned first, areas are defined that are free of such photoresist and then a fiducial material may be deposited on top of the photoresist. The photoresist may then be removed (for example, in a solvent bath with sonication) and a fiducial material may be left on the areas that were initially free of photoresist (e.g., using a lift-off technique). Alternatively, fiducials may be created by removing material from the substrate in selected areas, for example by patterning a layer of photoresist on the front side of a substrate and then by dry etching the substrate in the areas that are not coated with photoresist. In another alternative, fiducials may be defined by modifying a substrate locally (for example by laser melting and/or fractioning). Fiducials may come in a variety of shapes, lines, and/or orientations. In some embodiments, a pattern of fiducials may be applied to the substrate. In yet another embodiment, the shape of a fiducial may vary in order to code information about their location on a surface of a substrate.

Once one or more fiducials are created on a front side of a substrate, this front side may be differentially coated to define features where biological objects of interest (for example, nucleic acid clusters covalently attached to a protein) may be immobilized. In a first embodiment, the surface may be differentially patterned with two silanes, for example HMDS or a PEG-silane in the field and APTES on immobilization spots. This differential patterning may be achieved by, for example, depositing an initial HMDS layer on the surface, followed by a lift-off layer, followed by an optional anti-reflective layer, and followed by a photoresist layer. In some embodiments, an anti-reflective layer may not be provided when an opaque substrate is being used.

Once a photoresist is applied, a second lithography step may be provided. In particular, particular features may be provided. In some embodiments, particular features may have a length of approximately 300 nm. In some embodiments, features may have a length of less than 700 nm, 600 nm, 500 nm, 400 nm, 300 nm, 250 nm, 200 nm, 150 nm, 100 nm, 50 nm or less. Alternatively or additionally, features may have a length of at least about 50 nm, 100 nm, 150 nm, 200 nm, 250 nm, 300 nm, 400 nm, 500 nm, 600 nm, 700 nm or more. In some further embodiments, one or more layers deposited on the surface to perform this second lithography may not be etched by the developing step of this second lithography (for example, the antireflective coating).

In embodiments where a backside coating is provided, the backside coating may be removed, such as through the use of a wet etch or dry etch etc. Further, a directional reactive ion etch (RIE) may be provided so as to remove layers that haven't been removed by the lithography step (for example the antireflective coating).

Figure 9:
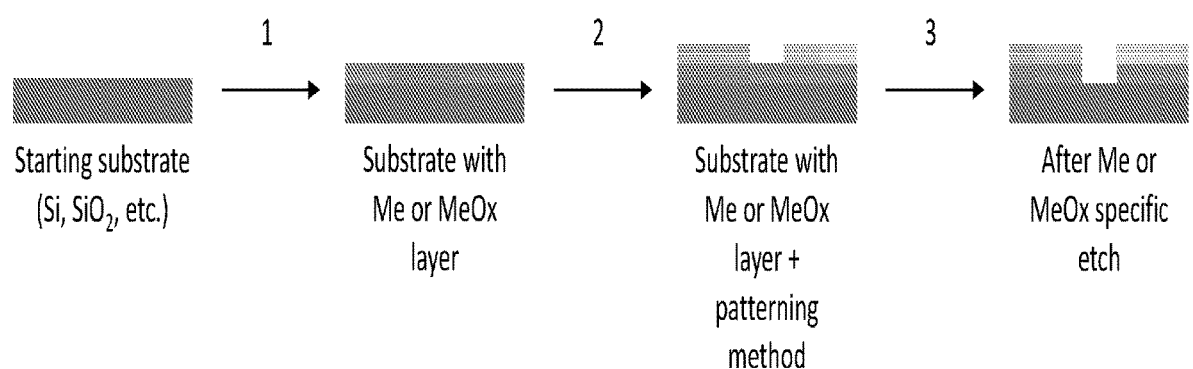
FIG. 9 depicts a process of structuring a $ZrO_2$-coated surface, in accordance with some embodiments.

FIG. 9 illustrates an example of preparing a patterned metal (Me) or metal oxide (MeOx) (e.g., Au or $ZrO_2$) substrate, in accordance with disclosed embodiments. The process begins with a starting substrate, such as silicon (Si), silicon dioxide ($SiO_2$), extruded glass, fused silica, quartz, noble metals, metal oxides, etc. First, a layer of a metal or metal oxide is formed on top of a substrate. This can be performed using a suitable method that achieves the layer thickness and uniformity, such as via atomic layer deposition (ALD), sol-gel layer formation from metal precursors, or phosphate-mediated metal ion immobilization (e.g., preparation of a phosphate-terminated substrate surface followed by exposure to $Zr^{4+}$ ions in solution to prepare a terminal $ZrO_2$ layer). Second, a patterned surface is formed on top of a metal or metal oxide layer. This can be performed by a suitable surface patterning method to achieve a spatial resolution, feature size, or other specifications, with or without metal or metal oxide-selective etch, such as via contact masking, stenciling, contact printing (e.g., nano/microcontact printing such as stamping), photolithography (e.g., using a positive photoresist or a negative photoresist), or other nanopatterning or micropatterning techniques. Third, a metal or metal oxide-specific etch is optionally performed to create a patterned metal or metal oxide on a substrate.

The separation between structures on a fluidic device component may be at least about 5 nm, 10 nm, 20 nm, 30 nm, 40 nm, 50 nm, 100 nm, 150 nm, 200 nm, 250 nm, 300 nm, 350 nm, 400 nm, 450 nm, 500 nm, 600 nm, 700 nm, 800 nm, 900 nm, 1 µm, 10 µm, 50 µm, 100 µm, 250 µm, 500 µm, 750 µm, 1 mm, 5 mm, or about 1 cm or more. Alternatively or additionally, the separation of structures on a fluidic device component may be no more than about 1 cm, 5 mm, 1 mm, 750 µm, 500 µm, 250 µm, 100 µm, 50 µm, 10 µm, 1 µm, 900 nm, 800 nm, 700 nm, 600 nm, 500 nm, 450 nm, 400 nm, 350 nm, 300 nm, 250 nm, 200 nm, 150 nm, 100 nm, 50 nm, 40 nm, 30 nm, 20 nm, 10 nm, 5 nm or less.

The inner surfaces of a fluidic device, including all areas in physical contact with a fluid may comprise a functionality, mask, adsorbent, texture, microstructure, capture agent, catalyst, deposit, coating, or other surface alteration. The application of a functionality, mask, adsorbent, texture, microstructure, capture agent, catalyst, deposit, coating, or other surface alteration may include altering hydrophobicity, altering hydrophilicity, altering amphipathicity, altering surface tension or surface energy, altering the physical, chemical, electrical, mechanical, or optical characteristics of the fluidic channel, affecting fluid flow or altering fluid properties, increasing or decreasing heat transfer or mass transfer, capturing or adsorbing species from a fluid, preventing adhesion of species from a fluid, performing chemical reactions, and other operations.

In some configurations, a substrate may be modified across the entire surface to which molecules are to be attached. In other configurations, the solid support may contain regions which are modified to allow attachment of molecules and regions which are not modified, or regions which are modified to decrease attachment of molecules and regions which are not modified, or regions which are modified to increase attachment of molecules and regions which are modified to decrease attachment of molecules. In some configurations, attachment sites may be created in an array, for example an ordered array. An ordered array of attachment sites may be created by, for example, photolithography, Dip-Pen nanolithography, nanoimprint lithography, nanosphere lithography, cluster lithography, nanopillar arrays, nanowire lithography, scanning probe lithography, thermochemical lithography, thermal scanning probe lithography, local oxidation nanolithography, molecular self-assembly, stencil lithography, or electron-beam lithography.

Attachment sites in an ordered array may be located such that each attachment site is at least about 20 nm, 50 nm, 75 nm, 100 nm, 125 nm, 150 nm, 175 nm, 200 nm, 225 nm, 250 nm, 275 nm, 300 nm, 325 nm, 350 nm, 375 nm, 400 nm, 450 nm, 500 nm, 600 nm, 700 nm, 800 nm, 900 nm, 1000 nm, 1200 nm, 1500 nm, 2000 nm or more from other attachment sites. Alternatively or additionally, attachment sites in an ordered array may be located such that each attachment site is no more than about 2000 nm, 1500 nm, 1000 nm, 900 nm, 800 nm, 700 nm, 600 nm, 500 nm, 450 nm, 400 nm, 375 nm, 350 nm, 325 nm, 300 nm, 275 nm, 250 nm, 225 nm, 200 nm, 175 nm, 150 nm, 125 nm, 100 nm, 75 nm, 50 nm, 20 nm or less from other attachment sites. In some configurations, spacing of attachment sites on the solid support may be selected depending on the size of the moiety or ligand to be attached. For example, spacing of attachment sites may be selected such that a distance between the edges of two attachment sites is greater than the diameter of a structured nucleic acid particle that is used. In some configurations, the attachment sites may be provided in microwells or nanowells.

In some configurations, functional groups on a functionalized substrate surface may be present in a random spacing and may be provided at a concentration such that functional groups are on average at least about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1000 nm, or more from other functional groups. Alternatively or additionally, functional groups may be provided at a concentration such that functional groups are on average no more than about 1000 nm, 950 nm, 900 nm, 850 nm, 800 nm, 750 nm, 700 nm, 650 nm, 600 nm, 550 nm, 500 nm, 450 nm, 400 nm, 350 nm, 300 nm, 250 nm, 200 nm, 150 nm, 100 nm, 50 nm or less. The solid support may be indirectly functionalized. For example, the solid support may be PEGylated and a functional group may be applied to all or a subset of the PEG molecules.

Surface Modifications

One or more surfaces within a fluidic device may be modified with a surface functionalization or ligand. A surface functionalization or ligand may be deposited on a surface as a monolayer, self-assembling monolayer, or multiple layers (e.g., stacked cross-linked layers). A surface functionalization or ligand may be deposited by a method such as solution-phase and gas-phase deposition methods. A surface functionalization or ligand may be specific to a particular substrate. For example, a phosphate or phosphonate compound may be preferably deposited on a metal oxide layer or a silane may be preferably deposited on a silica surface. A surface functionalization or ligand may comprise a coordination complex on a substrate or other surface. A surface functionalization or ligand may comprise an inorganic molecule, an organic molecule, or a combination thereof.

Figure 4:
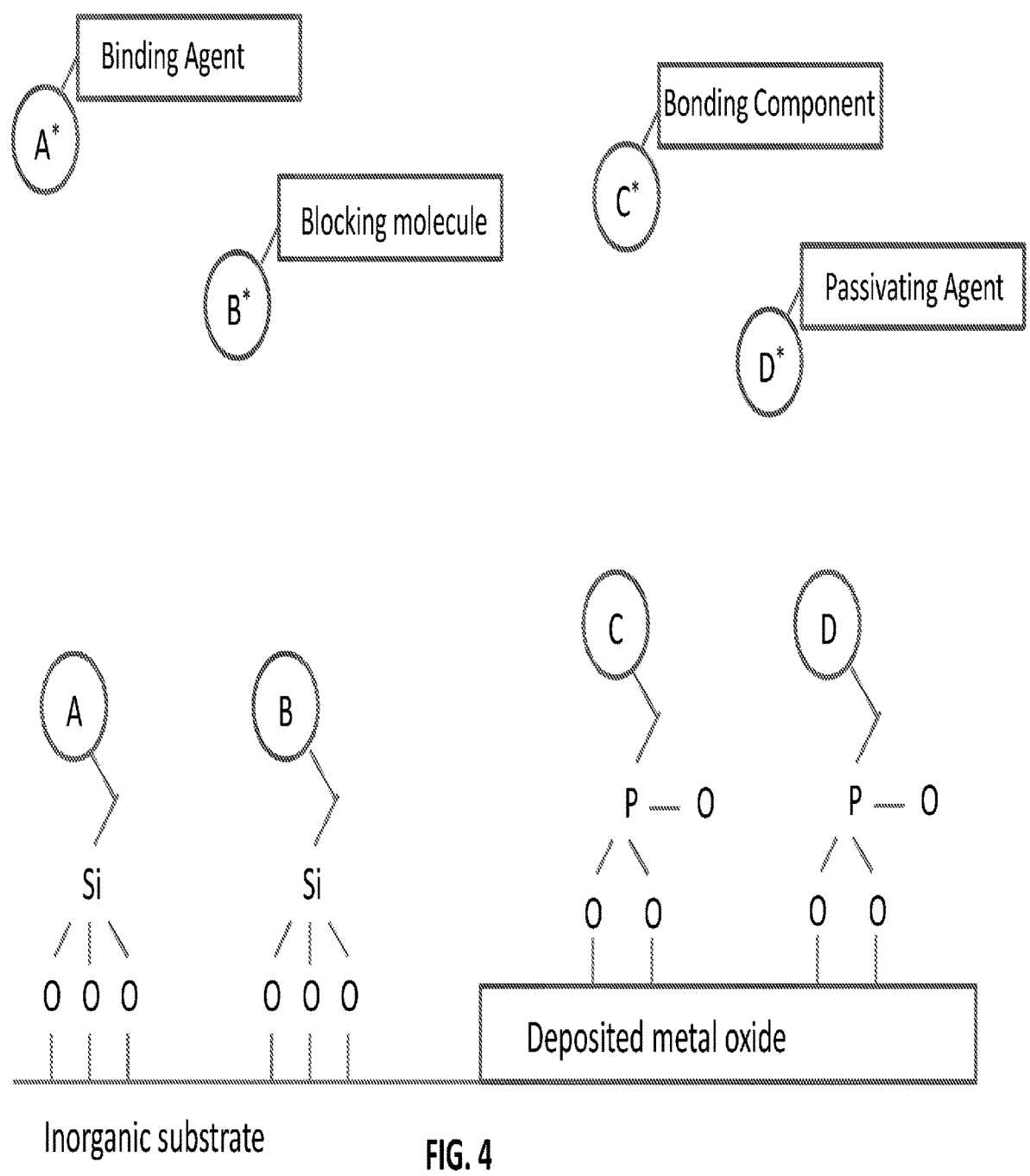
FIG. 4 shows a conceptual schematic of a surface containing multiple types of surface functionalizations, in accordance with some embodiments.
Figure 13:
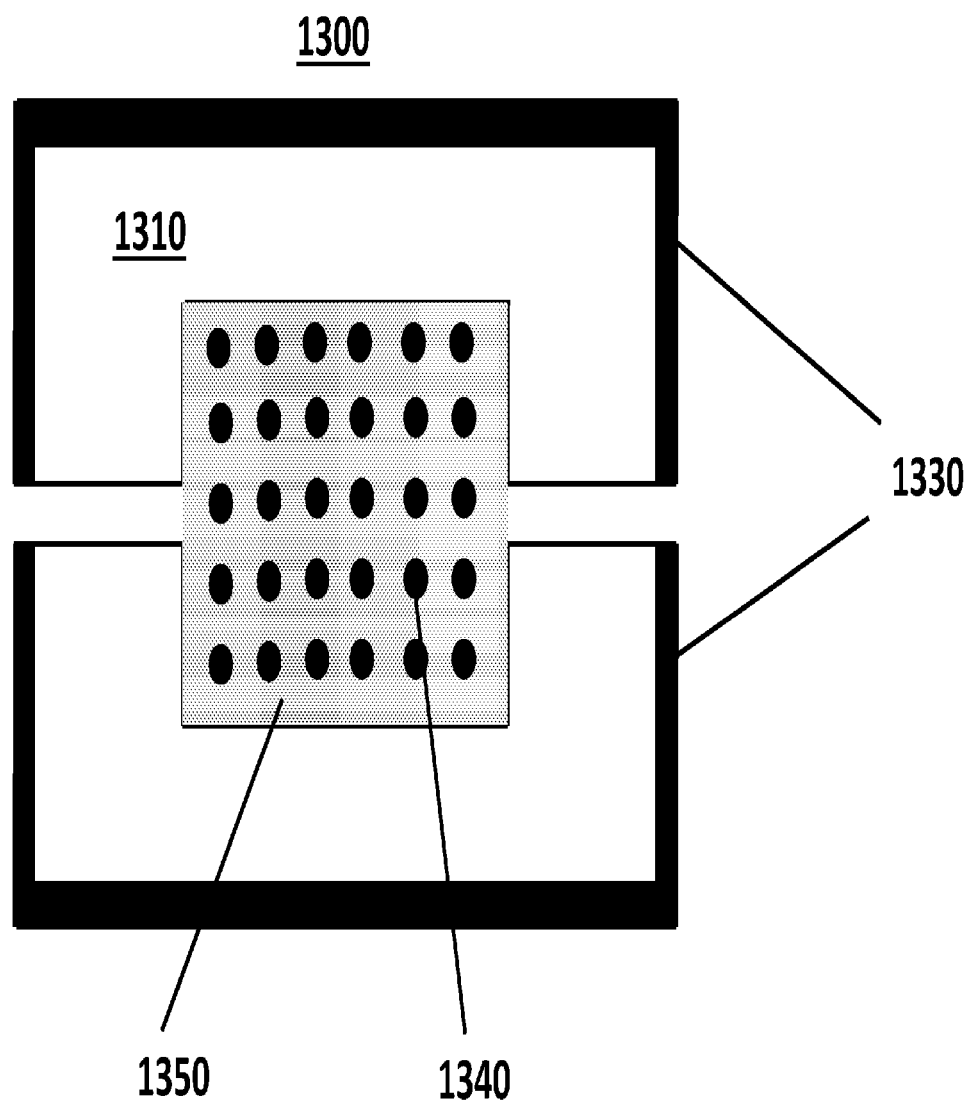
FIG. 13 shows a schematic of an exemplary fluidic device with a micropatterned array of capture regions surrounded by a passivated surface, in accordance with some embodiments.

One or more surfaces within a fluidic device may be modified with more than one type of surface functionalization or ligand. For example, a silica surface may comprise two or more types of organosilanes where a distinguishing feature between organosilanes is a specific chemistry of the organosilane chains. FIG. 4 shows an exemplary cross-section of a surface in a fluidic device comprising an inorganic surface and a metal oxide surface, each functionalized with multiple types of ligands. Each ligand may be configured to form a link or bond with a complementary surface component, e.g. A-A* to link a binding group to a surface. The example in FIG. 4 should not be seen to limit the possible embodiments of the present disclosure. Chemistries applied to a given surface can be adapted to create a structure or function on the given surface. For example, the binding component C* of FIG. 4 may be linked to a surface ligand on an inorganic substrate or a metal oxide depending upon the respective applied chemistries. In some configurations, a surface ligand may alter or create a surface characteristic without further modification. Specific surface functionalizations or ligands may be applied on particular surfaces or on particular regions of a surface to create spatially distinct regions with differing surface chemistries. FIG. 13 shows an exemplary fluidic device 1300 comprising a surface 1310 with differentiated regions of surface chemistry. Near the outer edges of the fluidic device 1300 are bonding regions 1330 for joining other fluidic device components to a surface (e.g., a cover piece). In the central region on the fluidic device 1300 is a passivated surface 1350 with patterned regions 1340 with enhanced adhesion properties for the capture of macromolecules. Surface functionalizations or ligands may be used to alter the chemical or physical properties of a surface. A surface functionalization or ligand may be used for an alteration to a surface, including passivating a surface, increasing or decreasing adhesion or adsorption of chemical species on a surface, increasing or decreasing the reactivity of a surface, binding, linking, or connecting two or more surfaces together, altering fluid flow properties (e.g., decrease flow friction), and altering other surface properties such as hydrophobicity, hydrophilicity, amphipathicity, or surface energy.

In some embodiments, surfaces of the solid support may be modified to allow or enhance covalent or non-covalent attachment of molecules such as structured nucleic acid particles. The solid support and process for molecule attachment are stable for repeated binding, washing, imaging and eluting steps. In some configurations, surfaces may be modified to have a positive or negative charge. In some configurations, surfaces may be functionalized by modification with specific functional groups, such as maleic or succinic moieties, or derivatized by modification with a chemically reactive group, such as amino, thiol, or acrylate groups, such as by silanization. Suitable silane reagents include aminopropyltrimethoxysilane, aminopropyltriethoxysilane and 4-aminobutyltriethoxysilane. Surfaces may be functionalized with N-Hydroxysuccinimide (NHS) functional groups. Glass surfaces can also be derivatized with other reactive groups, such as acrylate, epoxy, or thiol, using, e.g., epoxysilane, acrylatesilane, mercaptosilane, or acrylamidesilane.

Using methods and systems of the present disclosure, surface functionalization and passivation may be performed, which may be advantageous because functionalizing and passivating molecules can be localized to specific surface areas based upon a surface material and chemistry. For example, silanated surface functionalizations can be bound to silica surfaces while phosphate passivating groups can be bound to metal oxide surfaces. Surface functionalizations and surface passivations may be bound to a surface covalently and may be less susceptible to degradation via hydrolysis or other mechanisms. This may lead to more stable and effective coatings in functional and passivated areas on a surface under a wider variety of conditions and over a longer period of time.

Further, the methods provided herein may create coatings of substantially uniform thickness and may be less susceptible to poorly-controlled layer growth. Inorganic, metal, or metal oxide surfaces may enable precision functional and passivated coatings using covalently bound functional groups such as silanes, phosphates, or phosphonates. A number of phosphate or phosphonate-containing molecules (e.g., $HPO_3^{2-}$, (aminomethyl)phosphonic acid, PEG-phosphonate) may be easily deposited from solution or vapor phase on metal or metal oxide (e.g., Au or $ZrO_2$) surfaces in a self-limited fashion (e.g., formation of self-assembled monolayers, SAMs). Metal or metal oxide/phosphate or phosphonate coatings may be limited to forming SAMs, so process uniformity may be easily controlled. Likewise, silane compounds (e.g., APTMS, APTES, mercaptosilane) may be deposited from solution or vapor phase on a substrate such as silica or fused silica in a self-limited fashion.

Certain metals or metal oxides (e.g., Au or $ZrO_2$) may interact strongly with phosphates and phosphonates, so methods and systems of the present disclosure may also be used to prepare patterned areas of directly-immobilized biomolecules, such as DNA, RNA, phosphopeptides, and phosphoproteins, without the need for additional surface modifications after a metal or metal oxide coating is prepared. Silicon and silica substrates may interact strongly with silanes so methods and systems of the present disclosure may also be used to prepare patterned areas of directly-immobilized biomolecules, such as DNA, RNA, phosphopeptides, and phosphoproteins, without the need for additional surface modifications after the substrate is prepared.

Through patterning, silane methods (and other material-specific coating methods) may be compatible with metal or metal oxide-coated surfaces. For example, a Si or $SiO_2$ substrate can be coated with $ZrO_2$, which can be selectively etched to produce a surface with patterned areas of $SiO_2$ and $ZrO_2$. Silane chemistry may be used to selectively functionalize or passivate the $SiO_2$ regions, then phosphate or phosphonate chemistry may be used to functionalize or passivate the $ZrO_2$ regions, or vice versa. In some configurations, a substrate surface may be completely functionalized or completely passivated. In other configurations, specific areas of a fluidic surface may be functionalized and other areas may be passivated.

Figure 16A:
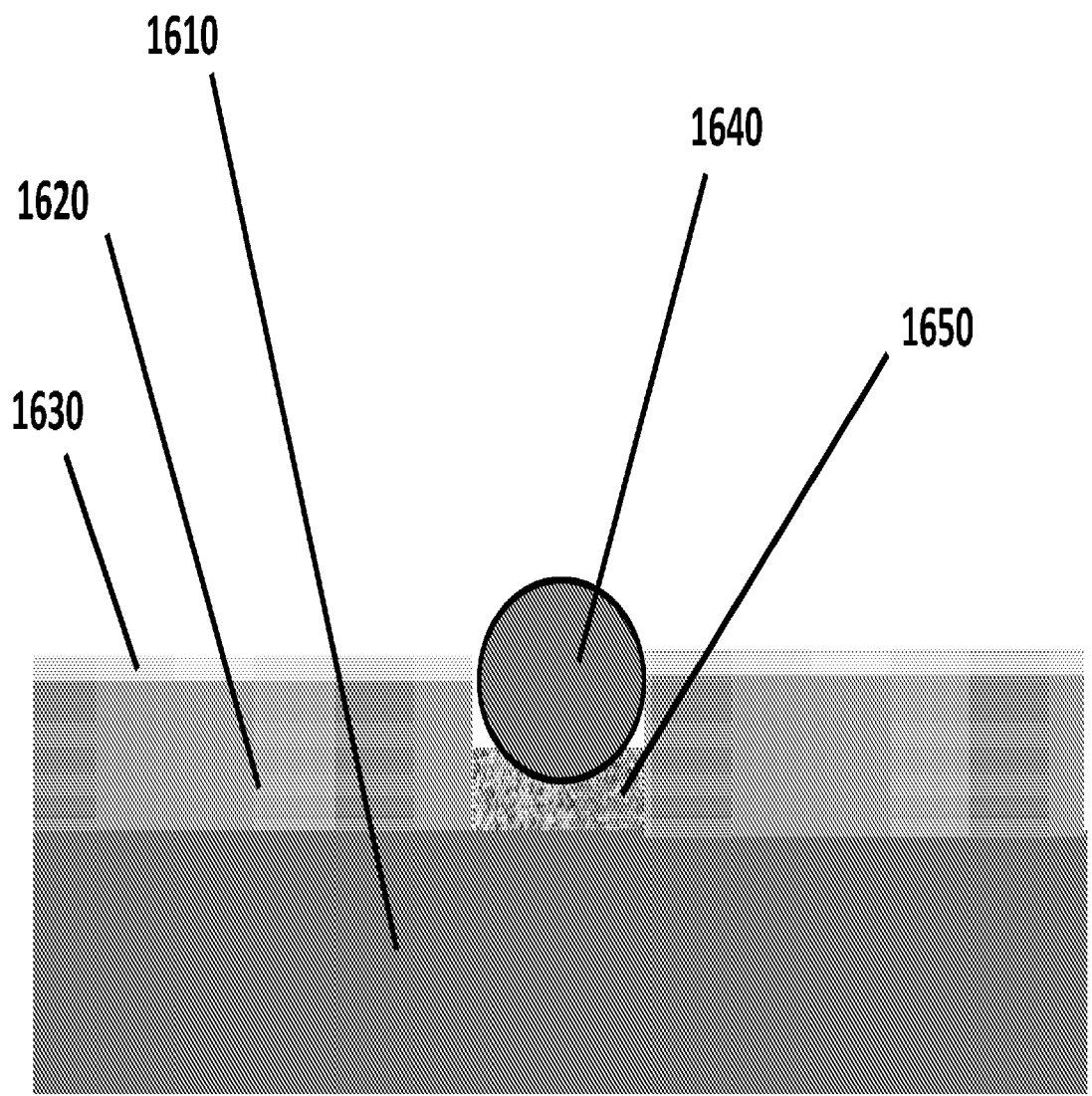
FIG. 16A shows a substrate containing a binding group surrounded by a passivated surface, in accordance with some embodiments.
Figure 16B:
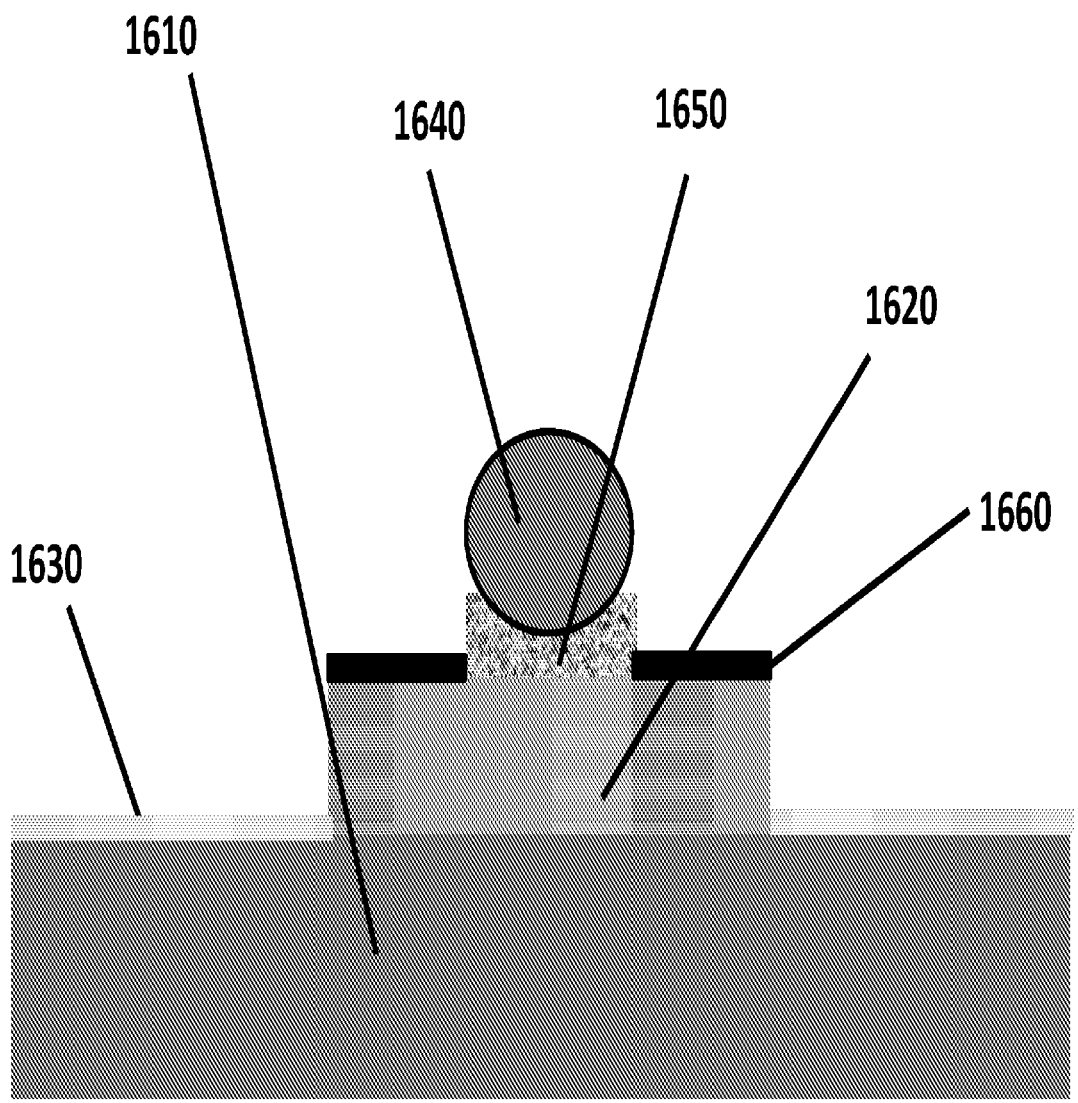
FIG. 16B shows an elevated surface with a binding group surrounded by blocking groups, in accordance with some embodiments.

Surface functionalizations or ligands of the present disclosure may increase the capture efficiency of a particular target molecule. FIGS. 16A and 16B illustrates an example of placing a capture agent at a selected region of a substrate surface with surrounding surfaces passivated by a passivating agent, in accordance with disclosed embodiments. In some configurations, a binding component or capture agent may be smaller than the selected region to which it is bound. In such configurations, the remaining uncovered surface may contain passivating or blocking agents to prevent molecular capture at a location other than the binding agent. In a particular configuration shown in FIG. 16A, the metal oxide areas 1620 (e.g., non-feature regions) deposited on the substrate 1610 are blocked with free phosphate 1630. Next, capture agents 1640 are immobilized to surface-bound organosilane ligands 1650 that specifically functionalize the substrate 1610 surface. In another configuration, shown in FIG. 16B, a metal oxide pillar or platform 1620 may be structured on a substrate surface 1610. A capture agent 1640 may be linked to the metal oxide pillar or platform 1620 by a phosphate or phosphonate surface-bound ligand 1650. Areas of the metal oxide pillar or platform 1620 that are not linked to the capture agent 1640 are functionalized with blocking molecules 1660. The remainder of the substrate surface 1610 is covered with a passivating layer 1630 comprising organosilanes or other compatible surface-bound compounds.

A target molecule may comprise a molecule (e.g. a protein) that is to be specifically isolated from a heterogeneous sample. In some configurations, a surface functionalization or ligand may increase capture of a target molecule by about 10%, 25%, 50%, 75%, 100%, 200%, 300%, 400%, 500%, 600%, 700%, 800%, 900%, or about 1000% when compared to a non-functionalized surface. In some configurations, a surface functionalization or ligand may increase capture of a target molecule by at least about 10%, 25%, 50%, 75%, 100%, 200%, 300%, 400%, 500%, 600%, 700%, 800%, 900%, or about 1000% or more when compared to a non-functionalized surface. Alternatively or additionally, a surface functionalization or ligand may increase capture of a target molecule by no more than 1000%, 900%, 800%, 700%, 600%, 500%, 400%, 300%, 200%, 100%, 75%, 50%, 25%, or 10% or less when compared to a non-functionalized surface. In some configurations, a surface functionalization or ligand may increase capture of a target molecule by about 2-fold, 3-fold, 5-fold, 10-fold, 100-fold, 1000-fold, 10000-fold, 100000-fold, or 1000000-fold when compared to a non-functionalized surface. In some configurations, a surface functionalization or ligand may increase capture of a target molecule by at least about 2-fold, 3-fold, 5-fold, 10-fold, 100-fold, 1000-fold, 10000-fold, 100000-fold, or 1000000-fold or more when compared to a non-functionalized surface. Alternatively or additionally, a surface functionalization or ligand may increase capture of a target molecule by no more than 1000000-fold, 100000-fold, 10000-fold, 1000-fold, 100-fold, 10-fold, 5-fold, 3-fold, 2-fold, or less when compared to a non-functionalized surface.

A surface functionalization or ligand may decrease capture efficiency of a non-target molecule. In some configurations, a surface functionalization or ligand may decrease capture of a non-target molecule by about 5%10%, 15%, 20%, 25%, 30%, 35%, 40%, 45%, 50%, 55%, 60%, 65%, 70%, 75%, 80%, 85%, 90%, 95%, 99%, or 99.9% when compared to a non-functionalized surface. In some configurations, a surface functionalization or ligand may decrease capture of a non-target molecule by at least about 5%, 10%, 15%, 20%, 25%, 30%, 35%, 40%, 45%, 50%, 55%, 60%, 65%, 70%, 75%, 80%, 85%, 90%, 95%, 99%, or 99.9% or more when compared to a non-functionalized surface. Alternatively or additionally, a surface functionalization or ligand may decrease capture of a non-target molecule by no more than 99.9%, 99%, 95%, 90%, 85%, 80%, 75%, 70%, 65%, 60%, 55%, 50%, 45%, 40%, 35%, 30%, 25%, 20%, 15%, 10%, 5% or less when compared to a non-functionalized surface. In some configurations, a surface functionalization or ligand may decrease capture of a target molecule by about 2-fold, 3-fold, 5-fold, 10-fold, 100-fold, 1000-fold, 10000-fold, 100000-fold, or 1000000-fold when compared to a non-functionalized surface. In some configurations, a surface functionalization or ligand may decrease capture of a target molecule by at least about 2-fold, 3-fold, 5-fold, 10-fold, 100-fold, 1000-fold, 10000-fold, 100000-fold, or 1000000-fold or more when compared to a non-functionalized surface. Alternatively or additionally, a surface functionalization or ligand may decrease capture of a target molecule by no more than 1000000-fold, 100000-fold, 10000-fold, 1000-fold, 100-fold, 10-fold, 5-fold, 3-fold, 2-fold, or less when compared to a non-functionalized surface.

Surface passivation may increase capture efficiency of a particular target molecule at a location by reducing the adhesion of the target molecule to non-functional areas of a substrate surface. A surface passivation may also decrease the fouling of a substrate surface by other non-target molecules. In some configurations, a surface passivation may increase the capture of a target molecule by about 10%, 25%, 50%, 75%, 100%, 200%, 300%, 400%, 500%, 600%, 700%, 800%, 900%, or about 1000% when compared to a non-passivated surface. In some configurations, a surface passivation may increase the capture of a target molecule by at least about 10%, 25%, 50%, 75%, 100%, 200%, 300%, 400%, 500%, 600%, 700%, 800%, 900%, or about 1000% or more when compared to a non-passivated surface. Alternatively or additionally, a surface passivation may increase the capture of a target molecule by no more than 1000%, 900%, 800%, 700%, 600%, 500%, 400%, 300%, 200%, 100%, 75%, 50%, 25%, or 10% or less when compared to a non-passivated surface. In some configurations, a surface passivation may increase the capture of a target molecule by about 2-fold, 3-fold, 5-fold, 10-fold, 100-fold, 1000-fold, 10000-fold, 100000-fold, or 1000000-fold when compared to a non-passivated surface. In some configurations, a surface passivation may increase the capture of a target molecule by at least about 2-fold, 3-fold, 5-fold, 10-fold, 100-fold, 1000-fold, 10000-fold, 100000-fold, or 1000000-fold or more when compared to a non-passivated surface. Alternatively or additionally, a surface passivation may increase the capture of a target molecule by no more than 1000000-fold, 100000-fold, 10000-fold, 1000-fold, 100-fold, 10-fold, 5-fold, 3-fold, 2-fold, or less when compared to a non-passivated surface.

A surface passivation may decrease the capture efficiency of a non-target molecule. In some configurations, a surface passivation may decrease the capture of a non-target molecule by about 10%, 25%, 50%, 75%, 100%, 200%, 300%, 400%, 500%, 600%, 700%, 800%, 900%, or about 1000% when compared to a non-passivated surface. In some configurations, a surface passivation may decrease capture of a non-target molecule by at least about 10%, 25%, 50%, 75%, 100%, 200%, 300%, 400%, 500%, 600%, 700%, 800%, 900%, or about 1000% or more when compared to a non-passivated surface. Alternatively or additionally, a surface passivation may increase capture of a non-target molecule by no more than 1000%, 900%, 800%, 700%, 600%, 500%, 400%, 300%, 200%, 100%, 75%, 50%, 25%, or 10% or less when compared to a non-passivated surface. In some configurations, a surface passivation may decrease capture of a target molecule by about 2-fold, 3-fold, 5-fold, 10-fold, 100-fold, 1000-fold, 10000-fold, 100000-fold, or 1000000-fold when compared to a non-passivated surface. In some configurations, a surface passivation may decrease capture of a target molecule by at least about 2-fold, 3-fold, 5-fold, 10-fold, 100-fold, 1000-fold, 10000-fold, 100000-fold, or 1000000-fold or more when compared to a non-passivated surface. Alternatively or additionally, a surface passivation may decrease capture of a target molecule by no more than 1000000-fold, 100000-fold, 10000-fold, 1000-fold, 100-fold, 10-fold, 5-fold, 3-fold, 2-fold, or less when compared to a non-passivated surface.

In some configurations, a passivation layer may include diamond-like carbon, hexa-methyldisilizane, Teflon, fluorocarbon, a polymer such as polyethylene glycol (PEG) and/or Parylene. In some embodiments, a solid support may be passivated by attachment of Polyethylene glycol (PEG) molecules across a solid support. In some configurations, a solid support may be passivated using a nucleic acid (e.g., salmon sperm DNA), glycols, albumin, or a combination of the above. In some configurations, a solid support may be passivated using one or more components selected from the group consisting of DNA, RNA, glycols, and albumin. In some configurations, passivation components may be exposed to a surface. In some embodiments, passivation components may not be covalently bound to a surface. In some configurations, passivation materials may be not covalently bound to a solid support.

In some embodiments, methods and systems of the present disclosure may comprise passivation or functionalization for specific target molecules or particle immobilization. Different passivated or functionalized regions of metal or metal oxide (e.g., Au or $ZrO_2$) can be prepared with reagents such as phosphates, phosphonates, and their derivatives. For example, passivating or functionalizing using phosphate or phosphonate may include one or more of: direct immobilization of phosphate- or phosphonate-containing (bio)molecules (e.g., DNA); amine-terminated phosphates and phosphonates (e.g., (Aminomethyl)phosphonic acid [CAS:1066-51-9]); Aminoalkyl phosphates, phosphonates, or related molecules or compounds with varying alkyl chain length, such as (Aminoethyl)phosphonic acid and (Aminopropyl) phosphonic acid); Carboxy-terminated phosphates and phosphonates, including Carboxyalkyl phosphates, phosphonates, or related molecules or compounds, such as (Carboxymethyl)phosphonic acid [CAS:4408-78-0] and related carboxyalkylphosphonates with varying alkyl chain length; Phospholipids and alkyl-terminated phosphates and phosphonates, such as alkylphosphonic acids, or related molecules or compounds (e.g., octadecylphosphonic acid (ODPA) [CAS:4724-47-4] and related alkylphosphonates with varying alkyl chain length); and thiol-terminated phosphates and phosphonates, such as Thiophospate [CAS: 10489-48-2] or related molecules or compounds with varying chain lengths, side groups, and/or compositions.

Different passivated or functionalized regions of silicon, silica, or glass substrates (e.g., fused silica) can be prepared with reagents such as silanes, organosilanes, and their derivatives. For example, passivating or functionalizing using silanes or organosilanes may include one or more of: amine-terminated silanes (e.g., (3-aminopropyl)triethoxysilane [CAS:919-30-2]; (3-aminopropyl)trimethoxysilane [CAS: 13822-56-5]); amine-terminated silanes with secondary amines (e.g., N-(6-aminohexyl)aminomethyl triethoxysilane [15129-36-9]; N-(2-aminoethyl)-3-aminopropyl triethoxysilane [CAS 5089-72-5]; N-(2-aminoethyl)-3-aminopropyl triethoxysilane [CAS 1760-24-3]; halogenated or hydrogenated silanes (e.g., chloro-dimethylsilane [CAS: 1066-35-9]; 4-bromobutyl trimethoxysilane [CAS 226558-82-3]; 7-bromoheptyl trimethoxysilane; 5-bromopentyl trimethoxysilane [773893-02-0]; 3-bromopropyl trimethoxysilane [CAS 51826-90-5]; 11-bromoundecyl trimethoxysilane [CAS 17947-99-8]; 3-chloroisobutyl trimethoxysilane [17256-27-8]; 2-(chloromethyl)allyl trimethoxysilane [CAS 39197-94-9] or triethoxy silane [CAS: 2487-90-3]); silanes with alkyl sidechains or varying length (e.g., trimethoxypropylsilane [CAS: 1067-25-0]); thiol-terminated silanes (e.g., (3-mercaptopropyl)trimethoxysilane [CAS: 4420-74-0]); epoxidated silanes (e.g., 2-(3,4-epoxycyclohexyl)ethyl triethoxysilane [CAS 10217-34-2]; 2-(3,4-epoxycyclohexyl)ethyl trimethoxysilane [CAS 3388-04-3]; 5,6-epoxyhexyl triethoxysilane [CAS 86138-01-4]; (3-glycidoxypropyl)triethoxysilane [CAS 2602-34-8]; (3-glycidoxypropyl)trimethoxysilane [CAS: 2530-83-8]; 2-(3,4-epoxycyclohexyl)ethylmethyl diethoxysilane [CAS 14857-35-3]; (3-glycidoxypropyl)methyl diethoxysilane [CAS 2897-60-1]; (3-glycidoxypropyl)methyl dimethoxysilane [CAS 65799-47-5]; (3-glycidoxypropyl)dimethyl ethoxysilane [CAS 17963-04-1]; ester-functionalized silanes (e.g., acetoxymethyl triethoxysilane [CAS 5630-83-1]; acetoxymethyl trimethoxysilane [CAS 65625-39-0]; 2-[(acetoxy (polyethyleneoxy)propyl]triethoxysilane; 3-acetoxypropyl trimethoxysilane [CAS 59004-18-1]; benzoyloxypropyl trimethoxysilane [CAS 76241-02-6]; 10-(carbomethoxy) decyldimethyl methoxysilane [CAS 1211488-83-3]; 2-(carbomethoxy)ethyl trimethoxysilane; triethoxysilylpropoxy (polyethyleneoxy)dodecanoate [1041420-54-5]; azide functionalized silanes (e.g., azido(trimethyl) silane [CAS 4648-54-8]); silanes with click functional groups (e.g., DBCO-PEG-silane, TCO (triethoxy) silane, methyltetrazine-silane); and silanes with other reactive sidechains (e.g., triethoxy-vinylsilane [CAS: 78-08-0]), or related molecules or compounds with varying chain lengths, side groups, and/or compositions.

A surface functionalization may comprise organic chains containing reactive groups. The reactive groups may be located at a position within a chain, including at a terminal position (e.g., a terminal carboxylic acid group), within a chain (e.g., a secondary amine), or pendant to an atom within a chain (e.g., a non-terminal carboxylic acid group). In some configurations, an organic chain may comprise more than one functional group (e.g., a primary amine and a secondary amine). In some configurations, an organic chain may include more than one functional group to create more than one chemical property (e.g., two differing types of reactivity; chemical reactivity and hydrophobicity). In some configurations, a surface functionalization may comprise more than one functional group to increase the likelihood of a chemical process occurring (e.g., primary and secondary amines to increase the likelihood of reaction with an amine group).

In some embodiments, methods and systems of the present disclosure may comprise passivating groups or blocking groups to prevent binding (e.g., to small molecules, peptides, proteins, nucleic acids, and nanoparticles). Passivating agents may include organic or inorganic coatings such as metals, metal oxides, and ionic compounds. Surface passivating agents may bond with or adsorb to active sites or defects on the surface of a fabricated substrate, thereby blocking adhesion of other molecules to active sites or defects. A surface passivating agent may be applied as a coating, a monolayer or may specifically react at sites that require passivating. A surface passivating agent may be applied via a liquid or gas phase reaction, or a liquid or gas phase deposition. A blocking group may include a group that prevents other molecules from binding to a surface by physically blocking or repelling other molecules from approaching a surface. Blocking molecules may include steric blockers such as branched polymers (e.g., PEG) or long-chain alkyls. Blocking molecules may include molecules that create repulsion by electrical or magnetic fields, such as ionic chains or polymers or magnetic nanoparticles.

Different passivated or blocked regions of a metal or metal oxide (e.g. Au or $ZrO_2$) can be prepared with reagents such as phosphates, phosphonates, and their derivatives. For example, passivating or blocking using phosphate or phosphonate may include one or more of: free phosphate or hydrogen phosphate, or dihydrogen phosphate; Phosphate-terminated PEG reagents (with various lengths and branching); Bis- or tris-phosphates or phosphonates (di- and tri-phosphonates) (e.g., molecules of varying compositions that have two or more terminal phosphates or phosphonate groups linked by a particular size or composition of alkyl, amide, ester, carboxylic acid, alcohol, carbonyl, or other chemical moieties), such as etidronic acid [CAS:25211-86-3] and Nitrilotri(methylphosphonic acid) [CAS:6419-19-8]. In some configurations, a passivating or blocking group may be deposited in step-wise fashion on a metal or metal oxide surface by first depositing a compound such as a phosphate or phosphonate (e.g., an epoxy-terminated phosphate), then reacting the epoxy group with a reactive group on a blocking molecule (e.g. an amine-terminated PEG molecule). In other configurations, a passivating agent or blocking group may be deposited in a single step.

Different passivated regions of a silicon, silica, or glass substrates (e.g., fused silica) can be prepared with reagents such as silanes, organosilanes, and their derivatives. For example, passivating suing silanes or organosilanes may include one or more of: silane ($SiH_4$) or halogenated silanes (e.g., $SiCl_3H$); silane-terminated PEG reagents (with various lengths and branching); disilanes, trisilanes, or larger oligomerized silanes (e.g., 2 or more bonded silicon atoms with hydrogenated, halogenated, or alkyl side groups); or silanes with alkyl side groups (e.g., butylsilane). In some configurations, a passivating or blocking group may be deposited in step-wise fashion on an inorganic substrate surface such as silicon, silica, or glass substrate, by first depositing a compound such as a silane or organosilane (e.g., an epoxy-terminated silane), then reacting an epoxy group with a reactive group on a blocking molecule (e.g. an amine-terminated PEG molecule). In other configurations, a passivating agent or blocking group may be deposited in a single step.

A surface may be functionalized with an organic or inorganic ligand to create bonding regions for joining together fluidic device components. An organic or inorganic ligand may include a silane, an organosilane (e.g. PEG-silane), a silane derivative (e.g. APTES), a thiol, a thiol derivative, a catechol, HMDS, or a synthetic or natural polyphenol such as L-dopamine, pyrocatechol, pyrogallol, or tannic acid. In some configurations, a silane derivative may comprise a functional group such as an electrophilic group (e.g., epoxy or alkynyl) or a nucleophilic group (e.g., thiol, amine). A metal or metal oxide layer may comprise other deposited species such as free phosphates, derivatized phosphates, and free metal ions such as $Zr^{4+}$, $Ti^{4+}$, or $Hf^{4+}$. In some configurations, organosulfide ligands might be used to functionalize a surface, such as an Au layer deposited on a glass substrate. A surface may be functionalized with various low-density and high-density thiol compounds of varying molecular weight. The thiols are functionalized to the Au surface via a sulfide linkage. An exemplary process for surface functionalization may involve chemisorption of a sulfide species on an Au surface. A ligand may initial undergo low-density chemisorption on the Au surface, followed by heterogeneous island formation as the ligand density increases. As the process approaches completion, a high-density monolayer may be formed on the surface.

Surface functionalizations, surface passivations and other deposited species may undergo additional processing to alter their surface coverage, enhance or improve bonding of surface species, or remove non- or poorly-bonded surface species. In some configurations, a substrate may be immersed in a solvent for some amount of time after deposition of a functionalization, passivating group or other species. Exemplary solvents may include water, alcohols such as methanol and ethanol, organic solvents (e.g., acetone, MEK, DMF, and THF), mineral acids or bases (e.g., NaOH, KOH, HCl, $H_2SO_4$, $HNO_3$) organic acids (e.g., acetic acid), or combinations thereof. A substrate treated with a solvent may be subject to additional mechanical action by the fluid, such as flowing, mixing, sonication, spraying, or jet impingement. Treatment of a substrate after a deposition process may occur for a particular time period, such as about 1 minute (min), 30 mins, 1 hour (hr), 3 hrs, 6 hrs, 12 hrs, 1 day, 2 days, 3 days, 4 days, 5 days, 6 days, or 1 week. Treatment of a substrate after a deposition process may occur for at least about 1 minute (min), 30 mins, 1 hr, 3 hrs, 6 hrs, 12 hrs, 1 day, 2 days, 3 days, 4 days, 5 days, 6 days, or 1 week or more. Alternatively or additionally, treatment of a substrate after a deposition process may occur for no more than about 1 week, 6 days, 5 days, 4 days, 3 days, 2 days, 1 day, 12 hrs, 6 hrs, 3 hrs, 1 hr, 30 mins, 1 min or less. In some configurations, a substrate may be subjected to multiple solvent treatments after a deposition process (e.g., aqueous immersion followed by organic solvent immersion). In some configurations, a substrate may be dried by heat and/or vacuum after a solvent treatment. Substrates may undergo subsequent rounds of deposition of a surface functionalization, surface passivation, or other deposited species after a solvent treatment.

A fluidic device may comprise one or more functional areas. A functional area may be a region where a function of the device occurs. Exemplary fluidic device functions may include fluid transfer, mixing, reaction, separation, capture, immobilization, reaction, assay, detection, and disposal. The surface of a functional area may be functionalized with a specific surface chemistry that enhances or enables the function of that region of the fluidic device.

Figure 10A:
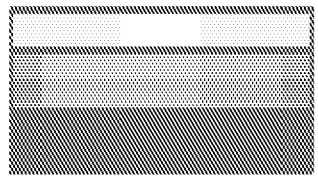
FIG. 10A illustrates stages of an etchless process of applying multiple surface functionalizations to a substrate, in accordance with some embodiments.
Figure 10A:
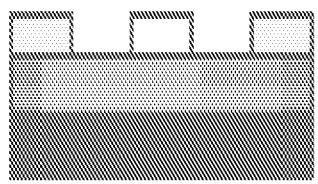
Figure 10A:
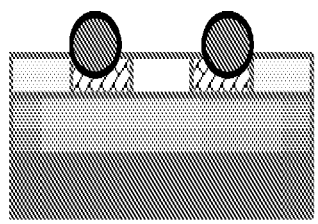
Figure 10A:
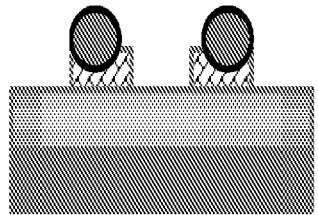
Figure 10A:
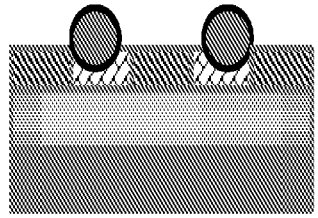

FIGS. 10A-10D show, in an aspect, exemplary methods for preparing a functional patterned surface on a substrate. FIG. 10A depicts a method of forming a patterned surface without an etching step. In a first step a), a metal- or metal oxide- (e.g., Au or $ZrO_2$) coated substrate (e.g., fused silica) is coated with a resist material (e.g., a photoresist). In a second step b), the photoresist material is patterned to reveal areas of the metal or metal oxide surface. In a third step c), the exposed metal or metal oxide surface is functionalized with a group such as a capture or binding agent or group. In a fourth step d), the resist material is removed to reveal non-functionalized portions of the metal or metal oxide surface. In a step e), the exposed metal or metal oxide surface is functionalized with another surface chemistry such as a passivating group or a blocking group. The method depicted in FIG. 10A can also be performed with a resist directly on the substrate using substrate-specific functionalization chemistries.

Figure 10B:
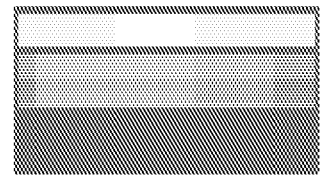
FIG. 10B illustrates stages of a first etching process of applying multiple surface functionalizations to a substrate, in accordance with some embodiments.
Figure 10B:
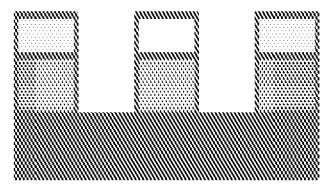
Figure 10B:
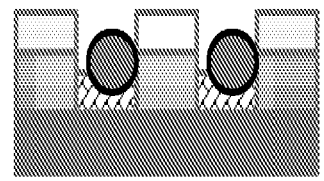
Figure 10B:
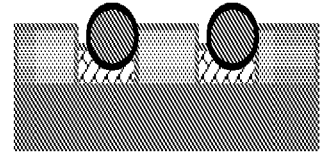
Figure 10B:
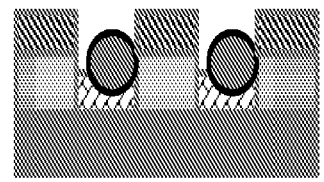

FIG. 10B depicts a method of forming a patterned surface with an etching step. In a first step a), a metal- or metal oxide- (e.g., Au or $ZrO_2$) coated substrate (e.g., fused silica) is coated with a resist material (e.g., a photoresist). In a second step b), the photoresist material is patterned then etched by an etching method (e.g. HF etch) to reveal areas of the substrate. In a third step c), the exposed substrate surface is functionalized with a group such as a capture or binding agent or group. In a fourth step d), the resist material is removed to reveal non-functionalized portions of the metal or metal oxide surface. In a step e), the exposed metal or metal oxide surface is functionalized with another surface chemistry such as a passivating group or a blocking group. The method depicted in FIG. 10A can also be performed with a resist directly on the substrate using substrate-specific functionalization chemistries.

Figure 10C:
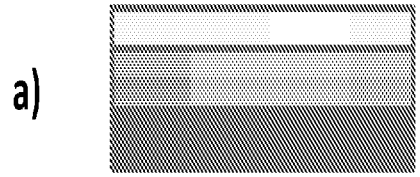
FIG. 10C illustrates stages of a second etching process of applying multiple surface functionalizations to a substrate, in accordance with some embodiments.
Figure 10C:
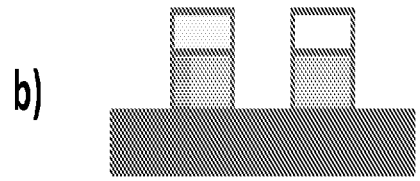
Figure 10C:
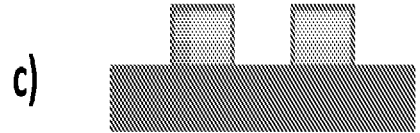
Figure 10C:
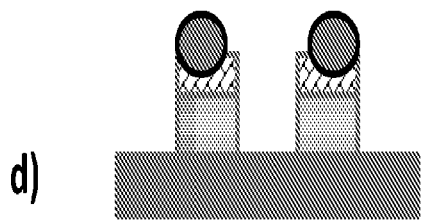
Figure 10C:
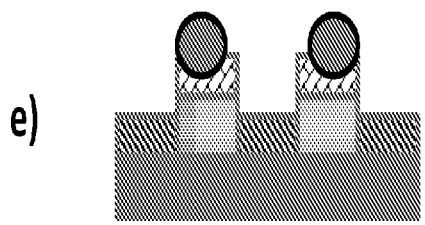

FIG. 10C depicts a second method of forming a patterned surface with an etching step. In a first step a), a metal- or metal oxide- (e.g., Au or $ZrO_2$) coated substrate (e.g., fused silica) is coated with a resist material (e.g., a photoresist). In a second step b), the resist material is patterned then etched by an etching method (e.g. HF etch) to reveal areas of the substrate. In a third step c), the photoresist material is removed, exposing the metal or metal oxide surface. In a fourth step d), the exposed metal or metal oxide surface is functionalized with a group such as a capture or binding agent or group using a metal or metal oxide-specific chemistry. In a fifth step e), the exposed substrate surface is functionalized with another surface chemistry such as a passivating group or a blocking group using a substrate-specific chemistry. Due to the specificity of the surface functionalization chemistries used, the substrate and metal or metal oxide surfaces can be functionalized in a order.

Figure 10D:
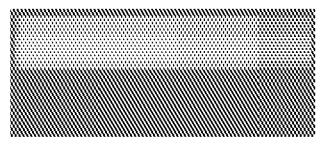
FIG. 10D illustrates stages of a lift off process of applying multiple surface functionalizations to a substrate, in accordance with some embodiments.
Figure 10D:
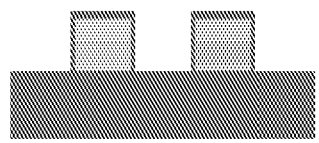
Figure 10D:
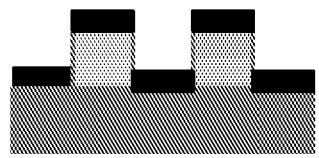
Figure 10D:
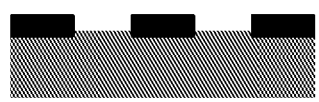
Figure 10D:
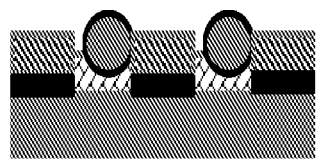

FIG. 10D depicts a lift-off method for forming a patterned surface. In a first step, a), a substrate is coated with a sacrificial coating (e.g., a photoresist). In a second step b), the sacrificial coating is patterned by a method to reveal areas of substrate. In a third step c), the sacrificial coating and exposed substrate are coated in a layer of a second coating (e.g., a metal or metal oxide). In a fourth step d), the sacrificial coating is removed by a particular technique, thereby removing at least a fraction of the second coating deposited on the sacrificial coating. The second coating remaining may be that which was deposited on the exposed substrate. In a fifth step e), the patterned substrate may be modified based upon the specific surface pattern as described above, for example, blocking groups or passivating groups functionalized to surfaces comprising the second coating and capture agents functionalized or conjugated to the exposed substrate surfaces.

A substrate may be coated with a surface deposit of a metal or metal oxide (e.g. $ZrO_2$) over some or all of its surface area. After metal deposition, a photoresist layer may be applied to a metal-coated substrate surface and patterned. An etching process may optionally be performed on a substrate with a patterned photoresist layer (e.g. hydrofluoric acid wet etching or dry etch). One or more optional cleaning steps may be performed between each process step. After photoresist patterning and optional etching, a substrate may be functionalized by a chosen functionalization or passivation chemistry that adds ligands or passivation groups to exposed regions of substrate. After functionalization or passivation, the photoresist layer may be removed, exposing fresh, non-functionalized or non-passivated substrate material. After photoresist removal, a second chosen functionalization or passivation step may be performed on regions of the substrate that were previously masked by the photoresist.

A functional area may be blocked with a blocking molecule or blocking group. Blocking may be performed at different stages; for example: blocking with HMDS to prevent surface binding, blocking with APTMS or APTES after linking of capture agents, etc A blocking molecule or blocking group may comprise a surface-bound molecule or group that physically limits other matter from contacting or adhering to a surface. A blocking molecule or group may physically limit contact with a surface by steric hindrance, electrostatic repulsion, magnetic repulsion, or other mechanisms. A blocking molecule or blocking group may exclude particular molecules from a surface based upon a chemical, electrical, or hydrodynamic property such as polarity, molecular weight, electrical charge, electronegativity, or hydraulic radius. In some configurations, a blocking group may prevent the adhesion of macromolecules such as polysaccharides, proteins, nucleic acids, or combinations thereof. A blocking molecule may prevent surface fouling by preventing the adhesion of cells or other particles. A blocking molecule or blocking group may exclude molecules from a surface with a molecular weight greater than about 100 Daltons (Da), 250 Da, 500 Da, 1 kiloDalton (kDa), 5 kDa, 10 kDa, 15 kDa, 20 kDa, 25 kDa, 30 kDa, 40 kDa, 50 kDa, 60 kDa, 70 kDa, 80 kDa, 90 kDa, 100 kDa or more.

A functional area may contain one or more regions of surface functionalizations or ligands that enhances or increases adhesion or binding of molecules at the surface. A surface functionalization or ligand may comprise a binding or capture agent or associated ligand, e.g., streptavidin or biotin. A surface functionalization or ligand may comprise a reactive group configured to form a bond with another molecule or group, e.g., click chemistry (see, for example, U.S. Pat. Nos. 6,737,236 and 7,427,678, each incorporated herein by reference in its entirety); azide alkyne Huisgen cycloaddition reactions, which use a copper catalyst (see, for example, U.S. Pat. Nos. 7,375,234 and 7,763,736, each incorporated herein by reference in its entirety); Copper-free Huisgen reactions ("metal-free click") using strained alkynes or triazine-hydrazine moieties which can link to aldehyde moieties (see, for example, U.S. Pat. No. 7,259,258, which is incorporated by reference); triazine chloride moieties which can link to amine moieties; carboxylic acid moieties which can link to amine moieties using a coupling reagent, such as EDC; thiol moieties which can link to thiol moieties; alkene moieties which can link to dialkene moieties that are coupled through Diels-Alder reactions; and acetyl bromide moieties which can link to thiophosphate moieties (see, for example, WO 2005/065814, which is incorporated by reference). A functional area may comprise functional groups that are configured to react via a click reaction (e.g., metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norborene cycloaddition, oxanobornadiene cycloaddition, tetrazine ligation, tetrazole photoclick reactions). Exemplary silane-derivative CLICK reactants may include alkenes, alkynes, azides, epoxides, amines, thiols, nitrones, isonitriles, isocyanides, aziridines, activated esters, and tetrazines (e.g., dibenzocyclooctyne-azide, methyltetrazine-transcyclooctylene, epoxide-thiol, etc.). A click reaction may provide an advantageous method of rapidly forming a bond under benign conditions (e.g., room temperature, aqueous solvents). In some configurations, silane derivatives may be substituted for comparable phosphate or phosphonate derivatives as appropriate. A functional area may be functionalized with a particular ligand to bind or capture a specific type of molecule. In some configurations, a surface may be functionalized to selectively bind or capture a biomolecule, e.g., a nucleic acid molecule, a structured nucleic acid particle, or a protein.

A functional area of a fluidic component may contain regions comprising two or more types of surface functionalizations or ligands. Multiple surface ligands may be used in a single region to create more than one property or functionality at the particular region of the surface. For example, a single region may contain both binding agents and blocking groups to create highly-localized capture sites while preventing adhesion over the rest of a region of a surface. The multiple surface functionalizations or ligands applied to a particular region of the surface may be distinguished by differing chemical composition of a pendant side chain or side group. For example, a particular region of the surface may be functionalized with ligands containing non-reactive side groups and ligands containing reactive side groups. The reactive side groups would permit further modification of the surface by reaction with surface-bound reactive ligands. Regions of the surface functionalized with multiple types of ligands may contain the two or more ligands at a particular ratio. The ratio of differing ligands on a surface may be varied to optimize the surface density of particular chemical groups on the surface (e.g., 1 blocking group per a certain surface area of the blocked surface). A first surface-bound ligand may have a ratio to a second surface-bound ligand of about 1,000,000:1, 100,000:1, 10,000:1, 1,000:1, 100:1, 10:1 or 1:1. A first surface-bound ligand may have a ratio to a second surface-bound ligand of no more than about 1,000,000:1, 100,000:1, 10,000:1, 1,000:1, 100:1, 10:1 or 1:1 or less. A first surface-bound ligand may have a ratio to a second surface-bound ligand of at least about 1:1, 10:1, 100:1, 1,000:1, 10,000:1, 100,000:1, or 1,000,000:1 or more.

Fluidic Device Fabrication Methods

A fluidic device may be fabricated by joining two or more components. In some configurations, a fluidic device component may comprise one or more substrates that have been microfabricated or micropatterned on at least one surface. In some configuration, a fluidic device may comprise a first micropatterned substrate joined to a second non-patterned or non-fabricated substrate along a paired set of joining surfaces. In some configurations, one or more of the joining surfaces may comprise a coating such as Au or $ZrO_2$ to participate in a bonding process. In some configurations, one or more joining surfaces may comprise a functionalization or ligand to participate in a bonding process. Two or more components may be joined to form an enclosure that prevents or limits the transfer of fluid into or out of the fluidic device. In some configurations, a substrate may comprise a cover component. In some configurations, two or more components of a fluidic device may be aligned before, during or after a joining process.

A metal or metal oxide layer may be deposited over an entire surface on a fluidic component. A metal or metal oxide layer may be deposited in particular areas of a surface of a fluidic component. A metal or metal oxide layer may be deposited on regions where bonding between fluidic components may occur, such as the tops of pillars, ridges or platforms. Metal layers, metal oxide layers, or functionalized metal or metal oxide layers may be deposited as a cap on a pillar or other region of a fluidic component that facilitates bonding. Metal or metal oxide layers may be deposited on one or both components that may be joined by a bonding method. In some configurations, a functionalization or ligand (e.g., a silane, phosphate, or phosphonate compound) may be added to a substrate, metal or metal oxide surface to facilitate the joining of two components of a fluidic device A surface of a component in a fluidic device may be finished or prepared by a method that minimizes the roughness or camber of the component. In some configurations, a component surface may be polished to minimize surface roughness or camber. A surface on a component of a fluidic device may be characterized by an average surface roughness or camber. An average surface roughness may be defined as the average surface height deviation from the level of an ideal surface coincident to the level of the tallest surface feature. An average surface camber may be defined as the average deviation of a curved surface from the trace of an ideal curved surface. A surface may have an average roughness or camber of about 0.1 nanometers (nm), 0.5 nanometers nm, 1 nm, 1.5 nm, 2.0 nm, 2.5 nm, 3.0 nm, 3.5 nm, 4.0 nm, 4.5 nm, 5.0 nm, 6.0 nm, 7.0 nm, 8.0 nm, 9.0 nm, 10.0 nm, 20 nm, 30 nm, 50 nm or more. A surface may have an average roughness or camber of at least about 0.5 nanometers (nm), 1 nm, 1.5 nm, 2.0 nm, 2.5 nm, 3.0 nm, 3.5 nm, 4.0 nm, 4.5 nm, 5.0 nm, 6.0 nm, 7.0 nm, 8.0 nm, 9.0 nm, 10.0 nm, 20 nm, 30 nm, 50 nm or more. Alternatively or additionally, a surface may have an average roughness or camber of no more than about 50 nm, 30 nm, 20 nm, 10.0 nm, 9.0 nm, 8.0 nm, 7.0 nm, 6.0 nm, 5.0 nm, 4.5 nm, 4.0 nm, 3.5 nm, 3.0 nm, 2.5 nm, 2.0 nm, 1.5 nm, 1 nm, 0.5 nm, or less.

A surface roughness may be measured by a suitable method including mechanical methods, scanning probe methods, electrical methods, fluid methods, optical methods or electron microscopy methods. Exemplary methods may include taper-sectioning, light-sectioning, specular reflection, diffuse reflection, speckle patterning, optical interferometry, phase shift interferometry, scanning tunneling microscopy, atomic force microscopy, hydraulic methods, pneumatic gauging, capacitance methods, scanning electron microscopy, profilometry and electron backscattering. A chosen surface roughness or camber measurement method may have resolution to the nanoscale or atomic scale.

The bonding of components in a fluidic device may create a bond between components with an average thickness. An average thickness of a bond between components in a fluidic device may be about 1 Angstrom (Å), 5 Å, 1 nm, 5 nm, 10 nm, 20 nm, 30 nm, 40 nm, 50 nm, 100 nm, 200 nm, 300 nm, 400 nm, 500 nm, 1 micrometer (µm), 10 µm or more. An average thickness of a bond between components of a fluidic device may be at least about 1 Angstrom (Å), 5 Å, 1 nanometer (nm), 5 nm, 10 nm, 20 nm, 30 nm, 40 nm, 50 nm, 100 nm, 200 nm, 300 nm, 400 nm, 500 nm, 1 micrometer (µm), 10 µm or more. Alternatively or additionally, an average bond thickness between components in a fluidic device may be no more than about 10 µm, 1 µm, 500 nm, 400 nm, 300 nm, 200 nm, 100 nm, 50 nm, 40 nm, 30 nm, 20 nm, 10 nm, 5 nm, 1 nm, 5 Å, 1 Å or less.

The bond between components of a fluidic device may have a measurable strength. A bond strength may be measured in a suitable fashion, including tensile strength, yield strength, or shear strength. A bond strength may be measured based upon a normal stress or a shear stress. A bond between components of a fluidic device may have a measured strength of about 0.1 megaPascals (MPa), 0.2 MPa, 0.3 MPa, 0.4 MPa, 0.5 MPa, 0.6 MPa, 0.7 MPa, 0.8 MPa, 0.9 MPa, 1.0 MPa, 1.1 MPa, 1.2 MPa, 1.3 MPa, 1.4 MPa, 1.5 MPa, 1.6 MPa, 1.7 MPa, 1.8 MPa, 1.9 MPa, 2.0 MPa, 2.5 MPa, 3.0 MPa, 3.5 MPa, 4.0 MPa, 4.5 MPa, 5.0 MPa or more. A bond between components of a fluidic device may have a measured strength of at least about 0.1 MPa, 0.2 MPa, 0.3 MPa, 0.4 MPa, 0.5 MPa, 0.6 MPa, 0.7 MPa, 0.8 MPa, 0.9 MPa, 1.0 MPa, 1.1 MPa, 1.2 MPa, 1.3 MPa, 1.4 MPa, 1.5 MPa, 1.6 MPa, 1.7 MPa, 1.8 MPa, 1.9 MPa, 2.0 MPa, 2.5 MPa, 3.0 MPa, 3.5 MPa, 4.0 MPa, 4.5 MPa, 5.0 MPa or more. Alternatively or additionally, a bond between components of a fluidic device may have a bond strength of no more than about 5.0 MPa, 4.5 MPa, 4.0 MPa, 3.5 MPa, 3.0

MPa, 2.5 PA, 2.0 MPa, 1.9 MPa, 1.8 MPa, 1.7 MPa, 1.6 MPa, 1.5 MPa, 1.4 MPa, 1.3 MPa, 1.2 MPa, 1.1 MPa, 1.0 MPa, 0.9 MPa, 0.8 MPa, 0.7 MPa, 0.6 MPa, 0.5 MPa, 0.4 MPa, 0.3 MPa, 0.2 MPa, 0.1 MPa or less.

Other mechanical characteristics of a bond formed between two components of a fluidic device may be measured. The bond between components of fluidic device may have a measurable elongation or strain due to a deformation stress. An elongation or strain due to a deformation stress may be measured when a shear stress or a normal stress is applied. A bond between two components of a fluidic device may also be characterized by other properties such as elasticity, compressibility, hardness, toughness, thermal expansion, malleability, and resilience.

Two or more components of a fluidic device may be joined or bonded at a particular bonding temperature. In some configurations, the temperature may be minimized at which a bond is formed to limit the formation, alteration or deposition of chemical species or active sites that may inhibit the function of the fluidic device. In some configurations, the temperature may be minimized at which a bond is formed to limit formation of stress between the components due to different thermal expansion coefficients. A bond between two or more components of a fluidic device may be formed at a temperature of about 0° C., 10° C., 20° C., 30° C., 40° C., 50° C., 60° C., 70° C., 80° C., 90° C., 100° C., 110° C., 120° C., 130° C., 140° C., 150° C., or more. A bond between two or more components of a fluidic device may be formed at a temperature of at least about 0° C., 10° C., 20° C., 30° C., 40° C., 50° C., 60° C., 70° C., 80° C., 90° C., 100° C., 110° C., 120° C., 130° C., 140° C., 150° C., or more. Alternatively or additionally, a bond between two or more components of a fluidic device may be formed at a temperature of no more than about 150° C., 140° C., 130° C., 120° C., 110° C., 100° C., 90° C., 80° C., 70° C., 60° C., 50° C., 40° C., 30° C., 20° C., 10° C., 0° C., or less. In some configurations, a bonding method may cycle between two or more temperatures.

Two or more components may be joined or bonded in the presence of a fluid medium. The fluid medium may comprise one or more reagents that enhance or facilitate the joining or bonding. A fluid medium for a joining or bonding of fluidic device components may comprise catalysts, reactants, salts, or buffers. A fluid medium may be configured to facilitate or enhance a specific joining or bonding reaction, such as a click reaction, nucleophilic substitution reaction, or electrophilic substitution reaction. A fluid medium may be an aqueous fluid. Two or more components of a fluidic device may be joined or bonded at a particular pH. In some configurations, the two or more components may be joined or bonded in the presence of a fluid medium with a particular pH. Two or more components of a fluidic device may be joined or bonded at an acidic pH. Two or more components of a fluidic device may be joined or bonded at a basic pH. In some configurations, two or more components may be joined or bonded at a neutral or near-neutral pH (e.g., pH 6.5-7.5). Two or more components of a fluidic device may be joined or bonded at a pH of about 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, or about 14.0. Two or more components of a fluidic device may be joined or bonded at a pH of at least about 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0 or greater than 14.0. Alternatively or additionally, two or more components of a fluidic device may be joined or bonded at a pH of no more than about 14.0, 13.9, 13.8, 13.7, 13.6, 13.5, 13.4, 13.3, 13.2, 13.1, 13.0, 12.9, 12.8, 12.7, 12.6, 12.5, 12.4, 12.3, 12.2, 12.1, 12.0, 11.9, 11.8, 11.7, 11.6, 11.5, 11.4, 11.3, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, or less than 0.

Joining or bonding between two or more components of a fluidic device may occur within a certain time. Two or more components of a fluidic device may be joined or bonded for at least about 1 second (s), 30 s, 45 s, 1 minute (min), 5 mins, 10 mins, 15 mins, 30 mins, 45 mins, 1 hour (hr), 3 hrs, 6 hrs, 9 hrs, 12 hrs, 15 hrs, 18 hrs, 21 hrs, 1 day, 2 days, 3 days, 1 week, or more than 1 week. Alternatively or additionally, two or more components of a fluidic device may be joined or bonded for no more than about 1 week, 3 days, 2 days, 1 day, 21 hrs, 18 hrs, 15 hrs, 12 hrs, 9 hrs, 6 hrs, 3 hrs, 1 hr, 45 mins, 30 mins, 15 mins, 10 mins, 5 mins, 1 min, 45 s, 30 s, 1 s, or less than 1 s.

Two or more joined or bonded components of a fluidic device may be stable for a particular amount of time. Stability may be defined as withstanding standard operations (e.g., fluid transfers, mechanical handling, cleaning, rinsing, drying) without disruption of the joining or bonding between the two or more components. Two or more joined or bonded components of a fluidic device may be stable for at least about 1 day, 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 4 years, 5 years, or more than 5 years. Two or more joined or bonded components of a fluidic device may be stable for at least about 5 year, 4 years, 3 years, 2 years, 1 year, 11 months, 10 months, 9 months, 8 months, 7 months, 6 months, 5 months, 4 months, 3 months, 2 months, 1 month, 4 weeks, 3 weeks, 2 weeks, 1 week, 1 day, or less than 1 day.

Two or more components of a fluidic device may be joined or bonded with an exerted force. For example, two or more components may be joined or bonded while a pressure is exerted on surfaces or one or more of the components. In some configurations, a pressure may be even exerted over an entire surface. An exerted pressure or force may comprise a compressional pressure or force. The compressional pressure or force may result from the creation of vacuum between the components. Two or more components of a fluidic device may be joined or bonded by applying vacuum to the interstitial space between components while the external regions of the components are at ambient pressure or above.

Two or more components of a fluidic device may be joined or bonded by a surface-linked adhesive method. A fluidic device may comprise a first component and a second component with one or more overlapping regions of surface-linked bonding chemistries. In some configurations, both components may have matched patterning of surface-linked bonding chemistries so that the contact between bonding surfaces is maximized when the components are properly aligned. In other configurations, one component may have selective patterning of a surface-linked bonding chemistry while another component may have a generalized coverage of a complementary surface-linked bonding chemistry such that bonding between components is effective even with poor alignment.

Figure 14A:
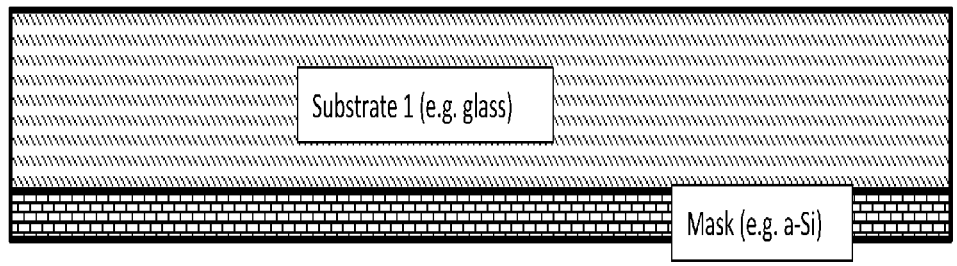
FIG. 14A depicts the first step of an embodiment of a low-temperature fluidic device bonding process, in accordance with some embodiments.
Figure 14B:
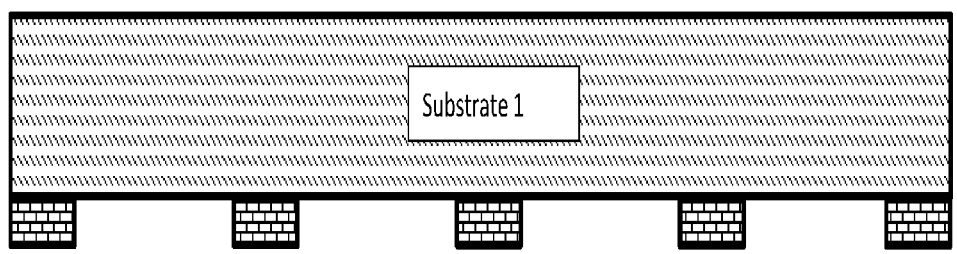
FIG. 14B depicts the second step of an embodiment of a low-temperature fluidic device bonding process, in accordance with some embodiments.
Figure 14C:
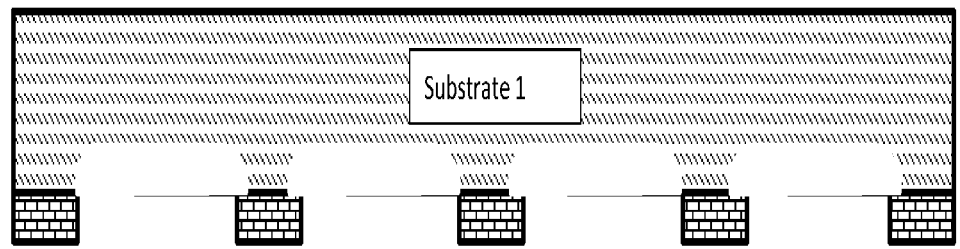
FIG. 14C depicts the third step of an embodiment of a low-temperature fluidic device bonding process, in accordance with some embodiments.
Figure 14D:
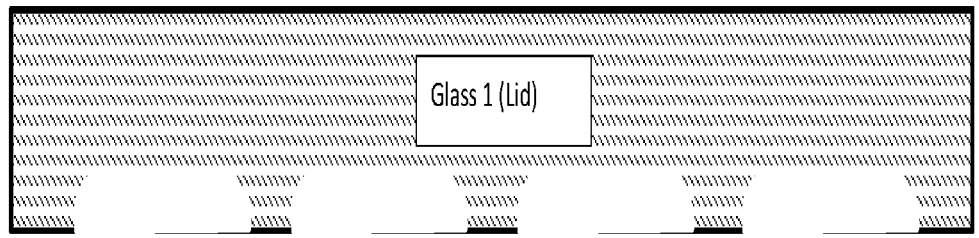
FIG. 14D depicts the fourth step of an embodiment of a low-temperature fluidic device bonding process, in accordance with some embodiments.
Figure 14E:
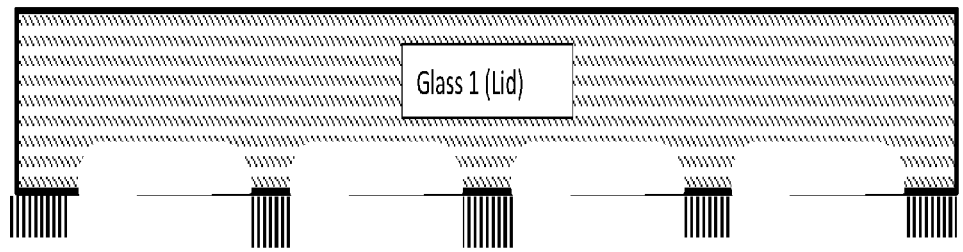
FIG. 14E depicts the fifth step of an embodiment of a low-temperature fluidic device bonding process, in accordance with some embodiments.
Figure 14F:
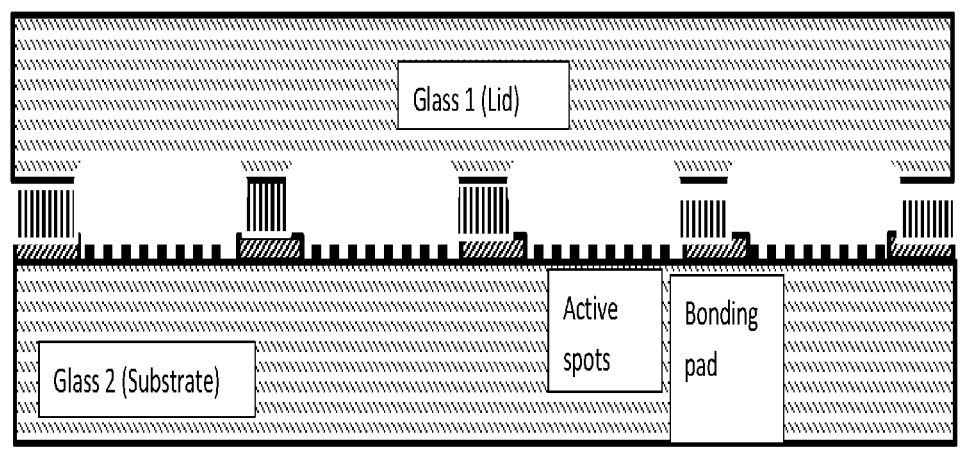
FIG. 14F depicts the sixth step of an embodiment of a low-temperature fluidic device bonding process, in accordance with some embodiments.
Figure 15A:
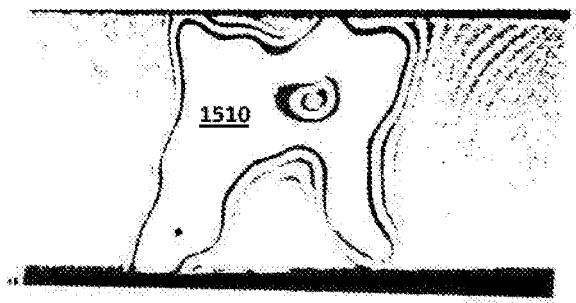
FIG. 15A shows two joined substrates immediately after a bonding process, in accordance with some embodiments.
Figure 15B:
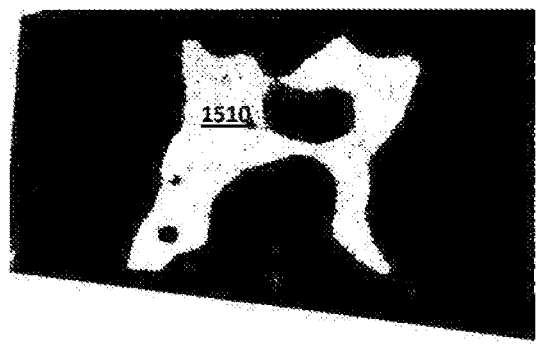
FIG. 15B shows two joined substrates 7 days after a bonding process, in accordance with some embodiments.
Figure 15C:
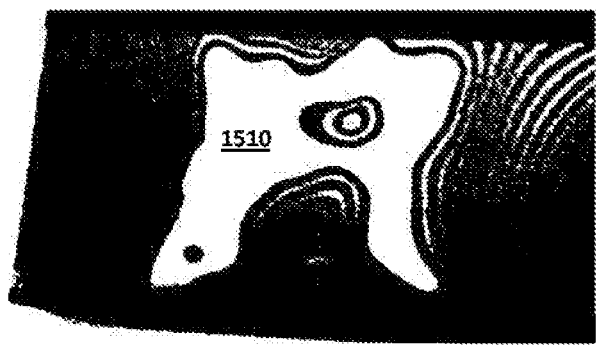
FIG. 15C shows two joined substrates 14 days after a bonding process, in accordance with some embodiments.
Figure 15D:
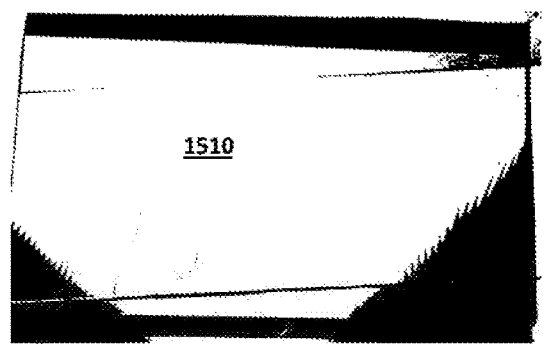
FIG. 15D shows two joined substrates 422 days after a bonding process, in accordance with some embodiments.

FIGS. 14A-14F depict a method for fabricating a fluidic device using a low-temperature bonding method. FIG. 14A depicts a cross-sectional view of a substrate (e.g., glass) with a deposited surface mask (e.g., amorphous silicon or polycrystalline silicon). FIG. 14B depicts a cross-sectional view of the same substrate after regions of the mask have been selectively removed to re-expose regions of the substrate surface. The mask material may be removed by a combination of methods such as lithography or dry etch. FIG. 14C shows a cross-sectional view of the substrate after it has been etched to selectively remove material not covered by the mask. The etching may be performed by a method such as HF wet etching. FIG. 14D depicts a cross-sectional view of the patterned and etched substrate after the mask material has been removed. FIG. 14E shows a cross-sectional view of the substrate after a surface-bound ligand has been locally functionalized to the surface (e.g., a catechol-terminated silane). FIG. 14F illustrates the bonding of the patterned substrate to a second patterned substrate. In this exemplary configuration, the second patterned substrate may comprise regions of metal or metal oxide coated pads, or functionalized pads, that match with the elevated features of the first substrate. Metal, metal oxide, or functionalized pads may be configured to form a bond with surface ligands of a first substrate. The second substrate may be patterned with active sites in the regions between the bonding pads. The active sites may serve as binding sites for capture agents in some configurations.

A surface-linked bonding chemistry may comprise a surface functionalization or ligand that is covalently-bound to the surface of a fluidic device component and that comprises a reactive group that is configured for reaction with another reactive group. In some configurations, the surface-bound functionalizations or ligands may comprise an organic chain and a reactive group. In some configurations, the functionalizations or ligands may comprise more than one organic chain or reactive group. The organic chains may be prepared in a suitable length for a chosen application. The organic chains may be chosen for specific chemical properties such as surface energy, steric size, amphipathicity, hydrophobicity or hydrophilicity. The organic chains may include heteroatoms (e.g., O, S, N). Exemplary organic chains may include, but are not limited to, alkane chains (i.e. —($CH_2$—$CH_2$)$_n$—), and polyethylene glycol chains (i.e. —(O—$CH_2$—$CH_2$)$_n$—). An organic chain may have a chain length determined by a particular number of atoms bonded along the chain length. An organic chain may have a chain length of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 atoms. An organic chain may have a chain length of at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 or more atoms. Alternatively or additionally, an organic chain may have a chain length of no more than about 100, 95, 90, 85, 80, 75, 70, 65, 60, 55, 50, 49, 48, 47, 46, 45, 44, 43, 42, 41, 4039, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or less atoms.

Figure 8:
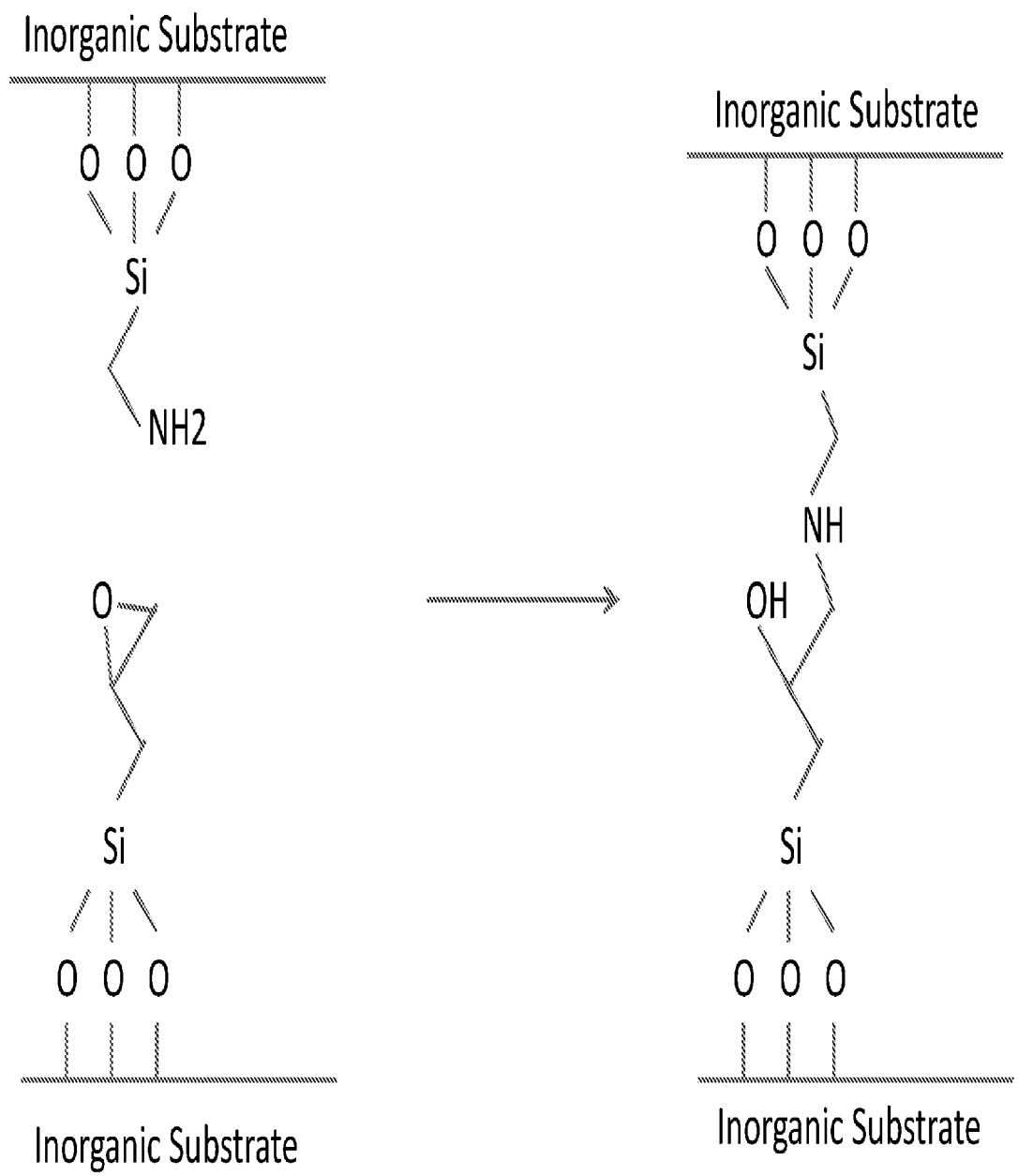
FIG. 8 illustrates a bonding chemistry for joining two silanated substrates, in accordance with some embodiments.

In some configurations, a surface-linked bonding chemistry may comprise reactive groups such as electrophilic groups or nucleophilic groups. A fluidic device component comprising a surface-linked electrophilic group may be configured to bond with a fluidic device component comprising a surface-linked nucleophilic group when functionalized surfaces are brought in contact. In some configurations, the surface-bound functionalizations or ligands may comprise silanes, organosilanes, silane derivatives, phosphate, phosphonates, or other suitable chemistries. In some configurations, the surface-bound functionalization or ligand may comprise an epoxidated organosilane, an aminated organosilane, an epoxidated organosilane, a mercaptosilane, an epoxidated phosphonate or phosphate, an aminated phosphonate or phosphate, or a mercaptophosphonate or mercaptophosphate. In some configurations, two inorganic surfaces may be functionalized with silane derivatives that are configured to react via a click reaction (e.g., metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2]cycloaddition, [4+1] cycloaddition, nucleophilic substitution, dihydroxylation, thiol-yne reaction, photoclick, nitrone dipole cycloaddition, norborene cycloaddition, oxanobornadiene cycloaddition, tetrazine ligation, tetrazole photoclick reaction). Exemplary silane-derivative click reactants may include alkenes, alkynes, azides, epoxides, amines, thiols, nitrones, isonitriles, isocyanides, aziridines, activated esters, and tetrazines (e.g., dibenzocyclooctyne-azide, methyltetrazine-transcyclooctylene, epoxide-thiol, etc.). A click reaction may provide an advantageous method of rapidly forming a bond under benign conditions (e.g., room temperature, aqueous solvents). In some configurations, silane derivatives may be substituted for comparable phosphate or phosphonate derivatives. FIG. 8 shows an exemplary bonding chemistry for two inorganic surfaces functionalized with silane derivatives. A bond may be formed by nucleophilic attack of the amine on the electrophilic epoxy group. Subsequent reactions (e.g., secondary amine reactions) may further strengthen the bond between surface-bound ligands. Other nucleophilic functional groups may include alcohols, thiols, carboxylates, and phenols. Other electrophilic functional groups may include alkyl halides, ketones, and unsaturated hydrocarbons (e.g., vinyl groups). The proposed method anticipates methods of bond formation between two functional groups or molecules. Methods of bond formation at low temperature or under chemically benign (e.g., aqueous solvents) conditions may be advantageous for forming fluidic devices with minimal surface deposition or contamination.

Two or more components may be brought into contact to form a bond via a surface-linked adhesive bonding chemistry. Optionally, two or more components may be aligned before a bond is formed. The alignment may be based on aligning surface edges of the components or aligning other features of the two or more components. A bond may be formed by a surface-linked bonding chemistry in a reaction condition that is suitable for the specific bonding chemistry employed. A surface-linked bonding chemistry may be utilized in liquid-phase or gas-phase conditions. A surface-linked bonding chemistry may be utilized under acidic or basic conditions. A surface-linked bonding chemistry may be utilized in the presence of one or more catalysts. Pressure may be applied during formation of a bond between two or more components of a fluidic device.

A surface-linked adhesive bonding chemistry may be modified to increase a strength of a bond between two surfaces. In some configurations, two joinable surfaces may not be optimally configured for maximal bonding strength due to surface mismatches or incongruities caused by surface roughness or camber on one or more of the contacted surfaces. In some configurations, bonding may be limited to the areas of closest contact between the two contacted surfaces. In some configurations, the bonding chemistry may be modified to increase a bond strength when two surfaces are contacted.

Figure 5:
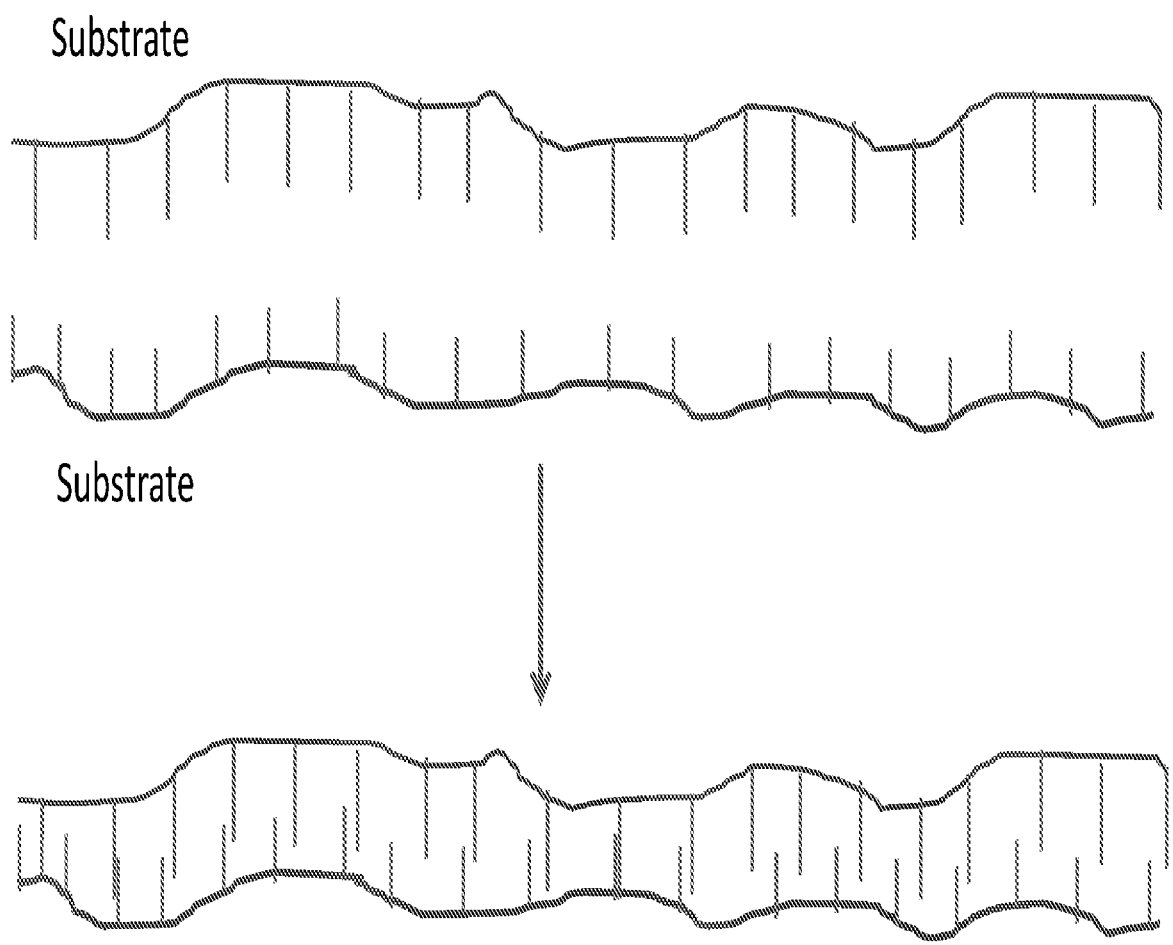
FIG. 5 shows a process of joining two functionalized surfaces when both surfaces have some degree of surface roughness using extended chain lengths, in accordance with some embodiments.

A bond strength may be increased by the functionalization of component surfaces with ligands that comprise long and/or branched chains. The long or branched chains may increase a likelihood of a functional group or ligand bonding with a complementary functional group or ligand on an opposing or adjacent surface. In some configurations, a functional group or ligand may comprise an organic chain of sufficient length to exceed an average surface roughness or camber of the surface to which it is bound. In some configurations, a sum of the lengths of the complementary organic chains (i.e. the bonding pair) may be greater than a sum of the average surface roughnesses or cambers for two surfaces brought into contact to form a bond. FIG. 5 shows two surfaces brought into contact with surface functionalities of sufficient length to overcome the surface roughness of both surfaces.

Figure 6:
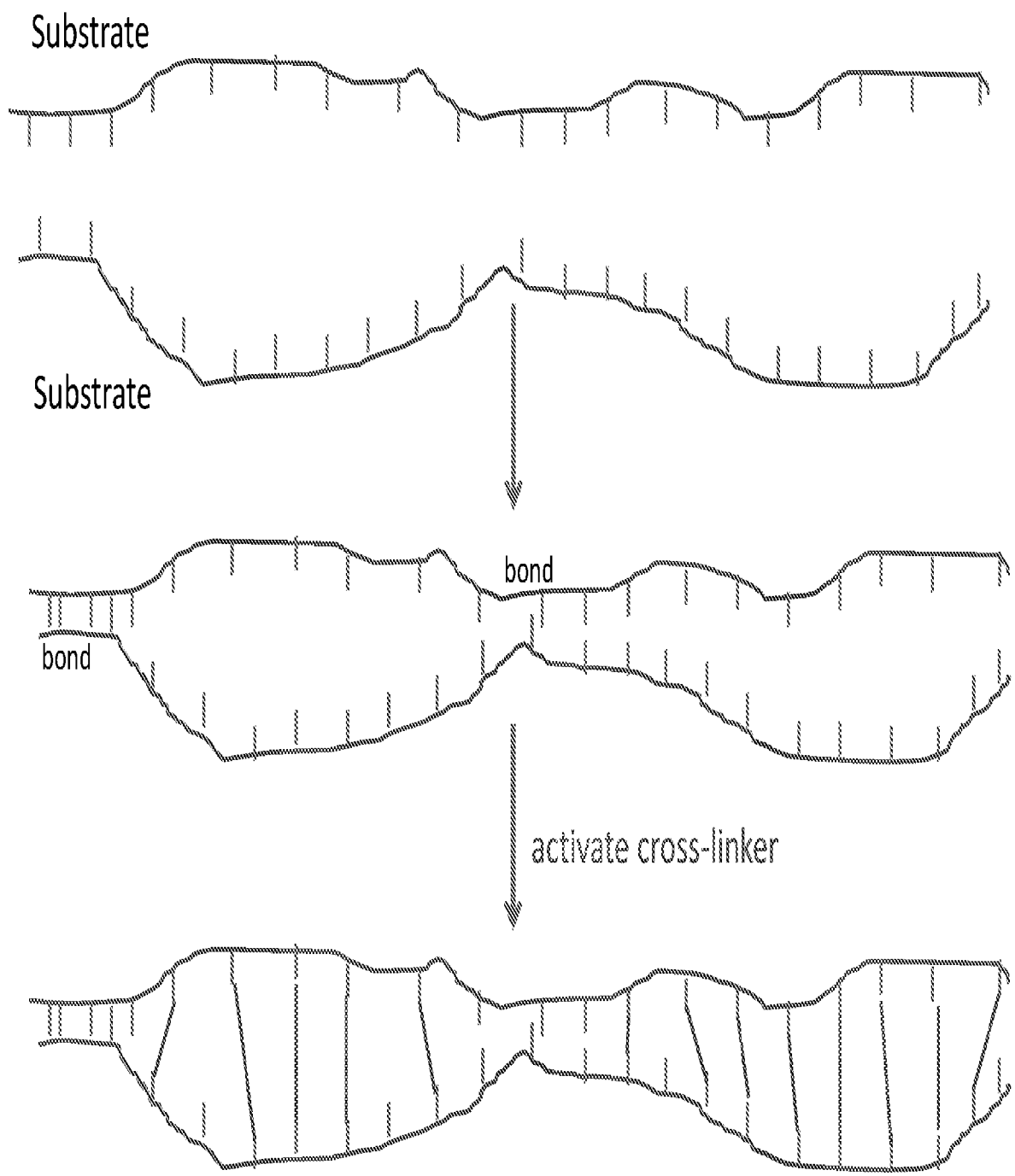
FIG. 6 depicts a process of joining two functionalized surfaces when both surfaces have some degree of surface roughness using a cross-linker, in accordance with some embodiments.

A bond strength may be increased by the use of one or more cross-linking molecules that complement the surface-linked adhesive bonding chemistry. The cross-linking molecule may comprise two or more reactive groups linked by organic chains. The reactive groups of the cross-linking molecule may be configured to react with the surface-linked functional groups or ligands. FIG. 6 shows a hypothetical schematic of bonding process utilizing a cross-linking molecule. A cross-linking molecule may be present at a particular time during a bonding reaction. In some configurations, the cross-linking molecule is present throughout the bonding process. In other configurations, the cross-linking molecule is injected into void spaces that are created by mismatches or incongruities between two contacted surfaces after an initial bond has been formed directly between functional groups or ligands on the two contacted surfaces. A cross-linking molecule may utilize the same or differing reactive chemistries than the functional groups or ligands bound directly to the surfaces. The cross-linking molecule may comprise an organic chain. The organic chain may be prepared in a suitable length for the chosen application. The organic chain may be chosen for specific chemical properties such as surface energy, steric size, amphipathicity, hydrophobicity or hydrophilicity. The organic chain may include heteroatoms (e.g., O, S, N). Exemplary organic chains may include, but are not limited to, alkane chains (i.e. $-(CH_2-CH_2)_n-$), and polyethylene glycol chains (i.e. $-(O-CH_2-CH_2)_n-$). An organic chain may have a chain length determined by a particular number of atoms bonded along the chain length. An organic chain may have a chain length of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 atoms. An organic chain may have a chain length of at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 or more atoms. Alternatively or additionally, an organic chain may have a chain length of no more than about 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or less atoms. A cross-linking chain may be branched or linear.

A surface-linked adhesive chemistry may be formed for a period of about 1 second (s), 20 s, 30 s, 1 minute (min), 10 min, 30 min, 1 hour (hr), or 5 hrs. A surface-linked adhesive chemistry may be formed for a period of at least about 1 s, 20 s, 30 s, 1 min, 10 min, 30 min, 1 hr, or 5 hrs or more. Alternatively or additionally, a surface-linked adhesive chemistry may be formed for no more than about 5 hours, 1 hour 30 min, 10 min, 1 min, 30 s, 20 s, or about 1 s or less.

Figure 7A:
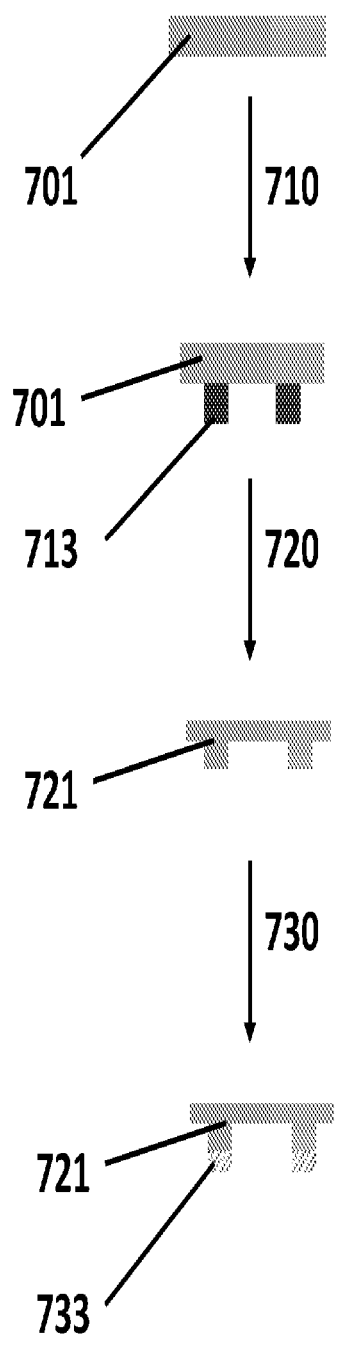
FIG. 7A shows a process for forming a fluidic component with channels for fluid flow, in accordance with some embodiments.
Figure 7B:
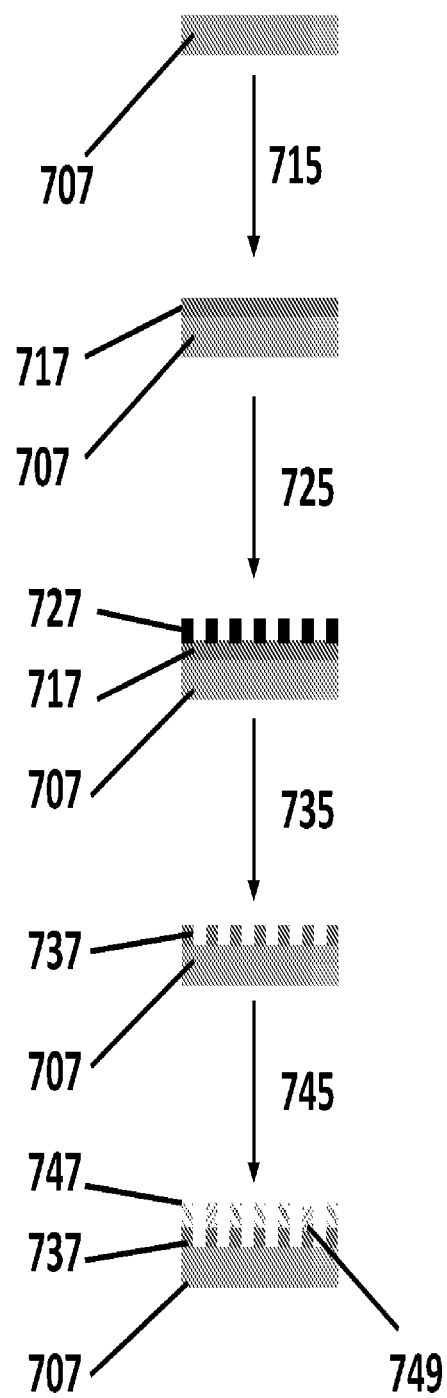
FIG. 7B shows a process for forming a fluidic component with a microarray of active sites, in accordance with some embodiments.
Figure 7C:
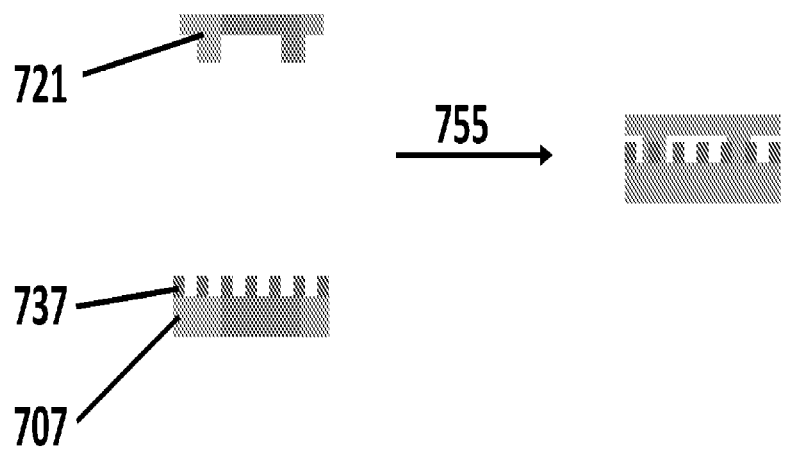
FIG. 7C shows a process of joining two fluidic components into a fluidic device using a joining method such as anodic bonding, in accordance with some embodiments.
Figure 7D:
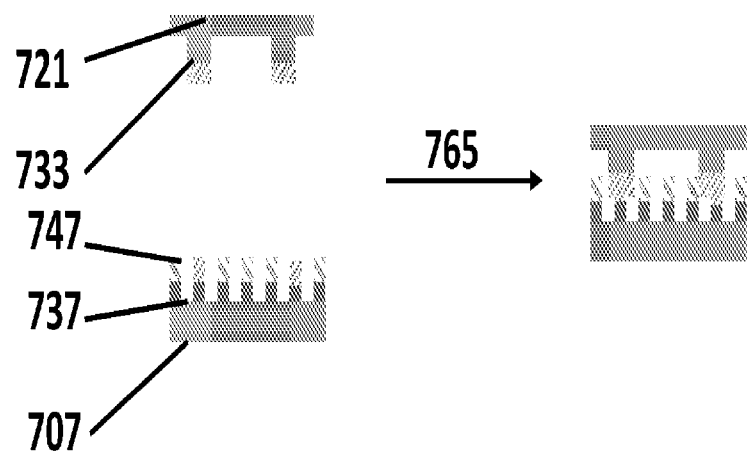
FIG. 7D shows a process of joining two fluidic components into a fluidic device using surface-bound adhesives, in accordance with some embodiments.

FIGS. 7A, 7B, and 7D depict methods for fabricating fluidic components and joining them via surface-bound adhesive method. FIG. 7A shows a first substrate 701 that is subjected to a masking and patterning process 710, resulting in patterned areas of masking agent 713 on the substrate 701. The patterned substrate 701 is then subjected to an etching process 720 followed by removal of the masking agent 713. The etched substrate 721 may then be functionalized with a surface-bound ligand 733 or other surface deposit. FIG. 7B shows a second substrate 707 that is coated with a deposited layer 717 such as a metal or metal oxide in a deposition process 715. A masking agent 727 is then deposited and patterned on the deposited layer 717 in a masking process 725. The exposed regions of the deposited layer 717 may be etched in an etching process 735, followed by removal of the masking agent 727, to create raised surfaces 737. The raised surfaces 737 may be functionalized with a adhesive ligand 747 or other surface deposit 749 (e.g., a capture agent) to create a patterned substrate with active sites for binding and adhesive sites for bonding to another fluidic component. FIG. 7C depicts a method of joining an etched fluidic component 721 from FIG. 7A with a second fluidic component. The fluidic components may be joined by a method such as anodic or eutectic bonding. FIG. 7D depicts a low-temperature adhesive method for joining two fluidic components using surface-bound ligands 733 and 749 that are configured to form covalent bonds with each other.

The described surface-linked bonding methods may apply to fluidic device components as well as non-fluidic components. The surface-linked bonding methods may be used to join two suitable inorganic surfaces, two suitable organic surfaces, or a combination thereof. Exemplary applications of the surface-linked bonding methods may include laminating polymer materials to glass materials for electronic devices (e.g., touchscreens) or joining together glass or other materials for non-fluidic applications (e.g., joining optical substrates).

Various other methods, such as anodic bonding, eutectic bonding, or fusion bonding may be used to join two or more fluidic components together. In an exemplary configuration, a fluidic may comprise two or more glass or borosilicate glass components that are to be joined at an interface between the two components. One or more of the components may be micromachined or fabricated with specific fluidic structures. One or more components of a fluidic device may comprise surfaces or regions with other surface chemistries, such as passivating or blocking chemistries. An interface between the components may comprise a point of contact between a pillar on an upper body and a surface on the lower body. A pillar may comprise a metal cap formed by the deposition of a metal or metal oxide, for example $ZrO_2$. The fluidic components may be brought in contact such that the metal cap of the upper body contacts the selected point of contact on the surface of the lower body. After the components are brought in contact, electrodes may be connected to the fluidic components. An electrical voltage or potential may be applied across the electrodes, initiating the formation of an anodic bond between the metal cap of the upper body and the surface of the lower body. In other configurations, the metal cap may be deposited on the surface of the lower body or the lower body may comprise the metal-capped pillar and the upper body may comprise a surface with a point of contact.

FIG. 7C depicts an exemplary process for joining a fluidic body with a lid component using anodic bonding. An upper lid piece may be formed via photolithography to create support pillars for the fluidic device. A lower body piece may be formed via atomic layer deposition of a $ZrO_2$ layer and photolithography to form a network of bonding sites across the surface of the body piece. The pieces may be brought into contact and joined via an anodic bonding process to create bonds where the bonding sites contact the support pillars.

Anodic bonding may occur at a particular voltage depending upon the materials chosen. Anodic bonding may occur at about 200 volts (V), 300 V, 400 V, 500 V, 750 V, 1000 V, 1250 V, or about 1500 V. Anodic bonding may occur at a voltage of at least about 250 volts (V), 500 V, 750 V, 1000 V, 1250 V, or about 1500 V. Alternatively or additionally, anodic bonding may occur at no more than about 1500 V, 1250 V, 1000 V, 750 V, 500 V, or 250 V or less. Anodic bonding and other bonding methods may occur at a maximum temperature of no more than about 600° C., 500° C., 450° C., 400° C., 350° C., 300° C., 250° C., or 200° C. Anodic bonding and other bonding methods may occur in air or a reduced oxygen environment. Anodic bonding may occur for a period of about 1 second (s), 20 s, 30 s, 1 minute (min), 2 min, 5 min, or about 10 min. Anodic bonding may occur for a period of at least about 1 s, 20 s, 30 s, 1 min, 2 min, 5 min, or about 10 min or more. Alternatively or additionally, anodic bonding may occur for no more than about 10 min, 5 min, 2 min, 1 min, 30 s, 20 s, or about 1 s or less. Anodic bonding may be followed by a subsequent surface functionalization or surface passivation method. For example, a bonded fluidic device may be functionalized with a phosphate or phosphonate group in functional areas and a silane group in field areas.

Fluidic device components may be joined by adhesion between a functionalized metal or metal oxide layer and a surface of another fluidic device component. In an exemplary configuration, a fluidic device may comprise two or more glass or borosilicate glass or fused silica components that are to be joined at an interface between the two components. One or more of the components may be micromachined or fabricated with specific fluidic structures. One or more of the components may comprise surfaces with different functionalities. For example, a fluidic device component may comprise a field area with a PEG-silane functionalization, an active area with a silane functionalization, and a bonding area comprising a pillar capped with a non-functionalized $ZrO_2$ deposit. Another fluidic device component may comprise a surface functionalized with a bioinspired functional group, e.g. a catechol-terminated silane. A catechol derivative may be anchored to a gold substrate deposited on a surface. An interface between the components may comprise a point of contact between a pillar on one fluidic device component and a surface on a second fluidic device component. The fluidic device components may be brought in contact such that the metal cap of a first component contacts the selected point of contact on the surface of a second component, creating adhesion between the functional groups on a first component and the $ZrO_2$ cap on a second component.

Bonding by adhesion between a functionalized material and a metal or metal oxide layer may occur under ambient conditions. In some configurations, the bonding method may be performed in an aqueous solution. For example, an adhesion group may be facilitated in the presence of a metal salt such as a zirconium salt solution. Adhesion bonding may occur for a period of about 1 s, 20 s, 30 s, 1 min, 10 min, 30 mins, 1 hour (hr), or 5 hrs. Adhesion bonding may occur for a period of at least about 1 s, 20 s, 30 s, 1 min, 10 min, 30 min, 1 hr, or 5 hrs or more. Alternatively or additionally, adhesion bonding may occur for no more than about 5 hours, 1 hour 30 min, 10 min, 1 min, 30 s, 20 s, or about 1 s or less.

Fluidic device components may be joined by the formation of a metal-phosphate framework between two or more fluidic device components. In an exemplary configuration, a fluidic device may comprise two or more glass or borosilicate glass or fused silica components that are to be joined at an interface between the two components. One or more of the components may be micromachined or fabricated with specific fluidic structures. One or more of the components may comprise surfaces with different functionalities. For example, a first fluidic device component may comprise a field area with a PEG-silane functionalization, an active area with a silane functionalization, and a bonding area comprising a pillar capped with a non-functionalized $ZrO_2$ deposit. A second fluidic device component may comprise a surface functionalized with a phosphate group or a metal oxide functionalized with phosphate groups. In some configurations, both surfaces may be covered with a phosphate deposit. Phosphate compounds may selectively bind to a metal or metal oxide surface. In some configurations, one or more surfaces may be further doped with metal ions, e.g. $Zr^{4+}$ ions. A metal-phosphate lattice may be formed by the coordination of phosphate groups on a zirconium oxide surface. An interface between the components may comprise a point of contact between a pillar on the first fluidic device component and a surface on the second fluidic device component. The fluidic device components may be brought in contact such that the metal cap of the first fluidic device component contacts the selected point of contact on the surface of the second fluidic device component. Pressure may be applied to the fluidic device components to create a metal-phosphate framework, thereby joining the components. The metal-phosphate may be formed in the presence of metal ions, such as solvated $Zr^{4+}$ ions.

Bonding by a metal-phosphate framework between a functionalized material and a metal or metal oxide layer may occur under ambient conditions. In some configurations, the bonding method may be performed in an aqueous solution. For example, a metal-phosphate framework may be facilitated in the presence of a metal salt such as a zirconium salt solution. A metal-phosphate framework may be formed for a period of about 1 s, 20 s, 30 s, 1 min, 10 min, 30 min, 1 hr, or 5 hrs. A metal-phosphate framework may be formed for a period of at least about 1 s, 20 s, 30 s, 1 min, 10 min, 30 min, 1 hr, or 5 hrs or more. Alternatively or additionally, a metal-phosphate framework may be formed for no more than about 5 hours, 1 hour 30 min, 10 min, 1 min, 30 s, 20 s, or about 1 s or less.

Fluidic devices may be fabricated by in a manner consistent with the surface chemistries provided above. In some configurations, a fluidic device may comprise one or more fabricated components. A fluidic device may be a fluidic or a microfluidic device. In some configurations, a fluidic device comprises at least two components that are joined by a bond between the components. The bond may be designed to meet a particular requirement such as bond strength and fluid permeability. In some configurations, a bond between fluidic components may be characterized as having no leakage or near-zero permeability.

In some configurations, a fluidic device may comprise at least two components where at least two components have been fabricated or structured to provide utility to the fluidic device. In other configurations, a fluidic device may comprise at least two components where one component has been fabricated or structured to provide utility to the fluidic device. In a particular configuration, a fluidic device may comprise a microfabricated substrate that is bonded to a second substrate that has not been fabricated or structured. Two or more fluidic components may be joined by a joining or bonding method described above. A fluidic comprising more than two components may be joined sequentially or simultaneously.

A fluidic device may comprise one or more components with surfaces that have been modified with surface chemistries for applications other than bonding to other fluidic components. Exemplary modifications include passivated surfaces, blocked surfaces, and binding surfaces. Additional surface chemistries may be added during a particular part of the fluidic device fabrication process. In some configurations, a fluidic device component may have one or more surfaces modified before other components are joined to the modified component. In other configurations, a fluidic device comprising multiple components may be joined before surfaces are modified by other chemistries. In other configurations, surface modification occurs both before and after bonding or joining of device components.

At a given step in a substrate formation or modification method, cleaning may be performed. An oxygen plasma cleaning and activation step may be performed. After a surface modification or deposition, portions of the chip manufacture may be lifted-off, such as using hot DMF. Further, a sonication step may be performed. The resulting chip may be used in flow cells for assessments of biological assays.

Flow Cell Systems

A protein characterization system of the present disclosure may include a fluidic device that provides the primary location for polypeptide characterization. The fluidic device may contain one or more substrates to which a plurality of polypeptides may be bound. A fluidic device may comprise a microfluidic device (e.g. having channels or other components that hold less than 1 ml of fluid) or a macrofluidic device (e.g. having channels or other components that hold 1 ml of fluid or more). A fluidic device may be provided to a protein characterization system with a plurality of polypeptides bound to the fluidic device, or a fluidic device may be provided to the polypeptide characterization system polypeptides provided thereafter.

Figure 18A:
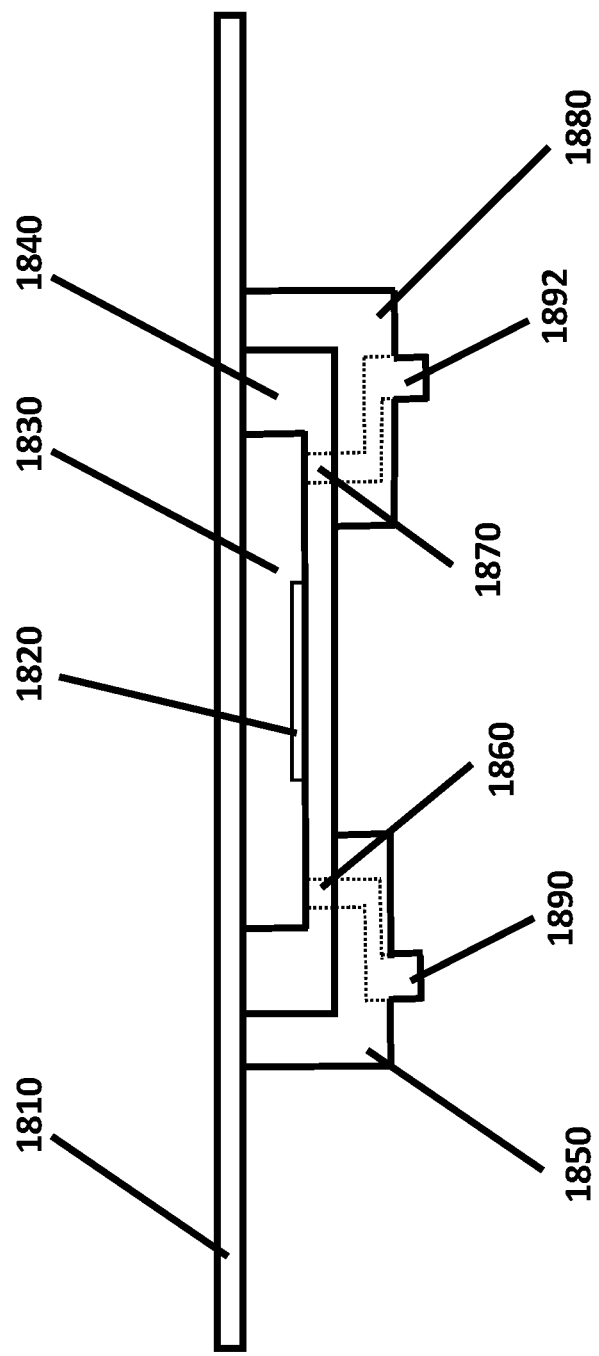
FIG. 18A shows a cross-sectional schematic of a fluidic device containing a substrate configured to display a plurality of peptides, in accordance with some embodiments.
Figure 18B:
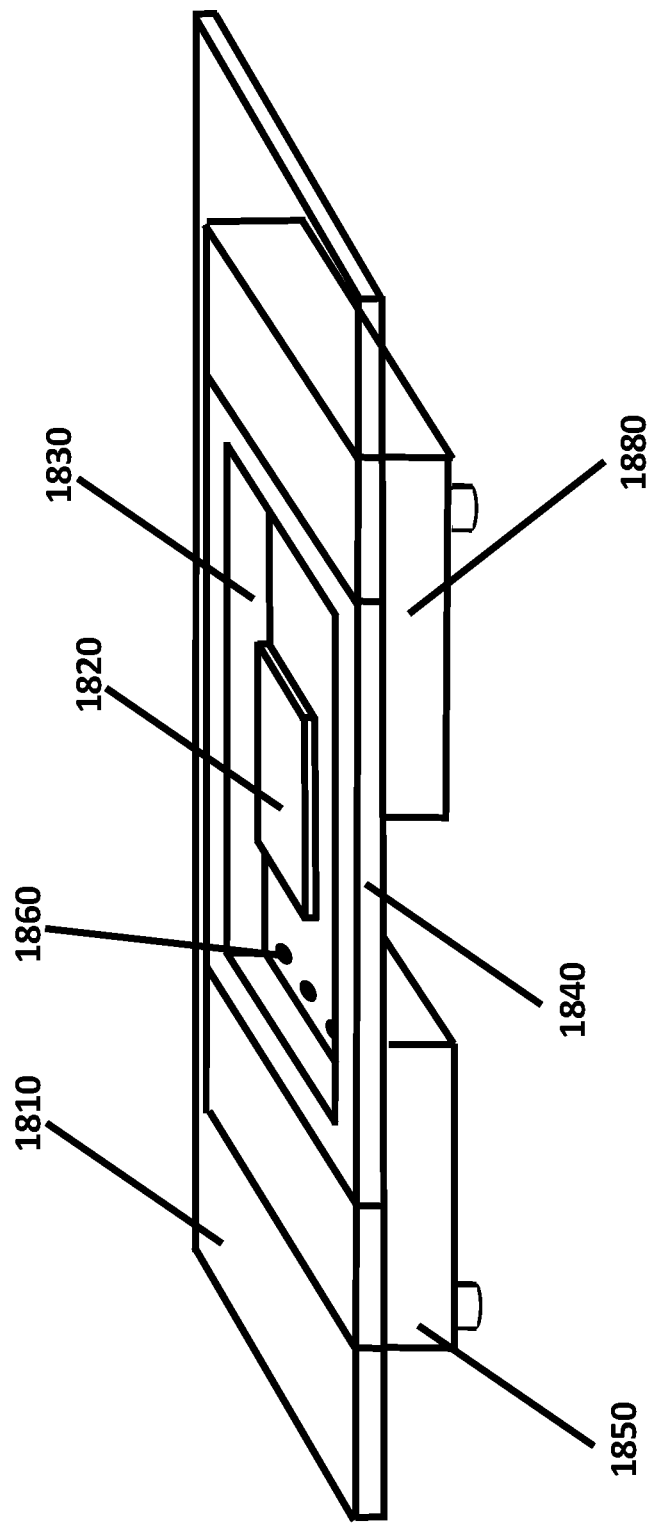
FIG. 18B shows an isometric view of a fluidic device containing a substrate configured to display a plurality of peptides, in accordance with some embodiments.

Broadly, a fluidic device for a polypeptide characterization system may comprise a plurality of features or components. A fluidic device will comprise a body with one or more fluidic ports and a substrate. A fluidic device may further contain additional components, such as one or more fluidic manifolds (e.g., inlet and/or outlet manifolds), surface coatings, and/or structural components. All of the components of a fluidic device may be prefabricated and assembled before being placed in a polypeptide characterization system. The components of a fluidic device may be assembled within the polypeptide characterization system to form the fluidic device. In some configurations, one or more components of a fluidic device may be permanent or reused components of a polypeptide characterization system. For example, inlet or outlet manifolds may be permanently connected to the fluidic system, and the rest of the flow cell of chip may be mated to the manifolds when the chip is fixed in the polypeptide characterization system. FIG. 18A depicts a cross-sectional schematic of a flow cell assembly for a polypeptide characterization assay with bottom mounted fluidic ports. The fluidic device may comprise a main body 1840 with a substrate 1820 on a working surface of the main body 1840. The main body may be joined to a covering body 1810. There may be a void volume 1830 enclosed by the joining of the covering body 1810 to the main body 1840. The void volume 1830 may provide a sufficient volume for the contacting of fluids with a plurality of polypeptides that are bound to the substrate 1820 within the fluidic device. The fluidic device may further comprise a bottom-mounted inlet manifold 1850 that provides an intermediary fluidic connection through a manifold port 1890 and the inlet port 1860 of the fluidic device. The fluidic device may further comprise a bottom-mounted outlet manifold 1880 that provides an intermediary fluidic connection through a manifold port 1892 and the outlet port 1870 of the fluidic device. FIG. 18B shows an isometric view of the flow cell assembly described in FIG. 18A. The flow cell assembly is depicted with a clear glass covering body that permits viewing of the internal features of the flow cell assembly. The substrate 1820 is joined to the upper surface of the main body 1840 that is coplanar with the bottom surface of the covering body 1810. The upper surface of the substrate 1820 is exposed within the void volume 1830. The inlet manifold 1850 and outlet manifold 1880 are joined to the bottom surfaces of the covering body 1810 and the main body 1840. Manifold ports 1890 and 1892 provide fluidic connection through the manifolds to the inlet ports 1860 and outlet ports (not shown).

Figure 18C:
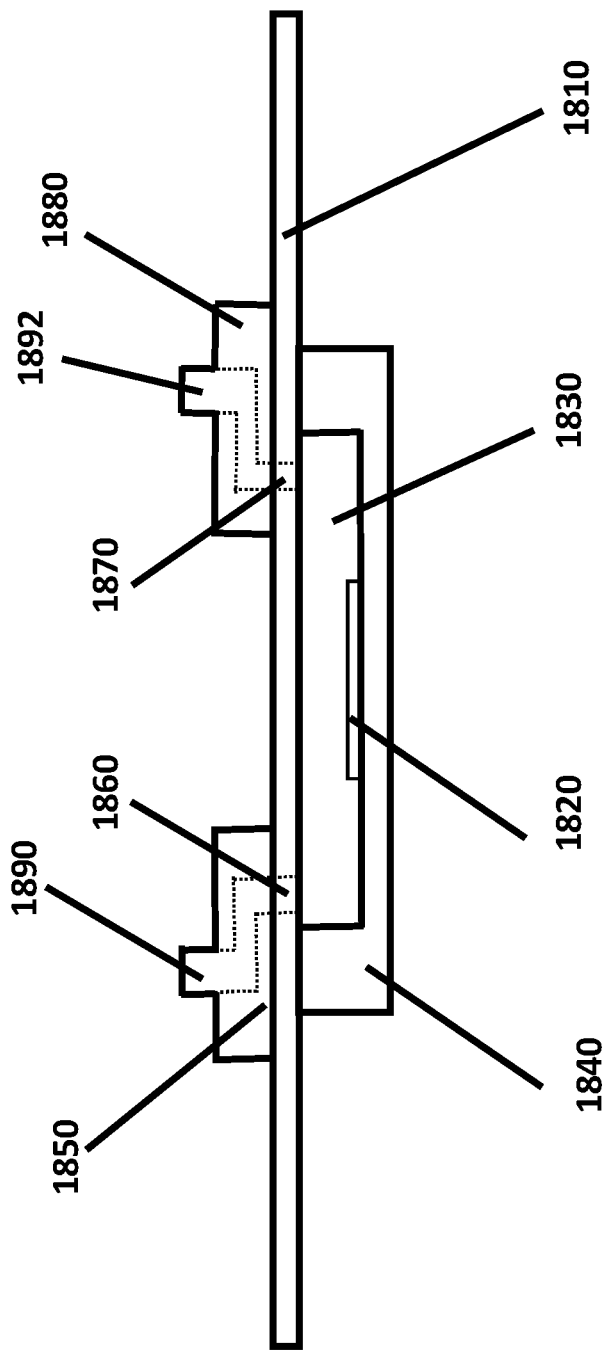
FIG. 18C shows a cross-sectional schematic of a fluidic device containing a substrate configured to display a plurality of peptides, in accordance with some embodiments.

FIG. 18C depicts an alternative flow cell assembly for a polypeptide characterization assay with top-mounted fluidic ports. The fluidic device may comprise a main body 1840 with a substrate 1820 on a working surface of the main body 1840. The main body may be joined to a covering body 1810. There may be a void volume 1830 enclosed by the joining of the covering body 1810 to the main body 1840. The void volume 1830 may provide a sufficient volume for the contacting of fluids with a plurality of polypeptides that are bound to the substrate 1820 within the fluidic device. The fluidic device may further comprise a top-mounted inlet manifold 1850 that provides an intermediary fluidic connection through a manifold port 1890 and the inlet port 1860 of the fluidic device. The fluidic device may further comprise a top-mounted outlet manifold 1880 that provides an intermediary fluidic connection through a manifold port 1892 and the outlet port 1870 of the fluidic device.

Figure 18D:
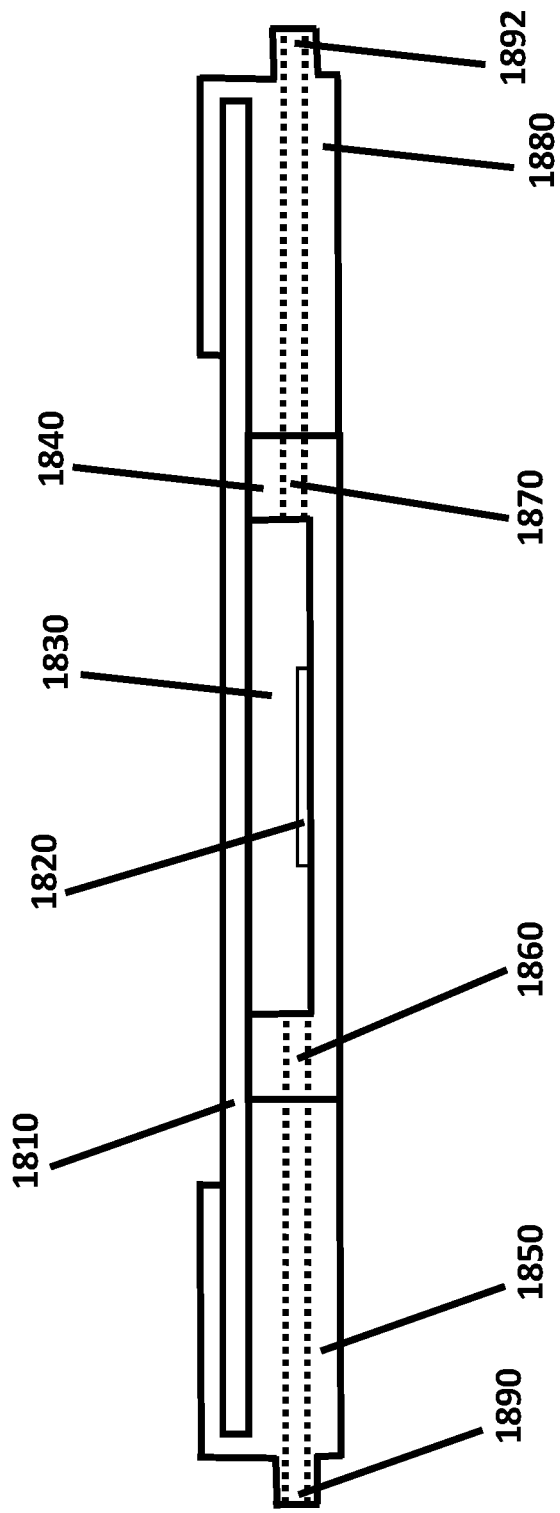
FIG. 18D shows a cross-sectional schematic of a fluidic device containing a substrate configured to display a plurality of peptides, in accordance with some embodiments.

FIG. 18D depicts an alternative flow cell assembly for a polypeptide characterization assay with side-mounted fluidic ports. The fluidic device may comprise a main body

1840 with a substrate 1820 on a working surface of the main body 1840. The main body may be joined to a covering body 1810. There may be a void volume 1830 enclosed by the joining of the covering body 1810 to the main body 1840. The void volume 1830 may provide a sufficient volume for the contacting of fluids with a plurality of polypeptides that are bound to the substrate 1820 within the fluidic device. The fluidic device may further comprise a side-mounted inlet manifold 1850 that provides an intermediary fluidic connection through a manifold port 1890 and the inlet port 1860 of the fluidic device. The fluidic device may further comprise a side-mounted outlet manifold 1880 that provides an intermediary fluidic connection through a manifold port 1892 and the outlet port 1870 of the fluidic device. The inlet manifold 1850 and/or outlet manifold 1880 may contact both the upper and lower surfaces of the covering body. Such a configuration may provide added longitudinal and/or torsional rigidity, as well as points for securement of a fluidic device in the polypeptide characterization system.

A fluidic device may comprise a body. The purpose of the body may be to provide containment and guidance of fluids within the fluidic device. The body may also provide mechanical structure to the fluidic device for purposes such as securing the fluidic device, or resisting mechanical deformation during assay processes. A fluidic device body may comprise one or more components that are assembled to form the chip. Exemplary fluidic device components may include a main body, a covering body, and a substrate. The assembled fluidic device may be leakproof to liquid and/or gaseous fluids. The assembled fluidic device may be resistant to leakage of external fluids into the body or internal fluids out of the body. In particular configurations, the point of entry or exit for fluids may be the inlet and/or outlet ports of the fluidic device.

The body may comprise one or more materials. The body of a fluidic device may be substantially composed of a single material. The body of a fluidic device may comprise more than one material, such as a composite material or two separate materials that are joined at an interface. Exemplary body materials may include synthetic polymers or plastics, biopolymers, metals, semiconductors, ceramics, glasses, inks, and fabrics. In some configurations, a portion of a flow cell of chip may be fabricated by a manufacturing process, such as chemical vapor deposition, atomic layer deposition, nanolithography, machining, etching, 2D printing, or 3D printing. In some configurations, a fluidic device may comprise a main body and a covering body with the same material, e.g., glass, silica, silicon. In some configurations, a fluidic device may comprise a main body and a covering body with differing materials. For example, a fluidic device may comprise a silicon main body and a glass covering body. In some configurations, a fluidic device may comprise one or more primary body materials with small amounts of additional materials added. For example, a glass covering body of a fluidic device may be reinforced in places by one or more layers of rigid material, such as certain polymers or carbon fiber.

The body of a fluidic device may comprise one or more fluidic ports. The fluidic ports may be utilized for ingress of fluids to the fluidic device and/or egress of fluids from the fluidic device. The fluid(s) may be driven through the ports by positive displacement, positive pressure, negative displacement and/or negative pressure. A fluidic device may have dedicated inlet and outlet ports (i.e., inlet ports are used for injection of fluid and outlet ports are used for extraction of fluid). In other configurations, the fluidic ports of a fluidic device may be used for both ingress and egress (i.e., a particular fluidic port may be used alternately for delivery and removal of one or more fluids). Outlet ports may pass through any portion of the fluidic device body, such as the main body or the covering body. A fluidic device may comprise multiple inlet and/or outlet ports. Fluidic ports may be arranged variously within a fluidic device to promote optimal fluid flow. Fluidic ports may be arranged to generate fluid flow patterns, minimize areas of low or minimal fluid transport (i.e., dead spots), prevent bubble formation, enhance fluid injection rates, or enhance fluid extraction rates.

Figure 20A:
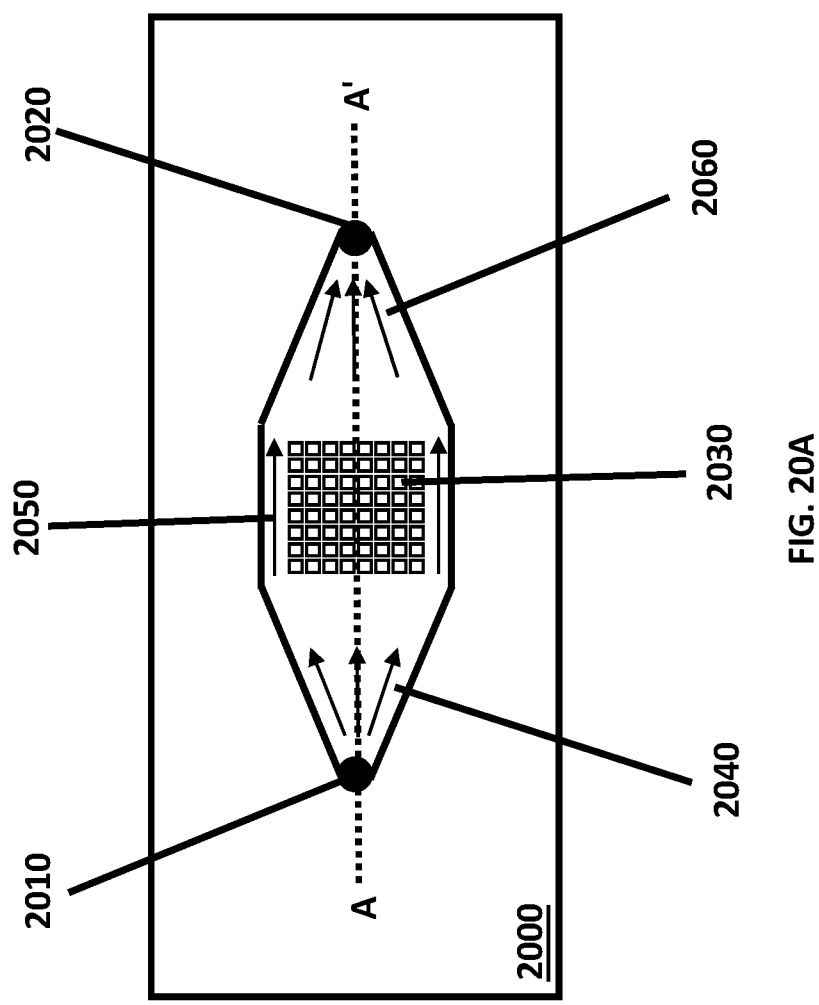
FIG. 20A displays a top-down view of a fluid flow pattern in a fluidic device with a single inlet and single outlet, in accordance with some embodiments.
Figure 20B:
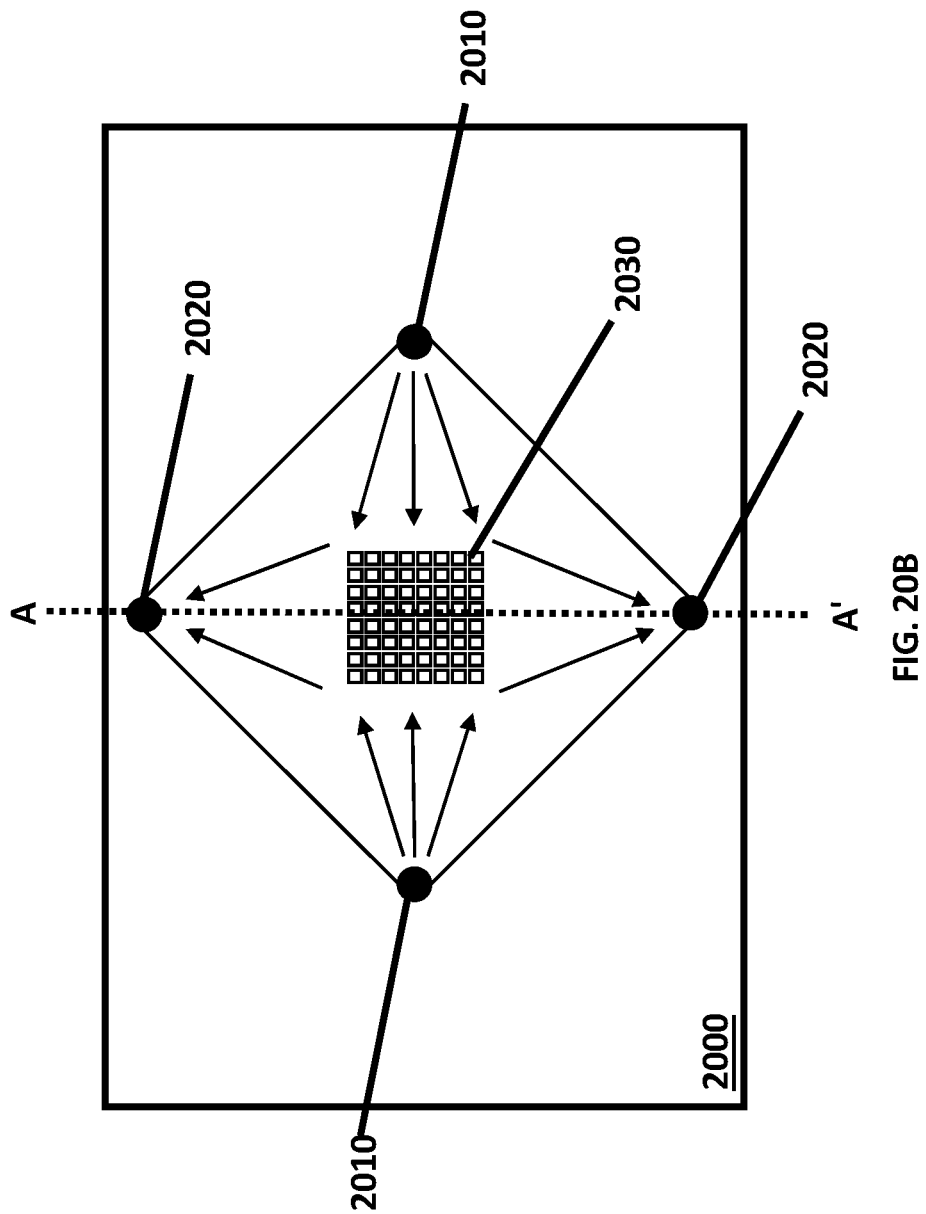
FIG. 20B displays a top-down view of an extensional fluid flow pattern in a fluidic device multiple inlets and multiple outlets, in accordance with some embodiments.

A fluidic device may comprise inlet and outlet ports that are arranged to create a specific fluid flow pattern. The arrangement of the fluidic ports may be combined with the geometry of the void volume in a fluidic device to generate specific fluid flow patterns. FIG. 20A depicts a top-down view of a flow cell 2000 with a uniform flow pattern over a substrate 2030 along an axis A-A'. Flow of a fluid is established by delivery through inlet port 2010 and removal through an outlet port 2020. The void volume of the flow cell is divided into an entrance region 2040 with a developing fluid flow pattern, a uniform region 2050 where the flow has achieved a steady state pattern over the substrate 2030, and an exit region 2060 with a converging flow pattern. FIG. 20B depicts a top-down view of a flow cell 2000 with an extensional flow pattern over a substrate 2030 along an axis A-A'. Flow of a fluid is established by delivery through two opposed inlet ports 2010 and removal through two opposed outlet ports 2020. The void volume may be uniformly shaped but the flow pattern may vary due to the relative orientation of inlet and outlet ports. In some configurations, a fluidic device may additionally comprise recirculation ports. Recirculation ports may be utilized to transfer fluid from one region of a fluidic device to another region. For example, recirculation ports may be placed near regions of poor fluidic mixing to increase fluid transfer in those regions. Recirculation ports may be distinguished from inlet and outlet ports by lacking connection to external fluid sources; fluid already delivered into a fluidic device may pass through a recirculation loop.

A fluidic device may comprise a substrate. The substrate may be an active region for a polypeptide characterization assay. The substrate may be configured to bind a plurality of polypeptides at unique, optically observable addresses on the substrate surface. A substrate may comprise a defined area within the flow cell, such as a flat surface or a patterned area. A substrate may be disposed within any region of the fluidic device body, provided that the substrate is optically observable. For example, a flow cell may comprise a silicon main body and a glass covering body with the substrate oriented on either the main body or the covering body. FIGS. 18E and 18F show two possible substrate configurations for a substrate within a horizontal flow cell. The substrate 1820 may be oriented within the void volume 1830 enclosed by the joined main body 1840 and covering body 1810. In FIG. 18E, the substrate 1820 is oriented on the region of the lower surface of the covering body 1810 that is enclosed within the void volume 1830. In FIG. 18F, the substrate 1820 is oriented on the region of the upper surface of the main body 1840 that is enclosed within the void volume 1830.

Figure 19:
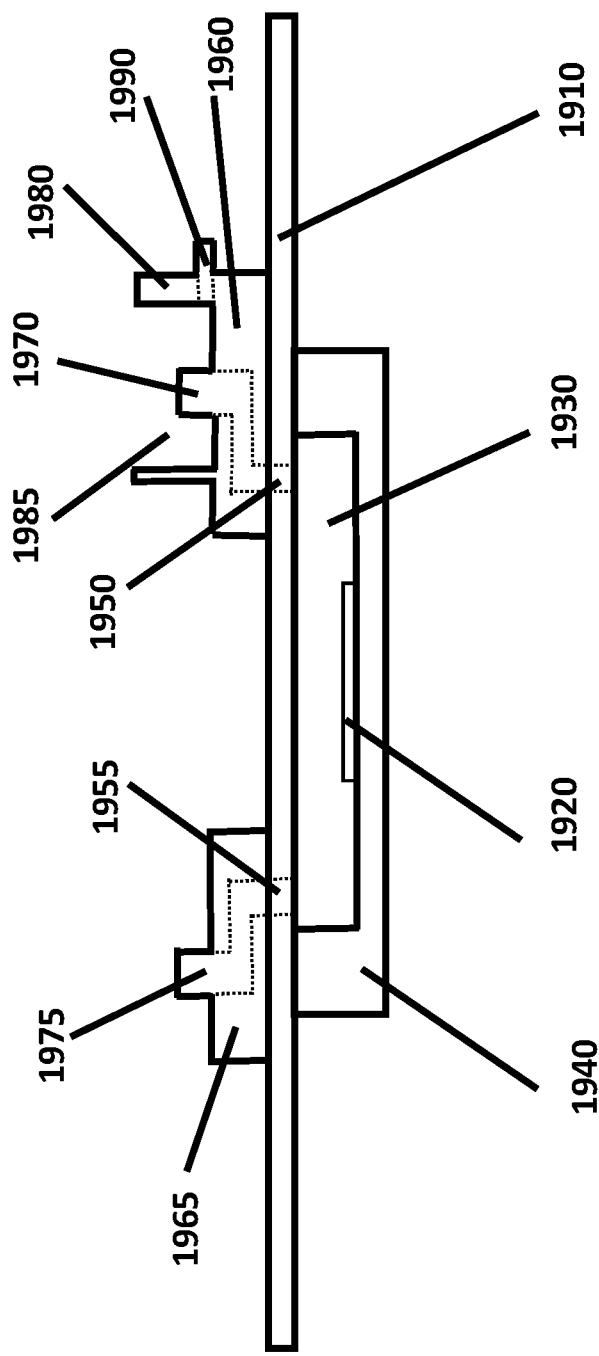
FIG. 19 depicts a cross-sectional schematic of a fluidic device containing a fluid overflow containment barrier, in accordance with some embodiments.

A fluidic device may be engineered to contain overflow and/or permit overflowing fluids to be routed to a waste stream. Overflow of fluids may occur coincidentally during operation or may occur during intended operations. For example, fluids may be purposely overflowed at inlet and/or outlet ports to ensure complete rinsing of fluids containing species that are prone to non-specific absorption (e.g., affinity reagents, fluorophores). Accidental or unintended overflow can also be contained or routed by a fluidic device of the present disclosure. An inlet port or an outlet port may be cleaned by injecting fluid through a differing port that is in fluid communication with the port to be cleaned (i.e., an inlet port may be cleaned by injecting fluid through an outlet port). FIG. 19 depicts a fluidic device configuration that is designed to accommodate overflow of a fluid from a port. The fluidic device comprises a covering body 1910 and a main body 1940 that enclose a void volume 1930 containing a substrate 1920 that is configured to bind a plurality of polypeptides at individual, optically observable addresses. The fluidic device also comprises an inlet port 1950 and an outlet port 1955 that are configured to provide fluid to the void volume 1930 through the covering body 1940. The inlet port is connected to an inlet manifold 1960 that is in contact with the covering body 1940 and is configured to provide fluid transfer from a manifold port 1970 to the inlet port 1950. Similarly, the outlet port is connected to an outlet manifold 1965 that is in contact with the covering body 1940 and is configured to provide fluid transfer from a manifold port 1975 to the outlet port 1955. The inlet manifold further comprises a containment barrier 1980 that creates an overflow volume 1984. The overflow volume 1984 is drained through a drainage port 1990 that may be connected to a drainage pump, such as a vacuum pump. A containment barrier 1980 and overflow volume 1984 may be configured on an upper surface, lower surface, or side surface of a fluidic device. An overflow volume 1984 may be open or closed to ensure capture and containment of any overflowing fluids.

A substrate may comprise the same material as the fluidic device main body. A substrate may comprise a different material than the main body of the fluidic device. A substrate may be directly deposited or bonded to the main body of the fluidic device (e.g., by chemical vapor deposition or atomic layer deposition). A substrate may be joined or bonded to the main body of the fluidic device by an intermediate layer, such as an adhesive, compressed gasket or resin. A substrate may comprise a coating material that facilitates the binding of polypeptides to the substrate. A substrate coating may include a polymer (e.g, an ionic polymer, acrylic, polyethylene oxide), a metal oxide (e.g., $ZrO_2$, $TiO_2$, $SnO_2$), a metal (e.g, Au, Si, Ge, an organic functional group (e.g, $-NH_2$, $-SH$), or an organometallic functional group (e.g., an organosilane). Hydrogels such as polyacrylamide can be used as substrate coatings.

A fluidic device may comprise one or more manifolds. A manifold may be defined as any fluidic component joined to the external region of a fluidic device that provides an interface between the fluidic system of the polypeptide characterization system and the fluidic ports of the fluidic device. A manifold may be utilized with a fluidic device to create secure fluidic connections. For example, a manifold may be utilized to create a connection between a section of pipe or tubing with a fixed or industry-standard cross-sectional sizing (e.g., HPLC tubing) and a fluidic port with a smaller or larger port diameter. A manifold may be utilized to improve the control of fluid transfer through a fluidic device. For example, a manifold may be designed to prevent or minimize the flow of air bubbles into a fluidic device. A manifold may be utilized to increase the mechanical strength or rigidity of a fluidic device. For example, a manifold may provide sufficient strength or rigidity to prevent bending and/or breakage of a flow cell during connection and/or disconnection of fluidic connections (e.g., pipette tips, luer-lock fittings, etc.).

A fluidic device may comprise one or more void volumes. Each void volume within a fluidic device may comprise a substrate that is configured to bind a plurality of polypeptides at unique, individually observable addresses. In some configurations, a fluidic device may comprise a void volume that does not comprise a substrate configured to bind polypeptides. Such void volumes may be utilized for other processes, such as mixing or settling of fluids, bubble capture or removal, or capture of unwanted molecules or particulates. A fluidic device may comprise multiple void volumes connected in a serial or parallel configuration. Each void volume may be separated sufficiently to permit independent analysis of polypeptides in each void volume. A fluidic device may comprise about 1, 2, 3, 4, 5, 6, 7, 8, 9, 10, 11, 12, 13, 14, 15, 16, 17, 18, 19, 20, 25, 30, 35, 40, 50, 60, 70, 80, 90, 100 or more than 100 void volumes. A fluidic device may comprise at least about 1, 2, 3, 4, 5, 6, 7, 8, 9, 10, 11, 12, 13, 14, 15, 16, 17, 18, 19, 20, 25, 30, 35, 40, 50, 60, 70, 80, 90, 100 or more than 100 void volumes. Alternatively or additionally, a fluidic device may comprise no more than about 100, 90, 80, 70, 60, 50, 40, 35, 30, 25, 20, 19, 18, 17, 16, 15, 14, 13, 12, 11, 10, 9, 8, 7, 6, 5, 4, 3, 2 or less than 2 void volumes.

A void volume may have a total volume of about 1 microliter (μl), 2 μl, 3 μl, 4 μl, 5 μl, 6 μl, 7 μl, 8 μl, 9 μl, 10 μl, 11 μl, 12 μl, 13 μl, 14 μl, 15 μl, 16 μl, 17 μl, 18 μl, 19 μl, 20 μl, 21 μl, 22 μl, 23 μl, 24 μl, 25 μl, 26 μl, 27 μl, 28 μl, 29 μl, 30 μl, 31 μl, 32 μl, 33 μl, 34 μl, 35 μl, 36 μl, 37 μl, 38 μl, 39 μl, 40 μl, 45 μl, 50 μl, 60 μl, 70 μl, 80 μl, 90 μl, 100 μl, 200 μl, 300 μl, 400 μl, 500 μl, 750 μl, 1 milliliter (ml), 5 ml, 10 ml, or more than 10 ml. A void volume may have a total volume of at least about 1 μl, 2 μl, 3 μl, 4 μl, 5 μl, 6 μl, 7 μl, 8 μl, 9 μl, 10 μl, 11 μl, 12 μl, 13 μl, 14 μl, 15 μl, 16 μl, 17 μl, 18 μl, 19 μl, 20 μl, 21 μl, 22 μl, 23 μl, 24 μl, 25 μl, 26 μl, 27 μl, 28 μl, 29 μl, 30 μl, 31 μl, 32 μl, 33 μl, 34 μl, 35 μl, 36 μl, 37 μl, 38 μl, 39 μl, 40 μl, 45 μl, 50 μl, 60 μl, 70 μl, 80 μl, 90 μl, 100 μl, 200 μl, 300 μl, 400 μl, 500 μl, 750 μl, 1 ml, 5 ml, 10 ml, or more than 10 ml. Alternatively or additionally, a void volume may have a total volume of no more than about 10 ml, 5 ml, 1 ml, 750 μl, 500 μl, 400 μl, 300 μl, 200 μl, 100 μl, 90 μl, 80 μl, 70 μl, 60 μl, 50 μl, 45 μl, 40 μl, 39 μl, 38 μl, 37 μl, 36 μl, 35 μl, 34 μl, 33 μl, 32 μl, 31 μl, 30 μl, 29 μl, 28 μl, 27 μl, 26 μl, 25 μl, 24 μl, 23 μl, 22 μl, 21 μl, 20 μl, 19 μl, 18 μl, 17 μl, 16 μl, 15 μl, 14 μl, 13 μl, 12 μl, 11 μl, 10 μl, 9 μl, 8 μl, 7 μl, 6 μl, 5 μl, 4 μl, 3 μl, 2 μl, 1 μl, or less than 1 μl.

A fluidic device may include additional features that provide utility to the fluidic device. The additional features may include joined or embedded electrical sensors or circuits. Circuits, including resistive heating elements, may be embedded within a portion of one or more flow cell components to provide utilities such as heating, capacitance measurements, and sensing. Electrical circuits may be embedded, formed, or deposited conductive materials (e.g., copper wiring). Electrical elements may also be formed by the printing of conductive inks on a surface of a fluidic device. In some configurations, a fluidic device may comprise one or more printed or applied strain gauges (e.g., on a top surface of the flow cell covering body) that facilitate measurement of flow cell deformation. Electrical sensing of deformation may prevent errant flow cell operations by sensing and intervening in processes that are producing high levels of stress or strain on the fluidic device.

A fluidic device for a polypeptide characterization assay may be sized to fit within a protein characterization system. The size of a fluidic device may refer to area footprint, the volumetric footprint, or actual shape profile of the fluidic device. A fluidic device size may be determined by several parameters including the size of the polypeptide analysis area, the number of polypeptides to be analyzed, the volume of the void volume, the number of void volumes per fluidic device, the size or volume of ancillary elements such as manifolds, and extra space on a fluidic device for mechanical structuring or securement of the fluidic device within the polypeptide characterization system.

A fluidic device may have any reasonable shape, profile, footprint, or conformation, such as rectangular, square, circular, triangular, cubic, cylindrical, irregular, etc. For flow cells or chips with irregular or complex shapes or profiles, the area footprint may be defined as the smallest rectangle that will fully surround the fluidic device when placed on a flat surface, with the length and width measured as the sides of the rectangle. For flow cells or chips with irregular or complex shapes or profiles, the volumetric footprint may be defined as the smallest rectangular cube that will fully surround the fluidic device, with the length, width, and depth measured as the sides of the rectangular cube. A flow cell may contain at least one face that is substantially flat to facilitate analysis of polypeptides bound to the substrate. In some configurations, the flat face may be substantially rectangular in terms of its area footprint. The depth of a rectangular fluidic device may be thinner than the length or width of the flat face. The length, width, or depth of a fluidic device may be measured with reference to the body of the fluidic device (excluding any additional components such as manifolds, reinforcements, etc.), or may include additional components.

A fluidic device may have a length or width of about 1 centimeter (cm), 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 35 cm, 40 cm, 45 cm, 50 cm, 60 cm, 70 cm, 80 cm, 90 cm, 100 cm, or more than 100 cm. A fluidic device may have a length or width of at least about 1 centimeter (cm), 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 35 cm, 40 cm, 45 cm, 50 cm, 60 cm, 70 cm, 80 cm, 90 cm, 100 cm, or more than 100 cm. Alternatively or additionally, a fluidic device may have a length or width of no more than about 100 cm, 90 cm, 80 cm, 70 cm, 60 cm, 50 cm, 40 cm, 30 cm, 29 cm, 28 cm, 27 cm, 26 cm, 25 cm, 24 cm, 23 cm, 22 cm, 21 cm, 20 cm, 19 cm, 18 cm, 17 cm, 16 cm, 15 cm, 14 cm, 13 cm, 12 cm, 11 cm, 10 cm, 9 cm, 8 cm, 7 cm, 6 cm, 5 cm, 4 cm, 3 cm, 2 cm, 1 cm, or less than 1 cm.

A fluidic device may have a depth of about 0.1 millimeters (mm), 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 1 cm, 2 cm, 3 cm, 4 cm, 5 cm, 6 cm, 8 cm, 9 cm, 10 cm, or more than 10 cm. A fluidic device may have a depth of at least about 0.1 millimeters (mm), 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 1 cm, 2 cm, 3 cm, 4 cm, 5 cm, 6 cm, 8 cm, 9 cm, 10 cm, or more than 10 cm. Alternatively or additionally, a fluidic device may have a depth of no more than about 10 cm, 9 cm, 8 cm, 7 cm, 6 cm, 5 cm, 4 cm, 3 cm, 2 cm, 1 cm, 9 mm, 8 mm, 7 mm, 6 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm, or less than 0.1 mm. The depth of the fluidic device may be specified at a particular thickness relative to the length or width of the fluidic device due to various factors such as the mechanical strength of the body material and the influence of fluidic device depth on physical measurements (e.g., thinner for optical measurements). A fluidic device may have a ratio of width:depth or length:depth of at least about 0.1, 0.5, 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, or more than about 200. Alternatively or additionally, a flow cell may have a ratio of width:depth or length:depth of no more than 200, 190, 180, 170, 160, 150, 140, 130, 120, 110, 100, 95, 90, 85, 80, 75, 70, 65, 60, 55, 50, 45, 40, 35, 30, 25, 20, 15, 10, 5, 1, 0.5, 0.1 or less than 0.1.

A fluidic device may be designed to have a substantially flat face to facilitate a physical measurement, e.g., optical detection of polypeptides. A fluidic device may be designed to be flat across an area that is at least as large as the field of view of a detection device that is used to observe an array of polypeptides in or on the fluidic device. The flatness of a fluidic device may be selected to minimize the crosstalk between neighboring addresses when interrogating a polypeptide-affinity reagent interaction at a unique, optically resolvable address in or on the fluidic device. The degree of flatness (i.e., minimal longitudinal or torsional camber) may influence the choice of materials used to construct the body of a fluidic device. For example, a thicker, more rigid main body may be joined to a thinner covering body to minimize the optical thickness of a fluidic device while providing enhanced resistance to deformation in the covering body. In some configurations, a flow cell may comprise a silicon body joined to a glass covering body to enhance the optical and mechanical behavior of the fluidic device.

The pitch of a fluidic device may be measured relative to a flat face. The pitch may refer to any substantially flat surface, such as the upper face of a covering body, or a substrate region within a void volume. The pitch may describe the angular deviation from orthogonal of a trace relative to the face of the fluidic device. For example, in optical systems the angular deviation can be measured along the focal axis (also referred to as the z axis). The pitch of a fluidic device may fall within a measurable threshold to perform satisfactorily during physical measurements of polypeptides. A pitch may be measured by any reasonable method, such as surface metrology or a surface profilometer. A surface on or within a fluidic device may have a measured pitch of no more than about 500 milliradians (mrad), 400 mrad, 300 mrad, 200 mrad, 100 mrad, 50 mrad, 25 mrad, 10 mrad, 5 mrad, 1 mrad, 500 microradians (prad), 400 prad, 300 prad, 200 prad, 100 prad, 50 prad, 10 prad, 5 prad, 1 prad, 0.5 prad, 0.1 prad, or less than 0.1 prad. Alternatively or additionally, a surface on or within a fluidic device may have a measured pitch of at least about 0.1 prad, 0.5 prad, 1 prad, 5 prad, 10 prad, 50 prad, 100 prad, 200 prad, 300 prad, 400 prad, 500 prad, 1 mrad, 5 mrad, 10 mrad, 25 mrad, 50 mrad, 100 mrad, 200 mrad, 300 mrad, 400 mrad, 500 mrad, or more than 500 mrad.

Figure 21:
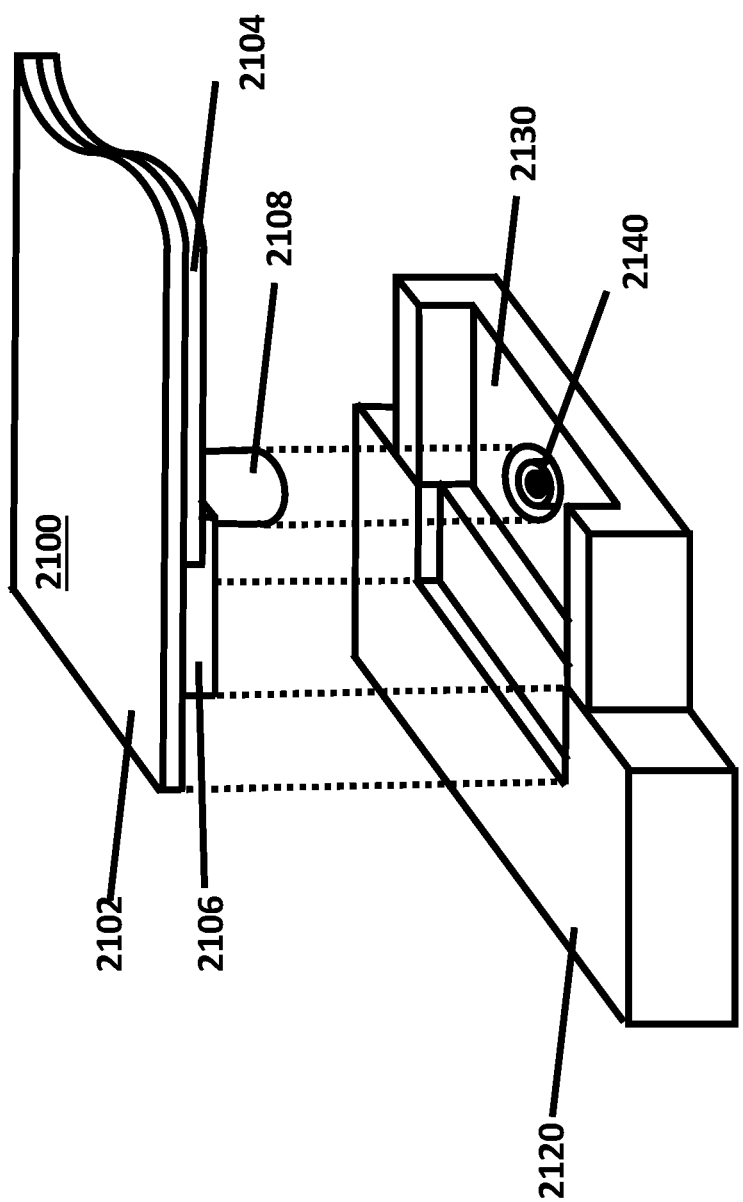
FIG. 21 shows an isometric view of a system for securing a fluidic device and providing fluidic connections, in accordance with some embodiments.

A fluidic device for a polypeptide characterization system may be designed and/or structured to be positioned and/or secured within a polypeptide characterization system of the present disclosure. In some configurations, the flow chip or cell may be positioned and/or secured within a securing structure. A securing structure may primarily serve to provide physical support and stability to a flow cell and provide a fluidic device a uniform location for interfacing with other systems, such as the fluidic system and the physical measurement system. In some configurations, a securing structure may incorporate physical connections with other systems, such as fluidic connections or electrical contacts. FIG. 21 depicts a securing structure 2120 for one side of a fluidic device 2100. The fluidic device comprises a covering body 2102, a main body 2104, and a manifold 2106 comprising a fluidic port 2108. The securing body comprises an inset region 2130 that provides consistent physical positioning and lateral stability to the flow cell 2100 in the securing body 2110. The securing body further comprises an optional fluidic connection that is positioned to provide a secure connection to the fluidic port 2108 of the flow chip manifold 2106. The securing body of FIG. 21 may include one or more counterpart securing bodies (not shown) that secure other portions of a fluidic device. A securing body may comprise more than one piece. For example, the securing body 2110 depicted in FIG. 21 may also include an upper piece that mates to the securing body 2110 and covers at least the end of the covering body 2102 of the flow cell 2100. Additional pieces may provide additional securement and stability, such as vertical stability, as well as additional utilities such as fluidic connections and electrical connections.

A polypeptide characterization system may utilize a fluidic device with multiple substrate regions to facilitate analysis of multiple batches of polypeptides simultaneously or in concert. A polypeptide characterization system may utilize arrangements of multiple flow cells or chips to facilitate analysis of multiple batches of polypeptides simultaneously or in concert. A fluidic device may comprise multiple void volumes containing a substrate to facilitate the analysis of multiple batches of polypeptides. The design and arrangement of flow cells or chips, or multi-chip systems may depend upon the intended purpose of the polypeptide characterization assay.

Fluidic device design may be influenced by additional design constraints, such as the sizing and materials of industrial standard materials (e.g., glass slides, silicon wafers), and the price of critical materials. In some configurations, components of the flow cell body may be designed to minimize the amount of a material needed for fluidic device fabrication. For example, FIGS. 18A-18E depict various embodiments of flow cells with a shorter but thicker main body 1840 and a longer but thinner covering body 1810. In some configurations, a fluidic device may comprise a smaller silicon main body comprising a substrate, and a larger glass covering body. The larger components of a fluidic device may be utilized to provide surface area for positioning and attachment, as well as mechanical strength and stability.

Single Molecule Detection Assays

In some examples, the fluidic device may be utilized in a single-molecule detection assay that comprises three aspects: 1) an addressable substrate in which proteins and/or protein fragments can be conjugated; 2) a set of affinity reagents, e.g. where each affinity reagent can bind to a peptide with varying specificity; and 3) a software that may be able to use a combination of prior knowledge about the binding characteristics of the affinity reagents, the specific pattern of binding of affinity reagents at each address in the substrate, and/or a database of the possible sequences of the proteins in the mixture (e.g. the human proteome) to infer the identity of a protein at a precise spatial address in the substrate. In some examples, the precise spatial address may be a unique spatial address.

The samples may be a biological sample containing protein. The samples may be taken from tissue or cells or from the environment of tissue or cells. In some examples, the sample may be a tissue biopsy, blood, blood plasma, extracellular fluid, cultured cells, culture media, discarded tissue, plant matter, synthetic proteins, archael, bacterial and/or viral samples, fungal tissue, archaea, or protozoans. In some examples, the protein may be isolated from its primary source (cells, tissue, bodily fluids such as blood, environmental samples etc) during sample preparation. The protein may or may not be purified from its primary source. In some configurations, the primary source may be homogenized prior to further processing. In some configurations, cells may be lysed using a buffer such as RIPA buffer. Denaturing buffers may also be used at this stage. The sample may be filtered or centrifuged to remove lipids and particulate matter. The sample may also be purified to remove nucleic acids, or may be treated with RNases and DNases. The sample may contain intact proteins, denatured proteins, protein fragments or partially degraded proteins.

The sample may be taken from a subject with a disease or disorder. The disease or disorder may be an infectious disease, an immune disorder or disease, a cancer, a genetic disease, a degenerative disease, a lifestyle disease, an injury, a rare disease or an age-related disease. The infectious disease may be caused by bacteria, viruses, fungi and/or parasites. Non-limiting examples of cancers include Bladder cancer, Lung cancer, Brain cancer, Melanoma, Breast cancer, Non-Hodgkin lymphoma, Cervical cancer, Ovarian cancer, Colorectal cancer, Pancreatic cancer, Esophageal cancer, Prostate cancer, Kidney cancer, Skin cancer, Leukemia, Thyroid cancer, Liver cancer, and Uterine cancer. Some examples of genetic diseases or disorders include, but are not limited to, cystic fibrosis, Charcot-Marie-Tooth disease, Huntington's disease, Peutz-Jeghers syndrome, Down syndrome, Rheumatoid arthritis, and Tay-Sachs disease. Non-limiting examples of lifestyle diseases include obesity, diabetes, arteriosclerosis, heart disease, stroke, hypertension, liver cirrhosis, nephritis, cancer, chronic obstructive pulmonary disease (copd), hearing problems, and chronic backache. Some examples of injuries include, but are not limited to, abrasion, brain injuries, bruising, burns, concussions, congestive heart failure, construction injuries, dislocation, flail chest, fracture, hemothorax, herniated disc, hip pointer, hypothermia, lacerations, pinched nerve, pneumothorax, rib fracture, sciatica, spinal cord injury, tendons ligaments fascia injury, traumatic brain injury, and whiplash. The sample may be taken before and/or after treatment of a subject with a disease or disorder. Samples may be taken before and/or after a treatment. Samples may be taken during a treatment or a treatment regime. Multiple samples may be taken from a subject to monitor the effects of the treatment over time. The sample may be taken from a subject known or suspected of having an infectious disease for which diagnostic antibodies may not be available.

The sample may be taken from a subject suspected of having a disease or a disorder. The sample may be taken from a subject experiencing unexplained symptoms, such as fatigue, nausea, weight loss, aches and pains, weakness, or memory loss. The sample may be taken from a subject having explained symptoms. The sample may be taken from a subject at risk of developing a disease or disorder due to factors such as familial history, age, environmental exposure, lifestyle risk factors, or presence of other known risk factors.

The sample may be taken from an embryo, fetus, or pregnant woman. In some examples, the sample may comprise of proteins isolated from the mother's blood plasma. In some examples, proteins isolated from circulating fetal cells in the mother's blood.

Protein may be treated to remove modifications that may interfere with epitope binding. For example, the protein may be glycosidase treated to remove post translational glycosylation. The protein may be treated with a reducing agent to reduce disulfide binds within the protein. The protein may be treated with a phosphatase to remove phosphate groups. Other non-limiting examples of post translational modifications that may be removed include acetate, amide groups, methyl groups, lipids, ubiquitin, myristoylation, palmitoylation, isoprenylation or prenylation (e.g. farnesol and geranylgeraniol), farnesylation, geranylgeranylation, glypiation, lipoylation, flavin moiety attachment, phosphopantetheinylation, and retinylidene Schiff base formation. Samples may also be treated to retain posttranslational protein modifications. In some examples, phosphatase inhibitors may be added to the sample, for example, to protect phosphorylated amino acids from being dephosphorylated. In some examples, oxidizing agents may be added to protect disulfide bonds or reducing agents may be added to protect sulfhydryls.

In some configurations, proteins may be denatured in full or in part. In some embodiments, proteins can be fully denatured. Proteins may be denatured by application of an external stress such as a detergent, a strong acid or base, a concentrated inorganic salt, an organic solvent (e.g., alcohol or chloroform), radiation or heat. Proteins may be denatured by addition of a denaturing buffer. Proteins may also be precipitated, lyophilized and suspended in denaturing buffer. Proteins may be denatured by heating. Methods of denaturing that may be unlikely to cause chemical modifications to the proteins may be used.

Proteins of the sample may be treated to produce shorter polypeptides, either before or after conjugation. Remaining proteins may be partially digested with an enzyme such as ProteinaseK to generate fragments or may be left intact. In further examples the proteins may be exposed to proteases such as trypsin. Additional examples of proteases may include serine proteases, cysteine proteases, threonine proteases, aspartic proteases, glutamic proteases, metalloproteases, and asparagine peptide lyases.

In some configurations, it may be useful to remove extremely large and small proteins (e.g. Titin), such proteins may be removed by filtration or other appropriate methods. In some examples, extremely large proteins may include proteins that are over 400 kD, 450 kD, 500 kD, 600 kD, 650 kD, 700 kD, 750 kD, 800 kD or 850 kD. In some examples, extremely large proteins may include proteins that are over about 8,000 amino acids, about 8,500 amino acids, about 9,000 amino acids, about 9,500 amino acids, about 10,000 amino acids, about 10,500 amino acids, about 11,000 amino acids or about 15,000 amino acids. In some examples, small proteins may include proteins that are less than about 10 kD, 9 kD, 8 kD, 7 kD, 6 kD, 5 kD, 4 kD, 3 kD, 2 kD or 1 kD. In some examples, small proteins may include proteins that are less than about 50 amino acids, 45 amino acids, 40 amino acids, 35 amino acids or about 30 amino acids. Extremely large or small proteins can be removed by size exclusion chromatography. Extremely large proteins may be isolated by size exclusion chromatography, treated with proteases to produce moderately sized polypeptides and recombined with the moderately size proteins of the sample.

In some configurations, proteins may be ordered by size. In some configurations, proteins may be ordered by sorting proteins into microwells. In some configurations, proteins may be ordered by sorting proteins into nanowells. In some configurations, proteins may be ordered by running proteins through a gel such as an SDS-PAGE gel. In some configurations, proteins may be ordered by other size-dependent fractionation methods. In some configurations, proteins may be separated based on charge. In some configurations, proteins may be separated based on hydrophobicity. In some configurations, proteins may be separated based on other physical characteristics. In some configurations, proteins may be separated under denaturing conditions. In some configurations, proteins may be separated under non-denaturing conditions. In some configurations, different fractions of fractionated proteins may be placed on different regions of the substrate. In some configurations, different portions of separated proteins may be placed on different regions of the substrate. In some configurations, a protein sample may be separated in an SDS-PAGE gel and transferred from the SDS-PAGE gel to the substrate such that the proteins may be sorted by size in a continuum. In some configurations, a protein sample may be sorted into three fractions based on size, and the three fractions may be applied to a first, second, and third region of the substrate, respectively. In some configurations, proteins used in the systems and methods described herein may be sorted. In some configurations, proteins used in the systems and methods described herein may not be sorted.

Proteins may be tagged, e.g. with identifiable tags, to allow for multiplexing of samples. Some non-limiting examples of identifiable tags include: fluorophores or nucleic acid barcoded base linkers. Fluorophores used may include fluorescent proteins such as GFP, YFP, RFP, eGFP, mCherry, tdtomato, FITC, Alexa Fluor 350, Alexa Fluor 405, Alexa Fluor 488, Alexa Fluor 532, Alexa Fluor 546, Alexa Fluor 555, Alexa Fluor 568, Alexa Fluor 594, Alexa Fluor 647, Alexa Fluor 680, Alexa Fluor 750, Pacific Blue, Coumarin, BODIPY FL, Pacific Green, Oregon Green, Cy3, Cy5, Pacific Orange, TRITC, Texas Red, R-Phycoerythrin, Allophcocyanin, or other fluorophores known in the art.

A number of protein samples may be multiplexed. For example, a multiplexed reaction may contain proteins from 2, 3, 4, 5, 6, 7, 8, 9, 10, 11, 12, 13, 14, 15, 16, 17, 18, 19, about 20, about 25, about 30, about 35, about 40, about 45, about 50, about 55, about 60, about 65, about 70, about 75, about 80, about 85, about 90, about 95, about 100 or more than 100 initial samples. The identifiable tags may provide a way to interrogate each protein as to its sample of origin, or may direct proteins from different samples to segregate to different areas on a solid support.

In some embodiments, the proteins may be then applied to a functionalized substrate within a fluidic device to chemically attach proteins to the substrate. In some configurations, the proteins may be attached to the substrate via biotin attachment. In some configurations, the proteins may be attached to the substrate via nucleic acid attachment. In some embodiments, the proteins may be applied to an intermediate substance, where the intermediate substance may be then attached to the substrate. In some configurations, proteins may be conjugated to beads (e.g., gold beads) which may then be captured on a surface (e.g., a thiolated surface). In some configurations, one protein may be conjugated to each bead. In some configurations, proteins may be conjugated to beads (e.g., one protein per bead) and the beads may be captured on a surface (e.g. in microwells and/or nanowells).

The substrate may be indirectly functionalized. For example, the substrate may be PEGylated and a functional group may be applied to all or a subset of the PEG molecules. Additionally, as discussed above, in some configurations beads (e.g., gold beads) may be conjugated, and then the beads may be captured on a surface (e.g., a thiolated surface). In some configurations, one protein may be conjugated to each bead. In some configurations, proteins may be conjugated to beads (e.g., one protein per bead) and the beads may be captured on a surface (e.g. in microwells and/or nanowells).

In some configurations, a substrate may have microwells that range in size from about 5 µm to about 500 µm. In some configurations, a substrate may have microwells that range in size from 10 µm to 100 µm. In some configurations, a substrate may have microwells that range in size from about 10 µm to about 100 µm. In some configurations, a substrate may have a range of different sized microwells such that proteins of different sizes may be sorted into different sized microwells. In some configurations, microwells in the substrate may be distributed by size (e.g. with larger microwells distributed in a first region and with smaller microwells distributed in a second region). In some configurations, a substrate may have microwells of about ten different sizes. In some configurations, a substrate may have microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

In some configurations, a substrate may have nanowells of different sizes. In some configurations, nanowells may be about 100 nanometers (nm), about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, or between 950 nm and 1 micrometer. In some configurations, a substrate may have nanowells that range in size from 100 nm to 1 micrometer. In some configurations, a substrate may have nanowells that range in size from 100 nm to 500 nm. In some configurations, a substrate may have a range of different sized nanowells such that proteins of different sizes may be sorted into different sized nanowells. In some configurations, nanowells in the substrate may be distributed by size (e.g. with larger nanowells distributed in a first region and with smaller nanowells distributed in a second region). In some configurations, a substrate may have nanowells of about ten different sizes. In some configurations, a substrate may have nanowells of about 20 different sizes, or more than 30 different sizes.

In some configurations, a substrate may have a range of different sized nanowells and/or microwells such that proteins of different sizes may be sorted into different sized nanowells and/or microwells. In some configurations, nanowells and/or microwells in the substrate may be distributed by size (e.g. with larger microwells distributed in a first region and with smaller nanowells distributed in a second region). In some configurations, a substrate may have nanowells and/or microwells of about ten different sizes. In some configurations, a substrate may have nanowells and/or microwells of about 20 different sizes, about 25 different sizes, about 30 different sizes, about 35 different sizes, about 40 different sizes, about 45 different sizes, about 50 different sizes, about 55 different sizes, about 60 different sizes, about 65 different sizes, about 70 different sizes, about 75 different sizes, about 80 different sizes, about 85 different sizes, about 90 different sizes, about 95 different sizes, about 100 different sizes, or more than 100 different sizes.

The proteins may be spotted, dropped, pipetted, flowed, washed or otherwise applied to the substrate. In the configuration of a substrate that has been functionalized with a moiety such as an NHS ester, no modification of the protein may be required. In the configuration of a substrate that has been functionalized with alternate moieties (e.g. a sulfhydryl, amine, or linker nucleic acid), a crosslinking reagent (e.g. disuccinimidyl suberate, NHS, sulphonamides) may be used. In the configuration of a substrate that has been functionalized with linker nucleic acid the proteins of the sample may be modified with complementary nucleic acid tags.

In some configurations, a protein may be conjugated to a nucleic acid. Using the nucleic acid, a nucleic acid nanoball or other nucleic acid structure (e.g., DNA origami) may be formed, thereby having the protein linked to the nucleic acid nanoball or other nucleic acid structure. When the nucleic acid nanoball or other nucleic acid structure is attached to a substrate, the protein attached to the nucleic acid may be attached to the substrate by way of the nucleic acid nanoball or other nucleic acid structure. A protein may be conjugated to a substrate after being conjugated to a nucleic acid. A protein may be conjugated to a nucleic acid (e.g., nucleic acid nanoball or other nucleic acid structure) after the nucleic acid has been conjugated to the substrate. A DNA nanoball or other nucleic acid structure can be attached (e.g. by adsorption or by conjugation) to a substrate. The substrate may have a functionalized surface to which the nucleic acid nanoballs can attach.

In some configurations, a nucleic acid nanoball or other nucleic acid structure may be formed with a functionally active terminus (e.g. a maleimide, NHS-Ester, trans-cyclooctene, etc.). The protein may then be conjugated to the nanoball or nucleic acid structure, thereby having the protein linked to the nucleic acid nanoball. When the nucleic acid nanoball or other nucleic acid structure is attached to a substrate, the protein attached to the nucleic acid may be attached to the substrate by way of the nucleic acid nanoball or other nucleic acid structure. A DNA nanoball or other nucleic acid structure can be attached (e.g. by adsorption or by conjugation) to a substrate. In some configurations, a DNA nanoball or other nucleic acid structure may be attached to a substrate by an electrostatic or other non-covalent mechanism. The substrate may have a functionalized surface to which the nucleic acid nanoballs can attach, such as electrostatic interactions with charged functional groups or covalent attachment to functional groups.

In some configurations, a nucleic acid structure (e.g. DNA nanoball or DNA origami) may have a volume that complements the size of a site (i.e. address) on a substrate such that the presence of the nucleic acid structure at the site precludes another nucleic acid structure of similar size from occupying the site. Accordingly, the nucleic acid structures and substrate sites can be sized to achieve steric exclusion, whereby a single nucleic acid structure occupies each site. Thus, the sites on a substrate can be configured to have a diameter or volume that is similar, but slightly larger than, those set forth herein for nucleic acid structures. Similarly, the nucleic acid structures, for example those that are used to attach a polypeptide or other analyte to sites on a substrate can be configured to have diameters or volumes that are similar, but slightly smaller than, those set forth herein for sites on a substrate.

Photo-activatable cross linkers may be used to direct cross linking of a sample to a specific area on the substrate. Photo-activatable cross linkers may be used to allow multiplexing of protein samples by attaching each sample in a known region of the substrate. Photo-activatable cross linkers may allow the specific attachment of proteins which have been successfully tagged, for example by detecting a fluorescent tag before cross linking a protein. Examples of photo-activatable cross linkers include, but are not limited to, N-5-azido-2-nitrobenzoyloxysuccinimide, sulfosuccinimidyl 6-(4'-azido-2'-nitrophenylamino)hexanoate, succinimidyl 4,4'-azipentanoate, sulfosuccinimidyl 4,4'-azipentanoate, succinimidyl 6-(4,4'-azipentanamido)hexanoate, sulfosuccinimidyl 6-(4,4'-azipentanamido)hexanoate, succinimidyl 2-((4,4'-azipentanamido)ethyl)-1,3'-dithiopropionate, and sulfosuccinimidyl 2-((4,4'-azipentanamido)ethyl)-1,3'-dithiopropionate.

Samples may also be multiplexed by restricting the binding of each sample to a discrete area on the substrate. For example, the substrate may be organized into lanes. Another method for multiplexing may be to apply the samples iteratively across the substrate, following each sample application with a protein detection step utilizing a nonspecific protein binding reagent or dye. In some configurations, examples of dyes may include fluorescent protein gel stains such as SYPRO® Ruby, SYPRO® Orange, SYPRO® Red, SYPRO® Tangerine, and Coomassie™ Fluor Orange.

By tracking the locations of all proteins after each addition of sample it may be possible to determine the stage at which each location on the substrate first contained a protein, and thus from which sample that protein was derived. This method may also determine the saturation of the substrate after each application of sample and allows for maximization of protein binding on the substrate. For example, if 30% of functionalized locations are occupied by protein after a first application of a sample then either a second application of the same sample or an application of a different sample may be made.

The polypeptides may be attached to the substrate by one or more residues. In some examples, the polypeptides may be attached via the N terminal, C terminal, both terminals, or via an internal residue.

In addition to permanent crosslinkers, it may be appropriate for some applications to use photo-cleavable linkers and that doing so enables proteins to be selectively extracted from the substrate following analysis. In some configurations, photo-cleavable cross linkers may be used for several different multiplexed samples. In some configurations, photo-cleavable cross linkers may be used from one or more samples within a multiplexed reaction. In some configurations, a multiplexed reaction may comprise control samples cross linked to the substrate via permanent crosslinkers and experimental samples cross linked to the substrate via photo-cleavable crosslinkers.

Each conjugated protein may be spatially separated from each other conjugated protein such that each conjugated protein may be optically resolvable. Proteins may thus be individually labeled with a unique spatial address. In some embodiments, this can be accomplished by conjugation using low concentrations of protein and low density of attachment sites on the substrate so that each protein molecule may be spatially separated from each other protein molecule. In examples where photo-activatable crosslinkers may be used, a light pattern may be used such that proteins may be affixed to predetermined locations.

In some methods, bulk proteins that have been purified may be conjugated to a substrate and processed using methods described herein so as to identify the purified protein. Bulk proteins may comprise purified proteins that have been collected together. In some examples, bulk proteins may be conjugated at a location that may be spatially separated from each other conjugated protein or bulk proteins such that each conjugated protein or bulk protein may be optically resolvable. Proteins, or bulk proteins, may thus be individually labeled with a unique spatial address. In some embodiments, this can be accomplished by conjugation using low concentrations of protein and low density of attachment sites on the substrate so that each protein molecule may be spatially separated from each other protein molecule. In examples where photo-activatable crosslinkers may be used, a light pattern may be used such that one or more proteins may be affixed to predetermined locations.

In some embodiments, each protein may be associated with a unique spatial address. For example, once the proteins may be attached to the substrate in spatially separated sites or locations, each protein can be assigned an indexed address, such as by coordinates. In some examples, a grid of pre-assigned unique spatial addresses may be predetermined. In some embodiments the substrate may contain easily identifiable fixed marks such that placement of each protein can be determined relative to the fixed marks of the substrate. In some examples the substrate may have grid lines and/or and "origin" or other fiducials permanently marked on the surface. In some examples the surface of the substrate may be permanently or semi-permanently marked to provide a reference by which to locate cross linked proteins. The shape of the patterning itself, such as the exterior border of the conjugated polypeptides may also be used as fiducials for determining the unique location of each spot.

The substrate may also contain conjugated protein standards and controls. Conjugated protein standards and controls may be peptides or proteins of known sequence which have been conjugated in known locations. In some examples, conjugated protein standards and controls may serve as internal controls in an assay. The proteins may be applied to the substrate from purified protein stocks, or may be synthesized on the substrate through a process such as Nucleic Acid-Programmable Protein Array (NAPPA).

In some examples, the substrate may comprise fluorescent standards. These fluorescent standards may be used to calibrate the intensity of the fluorescent signals from assay to assay. These fluorescent standards may also be used to correlate the intensity of a fluorescent signal with the number of fluorophores present in an area. Fluorescent standards may comprise some or all of the different types of fluorophores used in the assay.

Once the substrate within the flow cell device has been conjugated with the proteins from the sample, multi-affinity reagent measurements can be performed. The measurement processes described herein may utilize various affinity reagents.

Affinity reagents may be reagents which bind proteins or peptides with reproducible specificity. For example, the affinity reagents may be antibodies, antibody fragments, aptamers, or peptides. In some examples, monoclonal antibodies may be used. In some examples, antibody fragments such as Fab fragments, F(ab')2 fragments, Fab' fragments, Fv fragments, or Fc fragments may be used. In some configurations, the affinity reagents may be commercially available affinity reagents, such as commercially available antibodies. In some configurations, the affinity reagents may be selected by screening commercially available affinity reagents to identify those with useful characteristics. In some configurations, affinity reagents may be screened for their ability to bind a single protein. In some configurations, affinity reagents may be screened for their ability to bind an epitope or amino-acid sequence. The affinity reagents can be narrowly specific for a single protein target in a sample or the affinity reagents can have broad-spectrum affinity for two or more different protein targets in a sample. In some configurations, groups of affinity reagents may be screened for their ability to collectively resolve similar proteins (e.g., those with highly similar sequence) through differential binding. In some configurations, affinity reagents may be screened for overlapping binding characteristics to increase binding specificity for a particular protein. Screening of affinity reagents may be performed in a variety of different ways. One example would be to screen affinity reagents against a NAPPA or an epitope tiling array. In some configurations, protein-specific affinity reagents designed to bind to a protein target may be used (e.g. commercially available antibodies or aptamers). In some configurations, multiple protein-specific affinity reagents may be mixed prior to binding measurement. For example, for each binding measurement pass, a new mixture of protein specific affinity reagents may be selected comprising a subset of the available affinity reagents selected at random from the complete set. For example, each subsequent mixture may be generated in the same random manner, with the expectation that many of the affinity reagents will be present in more than one of the mixtures. In some configurations, protein identifications may be generated more rapidly using mixtures of protein-specific affinity reagents. In some configurations, such mixtures of protein-specific affinity reagents may increase the percentage of unknown proteins for which an affinity reagent binds in individual pass. Mixtures of affinity reagents may consist of 1%, 5%, 10%, 20%, 30%, 40%, 50%, 60%, 70%, 80%, 90% or more of all available affinity reagents.

The affinity reagents of the present disclosure may have a characterized epitope binding specificity. The characterized epitope binding specificity of an affinity reagent may be described in a probabilistic fashion. For example, an affinity reagent may be known to bind to a certain epitope but is known to show a high probability of binding (e.g., fails to show evidence of binding 1 out of every 100 observations). In another example, an affinity reagent may be characterized as binding to a certain epitope with a low, but non-zero, binding probability (e.g., 0.00001% chance of binding for a given observation). A probabilistic characterization of an affinity reagent may include two aspects regarding binding specificity: 1) the structure-dependent likelihood of binding to an epitope; and 2) the environmentally-dependent likelihood of binding to an epitope.

The structure-dependent likelihood of an affinity reagent binding to a peptide epitope may pertain to the effect that polypeptide primary structure (i.e. amino acid sequence) has on affinity reagent binding. For example, affinity reagents may be characterized as binding with increased or decreased preference for particular epitope sequences (e.g., amino acid trimers, tetramers, pentamers, etc.). The structure-dependent likelihood of an affinity reagent binding to an epitope may also be affected by sequence context (e.g., amino acids that flank the amino terminus and/or carbonyl terminus of a peptide epitope; amino acid residues that are proximal to a peptide epitope in the secondary or tertiary structures of a polypeptide, the presence or absence of post-translational modifications in or around a peptide epitope, etc.). An affinity reagent of the present disclosure may have substantial affinity for a family of amino acid epitopes (e.g., AXA, where X represents any of the 20 naturally-occurring amino acids). The structure-dependent likelihood of affinity reagent binding may be calculated for each affinity reagent used for polypeptide characterization, such as by an empirical binding model or a database of binding probabilities. An affinity reagent may have a sequence-specific likelihood of binding to an epitope of at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, 99.999%, 99.9999%, 99.99999%, 99.999999% or more than 99.999999%. Alternatively or additionally, an affinity reagent may have a sequence-specific likelihood of binding to an epitope of no more than about 50%, 45%, 40%, 35%, 30%, 25%, 20%, 15%, 10%, 5%, 4%, 3%, 2%, 1%, 0.5%, 0.1%, 0.01%, 0.001%, 0.0001%, 0.00001%, 0.000001%, or less than 0.000001%.

The environmentally-dependent likelihood of an affinity reagent binding to an epitope in a polypeptide may pertain to the effect of variables other than the structure of the epitope and the polypeptide on affinity reagent binding. For example, affinity reagent binding to a particular epitope may vary based upon solvent chemical composition (e.g., solvent identity, solvent polarity, ionic strength of the solvent, buffer concentration, pH, presence of surfactants or denaturants, etc.). Other non-polypeptide variables may include the time duration of affinity reagent binding, concentration of affinity reagent, concentration of epitope bearing polypeptide, and the presence of externally-applied fields, such as heat, electrical fields, magnetic fields, and fluid velocity fields. An affinity reagent may have an environmentally-dependent likelihood of binding to an epitope of at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, 99.999%, 99.9999%, 99.99999%, 99.999999% or more than 99.999999%. Alternatively or additionally, an affinity reagent may have an environmentally-dependent likelihood of binding to an epitope of no more than about 50%, 45%, 40%, 35%, 30%, 25%, 20%, 15%, 10%, 5%, 4%, 3%, 2%, 1%, 0.5%, 0.1%, 0.01%, 0.001%, 0.0001%, 0.00001%, 0.000001%, or less than 0.000001%.

In some configurations, the structure-dependent binding likelihood and the environmentally-dependent binding likelihood may be combined to determine an overall likelihood or probability of an affinity reagent binding to an epitope. Overall likelihoods or probabilities may be compiled for some or all known epitopes to create a probabilistic binding profile for an affinity reagent. In some configurations, an affinity agent may be characterized as binding to a set of N epitopes with an overall binding probability of at least about 20%, and a set of M epitopes with an overall binding probability of no more than 0.1%, where $N \geq 1$, $M \geq 1$, and $M \geq 10\,N$. An affinity reagent may have an overall likelihood or probability of binding to an epitope of at least about 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, 99.999%, 99.99990%, 99.99999%, 99.999999% or more than 99.999999%. Alternatively or additionally, an affinity reagent may have an overall likelihood or probability of binding to an epitope of no more than about 50%, 45%, 40%, 35%, 30%, 25%, 20%, 15%, 10%, 5%, 4%, 3%, 2%, 1%, 0.5%, 0.1%, 0.01%, 0.001%, 0.0001%, 0.00001%, 0.000001%, or less than 0.000001%.

The affinity reagents may have high, moderate or low specificity. In some examples the affinity reagents may recognize several different epitopes. In some examples the affinity reagents may recognize epitopes present in two or more different proteins. In some examples the affinity reagents may recognize epitopes present in many different proteins. Accordingly, the present disclosure provides broad-spectrum affinity reagents. Alternatively, an affinity reagent used in the methods of this disclosure may be highly specific for a single epitope. In some configurations, an affinity reagent used in the methods of this disclosure may be highly specific for a single epitope containing a post-translational modification.

In some embodiments, an affinity reagent that is directed towards identifying a target amino acid sequence may actually comprise a group of different components which are not differentiated or distinguishable from each other as used in methods described herein. In particular, the different components that may be used to identify the same target amino acid sequence may use the same detection moiety to identify the same target amino acid sequence. For example, an affinity reagent which binds a trimer amino acid sequence (AAA) regardless of flanking sequences may comprise either a single probe which binds the trimer AAA sequence without an effect from flanking sequences, or a group of 400 probes, each of which binds to a different 5 amino acid epitope of the form $\alpha AAA\beta$, where a and p may be an amino acid. In some configurations of the second configuration, the 400 probes may be combined such that there may be an equal amount of each one. In some configurations of the second configuration, the 400 probes may be combined such that the amounts of each probe may be weighted by the characteristic binding affinities of each probe such that there may be an equal probability of a given 5 amino acid epitope being bound. Optionally, a group of different probes that bind to the same target amino acid sequence, such as a trimer amino acid sequence flanked by various amino acids, can be attached to the same type of label or to labels that produce overlapping signals. As such the group of different probes can be detected and evaluated in bulk.

Novel affinity reagents may be generated by a method of particular advantage. Methods of developing affinity reagents include SELEX, phage display, and inoculation. In some examples, affinity reagents may be designed using structure-based drug design methods. Structure-based drug design (or direct drug design) utilizes knowledge of the three-dimensional structure of the epitope of interest and the binding site of the affinity reagent.

In some configurations, the affinity reagents may be labeled with nucleic acid barcodes. In some examples, nucleic acid barcodes may be used to purify affinity reagents after use. In some examples, nucleic acid barcodes may be used to sort the affinity reagents for repeated uses. In some configurations, the affinity reagents may be labeled with fluorophores which may be used to sort the affinity reagents after use.

In some configurations, multiple affinity reagents that may be labeled with nucleic acid barcodes may be multiplexed and then detected using complementary nucleic acid probes. A multiplexed group of affinity reagents may be detected in a single cycle using multiple complementary nucleic acids with distinct detection moieties. In some configurations, a multiplexed group of affinity reagents may be detected in multiple cycles using a single complementary nucleic acid conjugated to a detection moiety. In some configurations, a multiplexed group of affinity reagents may be detected in multiple cycles using multiple complementary nucleic acids each conjugated to a distinct detection moiety. In some configurations, a multiplexed group of affinity reagents may be detected in multiple cycles using multiple complementary nucleic acids each conjugated to a distinct group of detection moieties.

In some configurations, one or more affinity reagents, that may be labeled with nucleic acid barcodes, may be cross-linked to a bound protein. Once the one or more affinity reagents may be cross-linked to the protein, the barcodes may be sequenced to determine the identity of the cross-linked affinity reagent. In some configurations, multiple bound proteins may be exposed to the one or more affinity reagents. In some configurations, when multiple bound proteins may be cross-linked with one or more affinity reagents, the barcodes associated with the bound affinity reagents may be sequenced to determine the identity of the cross-linked affinity reagents associated with each of the multiple bound proteins.

The family of affinity reagents may comprise one or more types of affinity reagents. For example, the methods of the present disclosure may use a family of affinity reagents comprising one or more of antibodies, antibody fragments, Fab fragments, aptamers, peptides, and proteins.

The affinity reagents may be modified. Modifications include, but are not limited to, attachment of a detection moiety. Detection moieties may be directly or indirectly attached. For example, the detection moiety may be directly covalently attached to the affinity reagent, or may be attached through a linker, or may be attached through an affinity reaction such as complementary nucleic acid tags or a biotin streptavidin pair. Attachment methods that may be able to withstand gentle washing and elution of the affinity reagent may be used.

Detection moieties include, but are not limited to, fluorophores, bioluminescent proteins, nucleic acid segments including a constant region and barcode region, or chemical tethers for linking to a nanoparticle such as a magnetic particle. Detection moieties may include several different fluorophores with different patterns of excitation or emission.

The detection moiety may be cleavable from the affinity reagent. This can allow for a step in which the detection moieties may be removed from affinity reagents that may be no longer of interest to reduce signal contamination.

In some configurations, the affinity reagents may be unmodified (e.g. lacking any exogenous labels). For example, if the affinity reagent is an antibody then the presence of the antibody may be detected by atomic force microscopy. The affinity reagents may be unmodified and may be detected, for example, by having antibodies specific to one or more of the affinity reagents. For example, if the affinity reagent is a mouse antibody then the mouse antibody may be detected by using an anti-mouse secondary antibody. Alternately the affinity reagent may be an aptamer which is detected by an antibody specific for the aptamer. The secondary antibody may be modified with a detection moiety as described above. In some configurations, the presence of the secondary antibody may be detected by atomic force microscopy.

In some examples, the affinity reagents may comprise the same modification, for example a conjugated green fluorescent protein, or may comprise two or more different types of modification. For example, each affinity reagent may be conjugated to one of several different fluorescent moieties, each with a different wavelength of excitation or emission. This may allow multiplexing of the affinity reagents as several different affinity reagents may be combined and/or distinguished. In one example, a first affinity reagent may be conjugated to a green fluorescent protein, a second affinity reagent may be conjugated to a yellow fluorescent protein and a third affinity reagent may be conjugated to a red fluorescent protein, thus the three affinity reagents can be multiplexed and identified by their fluorescence. In a further example a first, fourth and seventh affinity reagent may be conjugated to a green fluorescent protein, a second, fifth and eighth affinity reagent may be conjugated to a yellow fluorescent protein and a third, sixth and ninth affinity reagent may be conjugated to a red fluorescent protein; in this configuration the first, second and third affinity reagents may be multiplexed together while the second, fourth and seventh, and third, sixth and ninth affinity reagents form two further multiplexing reactions. The number of affinity reagents which can be multiplexed together may depend on the detection moieties used to differentiate them. For example, the multiplexing of affinity reagents labeled with fluorophores may be limited by the number of unique fluorophores available. For further example, the multiplexing of affinity reagents labeled with nucleic acid tags may be determined by the length of the nucleic acid bar code.

The specificity of each affinity reagent can be determined prior to use in an assay. The binding specificity of the affinity reagents can be determined in a control experiment using known proteins. An appropriate experimental method may be used to determine the specificity of the affinity reagent. In one example a substrate may be loaded with known protein standards at known locations and used to assess the specificity of a plurality of affinity reagents. In another example, a substrate may contain both experimental samples and a panel of controls and standards such that the specificity of each affinity reagent can be calculated from the binding to the controls and standards and then used to identify the experimental samples. In some configurations, affinity reagents with unknown specificity may be included along with affinity reagents of known specificity, data from the known specificity affinity reagents may be used to identify proteins, and the pattern of binding of the unknown specificity affinity reagents to the identified proteins may be used to determine their binding specificity. It may be also possible to reconfirm the specificity of an individual affinity reagent by using the known binding data of other affinity reagents to assess which proteins the individual affinity reagent bound. Thus, with multiple uses of an affinity reagent panel the specificities of the affinity reagents may be increasingly refined with each iteration. While affinity reagents that are uniquely specific to particular proteins may be used, methods described herein may not require them. Additionally, methods may be effective on a range of specificities. In some examples, methods described herein may be particularly efficient when affinity reagents are not specific to a particular protein, but are instead specific to amino acid motifs (e.g. a tri-peptide such as AAA).

In some examples, one or more affinity reagents may be chosen to bind amino acid motifs of a given length, such as 2, 3, 4, 5, 6, 7, 8, 9, 10, or more than 10 amino acids. In some examples, one or more affinity reagents may be chosen to bind amino acid motifs of a range of different lengths from 2 amino acids to 40 amino acids.

In some examples, the affinity reagents may be chosen to have high, moderate, or low binding affinities. In some configurations, affinity reagents with low or moderate binding affinities may be used. In some configurations, the affinity reagents may have dissociation constants of about $10^{-3}$ M, $10^{-4}$ M, $10^{-5}$ M, $10^{-6}$ M, $10^{-7}$ M, $10^{-8}$ M, $10^{-9}$ M, $10^{-10}$ M or lower. In some configurations, the affinity reagents may have dissociation constants of greater than about $10^{-10}$M, $10^{-9}$ M, $10^{-8}$ M, $10^{-7}$ M, $10^{-6}$ M, $10^{-5}$ M, $10^{-4}$ M, $10^{-3}$ M, $10^{-2}$ M or higher.

Some of the affinity reagents may be chosen to bind modified amino acid sequences, such as phosphorylated or ubiquinated amino acid sequences. In some examples, one or more affinity reagents may be chosen to be broadly specific for a family of epitopes that may be contained by one or more proteins. In some examples, one or more affinity reagents may bind two or more different proteins. In some examples, one or more affinity reagents may bind weakly to their target or targets. For example, affinity reagents may bind less than 10%, less than 10%, less than 15%, less than 20%, less than 25%, less than 30%, less than 35%, or less than 35% to their target or targets. In some examples, one or more affinity reagents may bind moderately or strongly to their target or targets. For example, affinity reagents may bind more than 35%, more than 40%, more than 45%, more than 60%, more than 65%, more than 70%, more than 75%, more than 80%, more than 85%, more than 90%, more than 91%, more than 92%, more than 93%, more than 94%, more than 95%, more than 96%, more than 97%, more than 98%, or more than 99% to their target or targets.

To compensate for weak binding, an excess of the affinity reagent may be applied to the substrate. The affinity reagent may be applied at about a 1:1, 2:1, 3:1, 4:1, 5:1, 6:1, 7:1, 8:1, 9:1 or 10:1 molar excess relative to the sample proteins. The affinity reagent may be applied at about a 1:1, 2:1, 3:1, 4:1, 5:1, 6:1, 7:1, 8:1, 9:1 or 10:1 molar excess relative to the expected incidence of the epitope in the sample proteins.

The affinity reagents may also comprise a magnetic component. The magnetic component may be useful for manipulating some or all bound affinity reagents into the same imaging plane or z stack. Manipulating some or all affinity reagents into the same imaging plane may improve the quality of the imaging data and reduce noise in the system.

Given a set of modified affinity reagents and a conjugated substrate, affinity reagents may be iteratively applied to the substrate. Each measurement cycle consists of several stages. In the first stage, affinity reagents may be applied to the substrate where they may adsorb to the conjugated proteins.

Next, the substrate can be lightly washed to remove non-specific binding. This washing step can be performed under conditions which will not elute affinity reagents which have bound to the immobilized proteins. Some examples of buffers which may be used for this step include phosphate buffered saline, Tris buffered saline, phosphate buffered saline with Tween20, and Tris buffered saline with Tween20.

Following adsorption, the binding addresses for each modified affinity reagent may be determined, such as through measurement of a fluorophore that has been conjugated to the affinity reagents directly, or to a complement nucleic acid to a nucleic acid strand conjugated to the affinity reagents. The detection method may be determined by the choice of detection moiety. Fluorophores and bioluminescent moieties may be optically detected, in some configurations secondary detection reagents may be required. The unique address of each immobilized protein on the substrate may be determined prior to the binding measurements, or a list of addresses containing immobilized proteins may be generated through the binding measurements.

Next, the affinity reagents can be desorbed through a more stringent wash. This wash step may remove some or all affinity reagents from the immobilized substrates. In some configurations, affinity reagents may have been chosen to have low to moderate binding affinities to facilitate removal. Used affinity reagents may be re-captured for reuse or discarded. In examples where affinity reagents with cleavable detection moieties may be used, the detection moieties may be cleaved and removed at this stage. Following stringent washing, in some examples, a remaining fluorescence can be quenched and even more stringent washing applied to remove leftover affinity reagent. Carry-over/contamination can be detected by reimaging the substrate before applying the next affinity reagent. Contamination may also be detected by monitoring consecutive images for recurring signals. This sequence concludes one cycle of analysis.

In some embodiments the fluorescently tagged affinity reagents may be quenched by exposure to prolonged intense light at the activation wavelength. Quenching of the fluorescent tags may replace washing steps to remove the affinity reagents. In some embodiments, it may be desirable to cycle N fluorophores to distinguish which signals were derived from the previous N-1 cycles.

Cycles continue for each affinity reagent or multiplexing thereof. The result of the measurement phase may be a very large table listing the binding coordinates for each affinity reagent, or the affinity reagents which bound at each coordinated location.

Further, if a photo-cleavable linker, or other form of specifically cleavable linker, may be used to attach the proteins to the substrate then specific proteins of interest may be released from the substrate and collected for further study. For example, specific proteins may be identified and eluted for further study. The methods of this disclosure may also serve as a way to purify and/or isolate a protein from a mixture. In some configurations, the method may be able to purify and/or isolate specific isotypes or post translationally modified proteins. In samples for which a complete list of possible proteins and associated sequences may not be available this method may be able to distinguish different proteins of distinguish groups of proteins, these may then be eluted for further study. For example, for highly complex samples containing many unknown proteins, such as gut microbiome samples, the methods described herein may be used to fractionate the sample prior to mass spectrometry. In some configurations, proteins may be eluted from the substrate once their identities can be called. Removing the proteins from the substrate as they are identified allows subsequent rounds of affinity reagent binding to continue for the proteins whose identities cannot yet be called, and may decrease background noise and off target signals for the remaining rounds. In some examples one or more affinity reagents with specificity to particular proteins may be used as a first round to identify high abundance proteins such as serum albumin or immunoglobulins in a blood sample, these high abundance proteins may then be removed early in the process. In some configurations, a subset of the proteins on the substrate may be removed after every round of affinity reagent binding, or after every second, third, fourth, fifth, sixth, seventh, eighth, ninth, tenth, fifteenth, twentieth or more than twentieth round of affinity reagent binding. The signal to noise ratio may increase after each round of protein elution.

In some configurations, unidentified proteins may be grouped or clustered based on their binding patterns. For example, in some configurations, proteins present in the sample may not be represented in the sequence database. Unidentified proteins may be clustered into groups based on their binding patterns to the affinity probes with the goal of each group containing a set of unknown proteins in the sample with the same sequence. Protein quantities may be estimated for each group and included in quantitative analyses including, but not limited to, differential quantification between healthy and disease states, longitudinal analysis, or biomarker discovery. In some configurations, an unidentified group may be selectively removed from the substrate for identification by mass spectrometry. In other configurations, the unidentified group may be identified by performing further binding affinity measurement experiments specifically designed to generate confident identification.

In some configurations, after a protein or set of proteins have been removed it may be possible to add additional sample to the substrate. For example, serum albumin is a high abundance protein in blood serum which may account for about half the protein in a sample, removing serum albumin after a first round of affinity reagent binding may allow the addition of further blood sample to the substrate. In some embodiments, high abundance proteins may be removed prior to immobilizing a sample on a substrate, for example through immunoprecipitation or affinity column purification.

Protein modifications may be identified using the methods of this disclosure. For example, post translational modifications may be identified by iterative cycles of detection using modification specific detection reagents interspersed with enzymatic processing (for example phosphatase treatment). Affinity reagents specific for different modifications may be used to determine the presence of absence of such modifications on the immobilized proteins. The method also allows quantification of the number of instances of each protein with and without a given modification.

Mutations in proteins may be detected by matching inconsistencies between the binding pattern of a sample protein and the predicted protein identity. For example, an immobilized protein or polypeptide on the substrate which matches the affinity reagent binding profile of a known protein except for the binding of one affinity reagent may have an amino acid substitution. As affinity reagents may have overlapping epitopes an immobilized protein may have several mismatches from the predicted affinity binding pattern despite having a single amino acid substitution. DNA mutations which cause frameshifts of premature stop codons may also be detected.

The number of affinity reagents required may be less than the total number of epitopes present in the sample. For example, if the affinity reagents are selected such that each affinity reagent recognizes one unique three peptide epitope then the total set of affinity reagents to recognize all possible epitopes in the sample is 20×20×20=8000. However, the methods of the present disclosure may require about 100, 200, 300, 400, 500, 600, 700, 800, 900, 1000, 1500, 2000, 2500, 3000, 3500, 4000, 4500, 5000, 5500 or 6000 of these affinity reagents. In some configurations, the methods may require less than about 500, 1000, 2500, 3000, 3500, 4000, 4500, 5000, 5500 or 6000 affinity reagents.

The methods of the present disclosure may be highly accurate. The methods of the present disclosure may be able to identify each protein with at least about 90%, 91%, 92%, 93%, 94%, 95%, 96%, 97%, 98%, 98.5%, 99%, 99.5% 99.9% or more than 99.9% accuracy.

The methods of the present disclosure may be able to predict the identity of each protein with at least about 90%, 91%, 92%, 93%, 94%, 95%, 96%, 97%, 98%, 98.5%, 99%, 99.5% 99.9% or more than 99.9% confidence. The degree of confidence may be different for different proteins within the sample. For example, proteins with very unique sequences may be identified with higher confidence than proteins which may be highly similar to other proteins. In some configurations, a protein may be identified as part of a family of proteins with high confidence, however the exact identity of the protein may be predicted with lower confidence. In some configurations, proteins that may be extremely large or extremely small may be predicted with lower confidence than proteins of more moderate size.

In some configurations, a protein may be identified as part of a family of proteins with high confidence, however the exact identity of the protein may be predicted with lower confidence. For example, a protein containing a single amino acid variant may be difficult to resolve from the canonical form of the protein with high confidence. In this configuration, neither the canonical sequence nor the single amino acid variant-containing form may have high confidence, but a high confidence can be assessed to the unknown protein being part of the group of proteins containing both sequences. A similar configuration may occur in instances where a protein may have multiple related isoforms with similar sequence.

The methods of the present disclosure may be able to identify some or all proteins in a given sample. The methods of the present disclosure maybe able to identify at least about 90%, 91%, 92%, 93%, 94%, 95%, 96%, 97%, 98%, 98.5%, 99%, 99.5% 99.9% or more than 99.9% of proteins in a sample.

A protein characterization assay may utilize a fluidic device comprising a substrate that is configured to bind a plurality of polypeptides at individual, optically observable addresses (e.g. a single polypeptide at each address). A substrate in a fluidic device may contain a sufficient number of observable addresses to bind a sufficient number of polypeptides for the characterization to be performed. The number of polypeptides to be characterized in an assay may be based upon the total number of individual molecules in a sample. The number of observable addresses on a substrate may be based upon the expected difference in abundance between the most abundant proteins in a sample and a low copy number protein (e.g., less than about 1000, 500, 250, 100, 50, 25, 10, or less than 10 copies in a sample). For example, if a sample is expected to comprise about 10000000 copies of a high abundance protein relative to a protein that may have about 100 copies, a substrate may comprise at least about $10^6$ binding sites to capture the expected five orders of magnitude difference in abundance between the two proteins. In some configurations, a substrate may comprise binding sites in a range from about $10^9$ to $10^{11}$ individual sites to capture the full difference in abundance of a proteome (e.g., the human proteome). A fluidic device may comprise about 1000, 10000, 100000, 1000000, 10000000, 100000000, 1000000000, 10000000000, 100000000000, 1000000000000, or more than 1000000000000 optically observable addresses that are configured to bind a polypeptide. A fluidic device may comprise at least about 1000, 10000, 100000, 1000000, 10000000, 100000000, 1000000000, 10000000000, 100000000000, 1000000000000, or more than 1000000000000 optically observable addresses that are configured to bind a polypeptide. Alternatively or additionally, an fluidic device may comprise no more than about 1000000000000, 100000000000, 10000000000, 1000000000, 100000000, 10000000, 1000000, 100000, 10000, 1000, or less than 1000 optically observable addresses that are configured to bind a polypeptide.

The methods of the present disclosure may be able to rapidly identify proteins in a sample. The methods of the present disclosure may be able to identify more than about 100, about 1000, about 5000, about 10000, about 20,000, about 30,000, about 40,000, about 50,000, about 100,000, 1,000,000, about 10,000,000, about 100,000,000, about 1,000,000,000, about 10,000,000,000, about 100,000,000, 000, about 1,000,000,000,000 proteins per flowcell per day. The methods of the present disclosure may be able to identify more than about $10^{10}$, $10^{11}$, $10^{12}$, $10^{13}$, $10^{14}$, $10^{15}$, $10^{16}$, $10^{17}$, or more than about $10^{17}$ proteins per flowcell per day. The methods of the present disclosure may be able to identify about $10^{10}$-$10^{12}$, $10^{11}$-$10^{14}$, $10^{12}$-$10^{16}$, or $10^{13}$-$10^{17}$ proteins per flowcell per day. The methods of the present disclosure may be able to identify more than 95% of the proteins within about 10 pg, about 20 pg, about 30 pg, about 40 pg, about 50 pg, about 60 pg, about 70 pg, about 80 pg, about 90 pg, about 100 pg, about 300 pg, about 300 pg, about 400 pg, about 500 pg, about 600 pg, about 700 pg, about 800 pg, about 900 pg, about 1 ng, about 2 ng, about 3 ng, about 4 ng, about 5 ng, about 6 ng, about 7 ng, about 8 ng, about 8 ng, about 10 ng, about 10 ng, about 20 ng, about 30 ng, about 40 ng, about 50 ng, about 60 ng, about 70 ng, about 80 ng, about 90 ng, about 100 ng, about 300 ng, about 300 ng, about 400 ng, about 500 ng, about 600 ng, about 700 ng, about 800 ng, about 900 ng, about 1 μg, about 2 μg, about 3 μg, about 4 μg, about 5 μg, about 6 μg, about 7 μg, about 8 μg, about 8 μg, about 10 μg, about 10 μg, about 20 μg, about 30 μg, about 40 μg, about 50 μg, about 60 μg, about 70 μg, about 80 μg, about 90 μg, about 100 μg, about 300 μg, about 300 μg, about 400 μg, about 500 μg, about 600 μg, about 700 μg, about 800 μg, about 900 μg, or more than about 1 mg of protein per flowcell per day.

The methods of the present disclosure may be used to assess the proteome after an experimental treatment. The methods of the present disclosure may be used to assess the effect of a therapeutic intervention.

The methods of the present disclosure may be used for biomarker discovery. Monitoring proteome expression in subjects with and without disease may identify biomarkers. Monitoring proteome expression in subjects prior to developing diseases, or in subjects at risk of developing diseases may identify biomarkers that predict risk. Evaluating the proteome expression of a subject may indicate the health of the subject or the risk of developing certain diseases or disorders. The methods of this disclosure may be used to evaluate therapies, or differentiate drug/therapy responders from non-responders. The methods of this disclosure may be of particular use for personalized medicine.

The methods of the present disclosure may be used to diagnose disease. Different diseases or disease stages may be associated with different panels of protein expression. Different panels of protein expression may be associated with different treatment outcomes for each given treatment. A subject's proteome expression data may be used to diagnose the subject and/or select the most appropriate therapy.

The methods of the present disclosure may be used to identify the individual or species a sample come from. For example, the methods of the present disclosure may be used to determine if a sample is actually from the claimed species or source. The methods described herein may have an advantage over PCR based methods in samples with abundant protein but limited nucleic acid. For example, identifying the origins of honey samples. For further example the methods of the present disclosure may be used to assess food safety and food quality control.

The methods of the present disclosure may be used to identify a single protein molecule from a pool of protein molecules using less affinity reagents than the number of possible proteins. For example the methods may identify, with certainty above a threshold amount, an unidentified single protein molecule from a pool of N possible proteins, using a panel of affinity reagents, wherein the number of affinity reagents in the panel may be M, and wherein M is less than N. The unidentified protein may be a known protein which corresponds to known protein and gene sequences, or may be an unknown protein without known protein or gene sequences. In the configuration of an unknown protein this method may identify a signature of the unknown protein, and thus the presence and quantity of the unknown protein, but not the amino acid sequence. The methods of the present disclosure may be used to select a panel of M affinity reagents capable of identifying an unidentified protein selected from a pool of n possible proteins. The methods disclosed herein may be also capable of uniquely identifying and quantifying N proteins in a mixture of proteins using M binding reagents, and wherein each protein may be identified via a unique profile of binding by a subset of the M the binding reagents. Further, m may be less than about a half, a third, a fourth, a fifth, a sixth, a seventh, a tenth, a twentieth, a fiftieth or a hundredth of N. For further example the present disclosure may be used to select a panel of less than about 100, 200, 300, 400, 500, 600, 700, 800, 900, 1000, 1500, 2000, 2500, 3000, 3500, or 4000 affinity reagents, such that the panel of affinity reagents may be capable of uniquely identifying each of at least about 100, 500, 1000, 2000, 3000, 4000, 5000, 6000, 7000, 8000, 9000, 10,000, 12,000, 14,000, 16,000, 18,000, 20,000, 25,000, 30,000, 35,000, 40,000, 50,000, 100,000, 200,000, 300,000, 400,000, 500,000, 600,000, 700,000, 800,000, 900,000, 1,000,000, 2,000,000, 3,000,000, 4,000,000, or 5,000,000 different proteins.

The methods of the present disclosure may be capable of identifying most of the proteins in a proteome. The methods of the present disclosure may be capable of identifying most of the proteins in a mammalian, bird, fish, amphibian, reptilian, vertebrate, invertebrate, plant, fungal, bacterial or archaeal proteome. The methods of the present disclosure may be capable of identifying more than about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99% of the proteins in a proteome.

EXAMPLES

Example 1. Substrate Preparation with Surface Functionalizations

A silicon substrate was prepared with a surface functionalization by a chemical vapor deposition method. The silicon substrate was first cleaned via an oxygen plasma method. After oxygen plasma cleaning, the substrate was transferred on to an elevated rack in a vacuum oven. An open glass vial containing 0.5 milliliters of (3-aminopropyl)trimethoxysilane (APTMS) at 20° C. was placed beneath the silicon substrate in the vacuum oven. The oven was heated to 120° C. for 2 hours under vacuum. After the heating cycle, the oven was partially vented and re-evacuated to purge anymaining gaseous APTMS. The purging cycle was repeated twice more before the oven was vented to atmospheric pressure. Ellipsometry and contact angle measurement was performed to confirm the presence of the silanated ligand on the silicon surface.

Example 2. Bonding of Substrates with Surface Functionalizations

A silicon substrate was prepared by the method of Example 1. A second glass substrate with an epoxysilane surface was supplied by Nexterion®. A drop of deionized water was placed on the surface of the aminosilanated silicon substrate, then the epoxysilanated surface of the second glass substrate was brought in to contact with the wetted surface. A pressure was exerted on the interface with a clamp. The slides were covered with an aluminum foil on a hot plate and heated from 20° C. to about 150° C. under a temperature ramp (75, 95, 115 and 150° C. steps) and then baked for 2 hours at 150° C. After heating, the substrates were left on the plate to cool down and then removed and the clamp was removed. Bonding was found to occur in the contact patch where the clamp exerted pressure, creating a bonded interface of about 1.5 mm by 5.5 mm. FIGS. 12A, 12B, 12C, and 12D show the bonded interface 1210 between the bonded substrates immediately after heating (e.g., within a day), and after 4 days, 7 days, 49 days, and 444 days, respectively. The size of the bonded interface 1210 was not found to change 444 days after bonding due to the covalent nature of the bonds formed between surface-bound ligands. FIGS. 15A, 15B, 15C, and 15D show results from a second bonding experiment with a larger contact patch 1510 immediately after heating (e.g., within a day), and after 7 days, 14 days, and 422 days respectively. The size of the contact patch 1510 was not found to change more than 1 year after bonding due to the covalent nature of the bonds formed between surface-bound ligands.

Example 3. Surface Passivation of a Substrate with Phosphates

Figure 11:
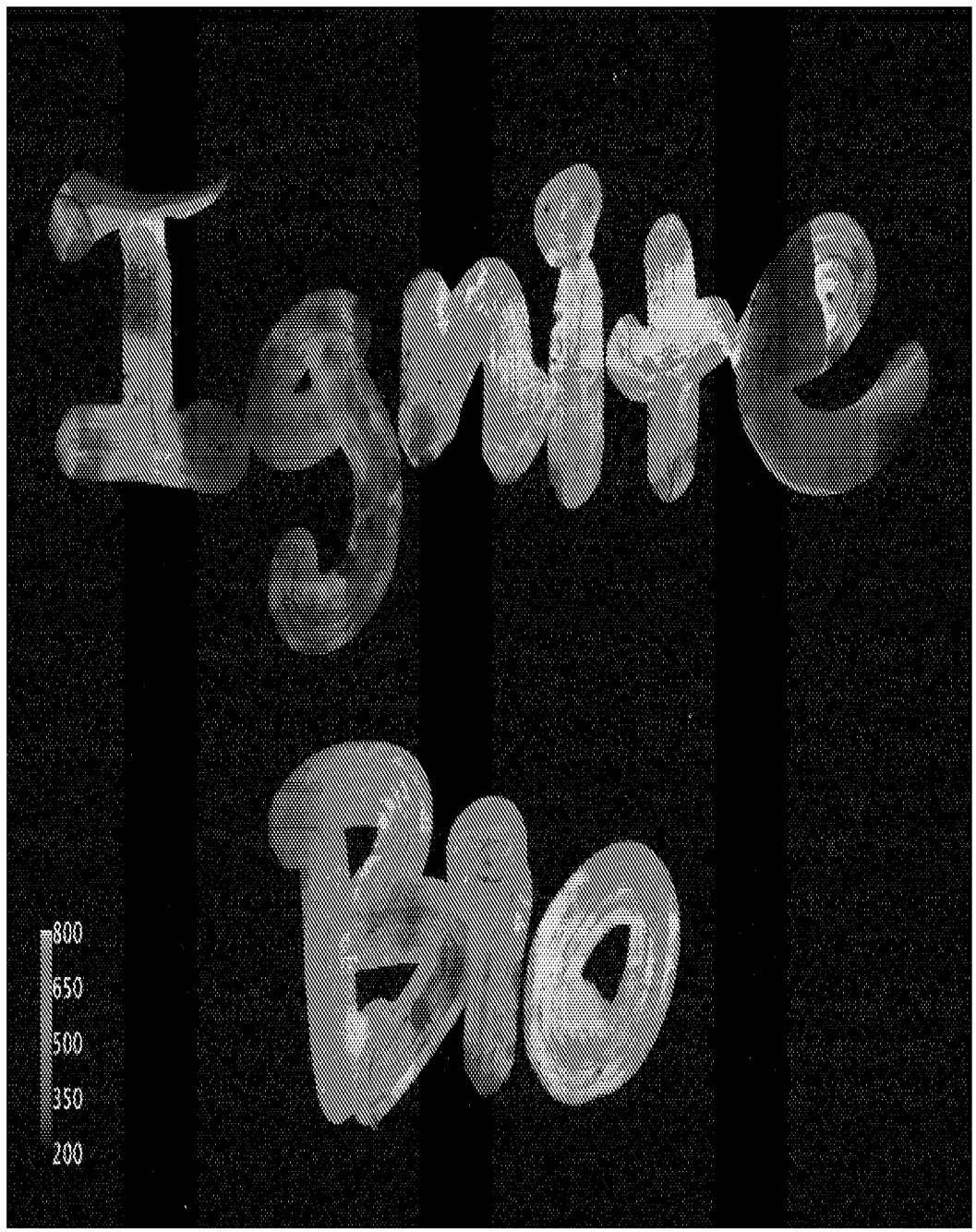
FIG. 11 illustrates a fluorescent image of a silicon substrate selectively passivated to prevent fluorophore binding, in accordance with some embodiments.
Figure 12A:
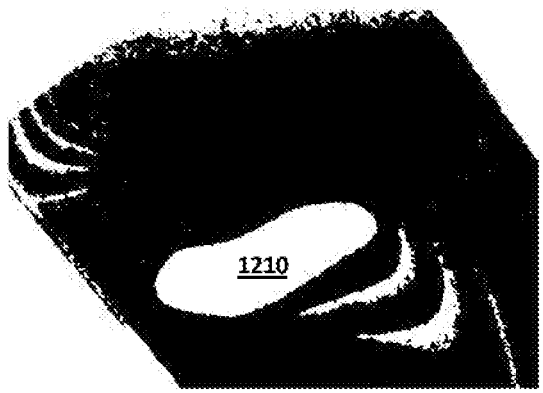
FIG. 12A shows two joined substrates immediately after a bonding process, in accordance with some embodiments.
Figure 12B:
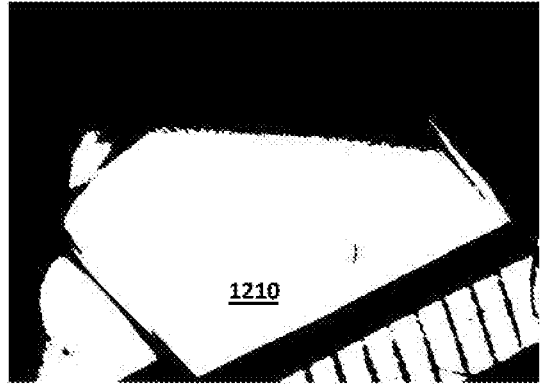
FIG. 12B shows two joined substrates 7 days after a bonding process, in accordance with some embodiments.
Figure 12C:
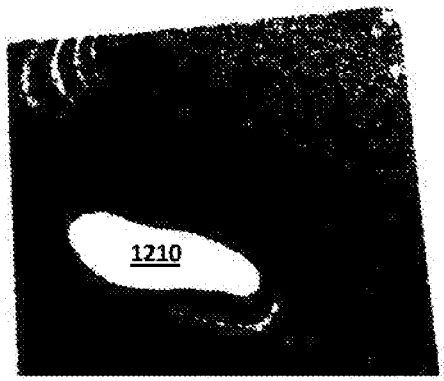
FIG. 12C shows two joined substrates 49 days after a bonding process, in accordance with some embodiments.
Figure 12D:
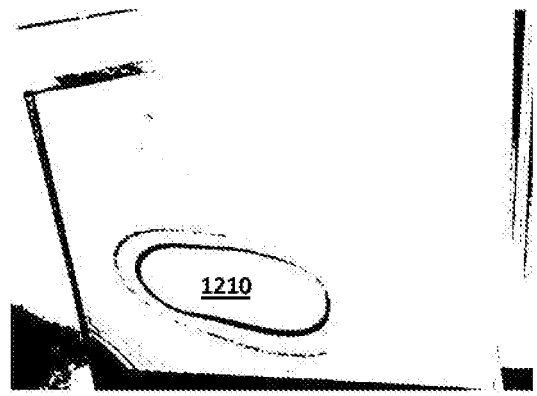
FIG. 12D shows two joined substrates 444 days after a bonding process, in accordance with some embodiments.

A silicon substrate was passivated with phosphate groups. A layer of zirconium oxide was deposited on a glass substrate via atomic layer deposition. The layer was estimated to be 10 to 20 nm thick. The $ZrO_2$-coated surface of the silicon substrate was selectively coated with an ethanol-solvated ink to mask regions of the surface. The ink was dried until all solvent was evaporated. The $ZrO_2$-coated silicon substrate was transferred into a bath of 1× phosphate buffer solution (PBS) at pH 7.4 for 15 minutes. After exposure to PBS, the substrate was rinsed with deionized water and dried completely under $N_2$ gas. The PBS-treated silicon substrate was sonicated in a bath of DMF for 15 seconds to remove the ink on the substrate surface. After ink removal, the silicon substrate was coated with a solution of 1:10000 NHS-647 fluorophore solution. After incubation with the fluorophore, the silicon substrate was removed from the bath, rinsed with deionized water, and dried with $N_2$ gas to remove non-adsorbed fluorophore. FIG. 11 shows a fluorescent image of the silicon substrate after incubation with the fluorophore. The exposure time was 100 milliseconds under 647 nm light. Bright areas indicate the presence of the fluorophore on the substrate surface. The fluorophore was found to selectively adsorb to the regions of the substrate that were not passivated with phosphate ions due to the masking by the ink.

Example 4. Click Bonding of Substrates with Functionalizations

Two substrates are bonded via a cycloaddition click reaction. A glass substrate is provided with a surface functionalized with a silane-PEG-DBCO (dibenzocylooctylene) ligand. A silicon substrate with a 100 nm silicon oxide layer is functionalized with azido (trimethoxy) silane on the silicon oxide layer. The azide-containing surface of the silicon substrate is thinly coated with an aqueous buffer at pH 7. The DBCO-containing surface of the glass substrate is brought into contact with the azide-containing surface in the presence of the aqueous buffer. The surfaces are held in contact by the application of a light pressure for 24 hrs at an ambient temperature that is maintained between 20° C. and 25° C. The click reaction occurs spontaneously between the DBCO and azide moieties. Optionally, the DCBO-containing silane derivative and the azide-containing silane derivative can be replaced with other complementary click reaction pairs (e.g., methyltetrazine-containing silane derivatives and trans-cyclooctene-containing silane derivatives).

After the reaction has occurred, the light pressure is removed from the substrates. The substrates are observed to be joined at the interface where they were contacted. No change in the size or strength of the bond between the interfaces is observed after 1 month.

Figure 22A:
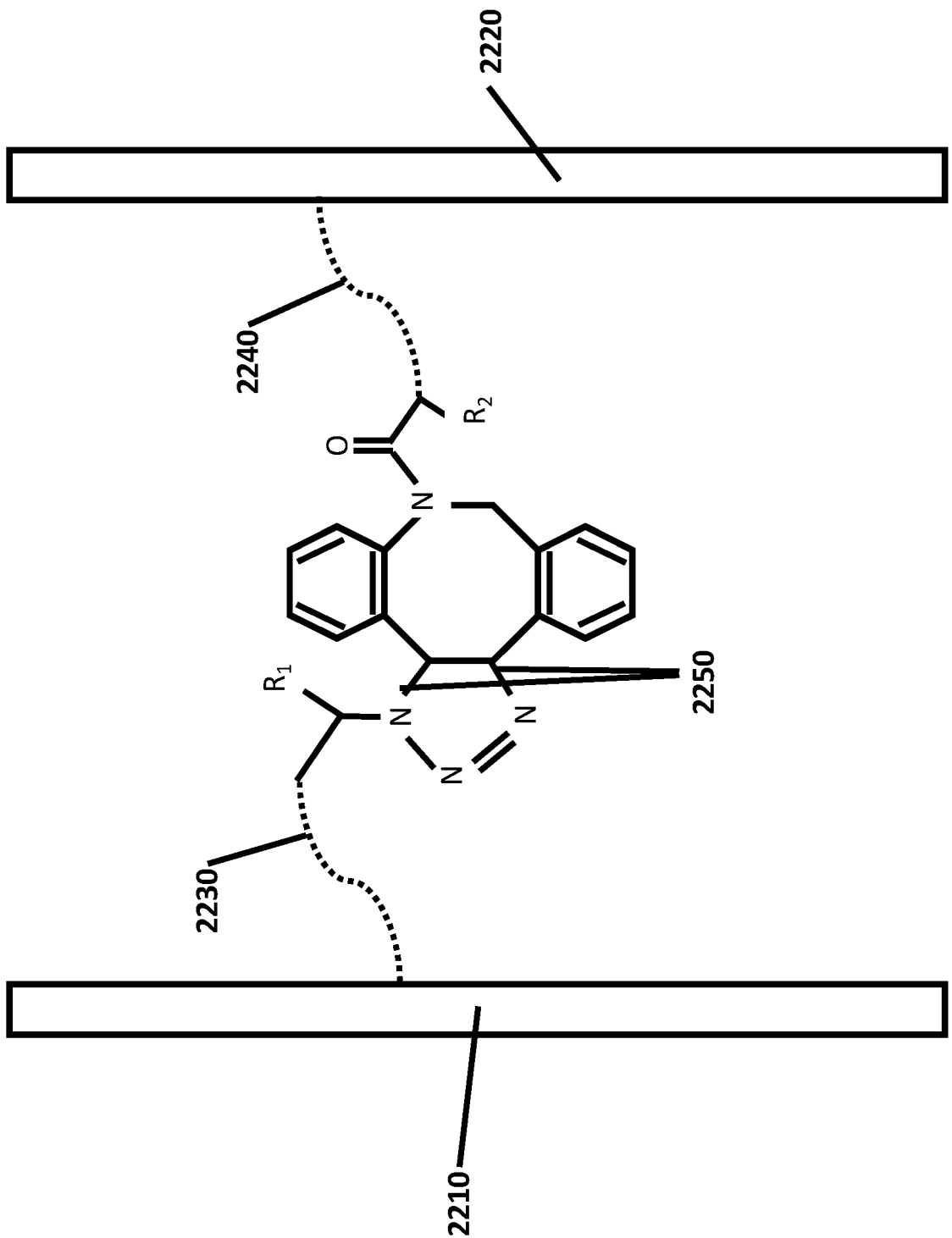
FIG. 22A depicts a cross-sectional schematic of a composition formed between two inorganic substrates by a click reaction between a dibenzocyclooctylene-containing ligand and an azide-containing ligand.
Figure 22B:
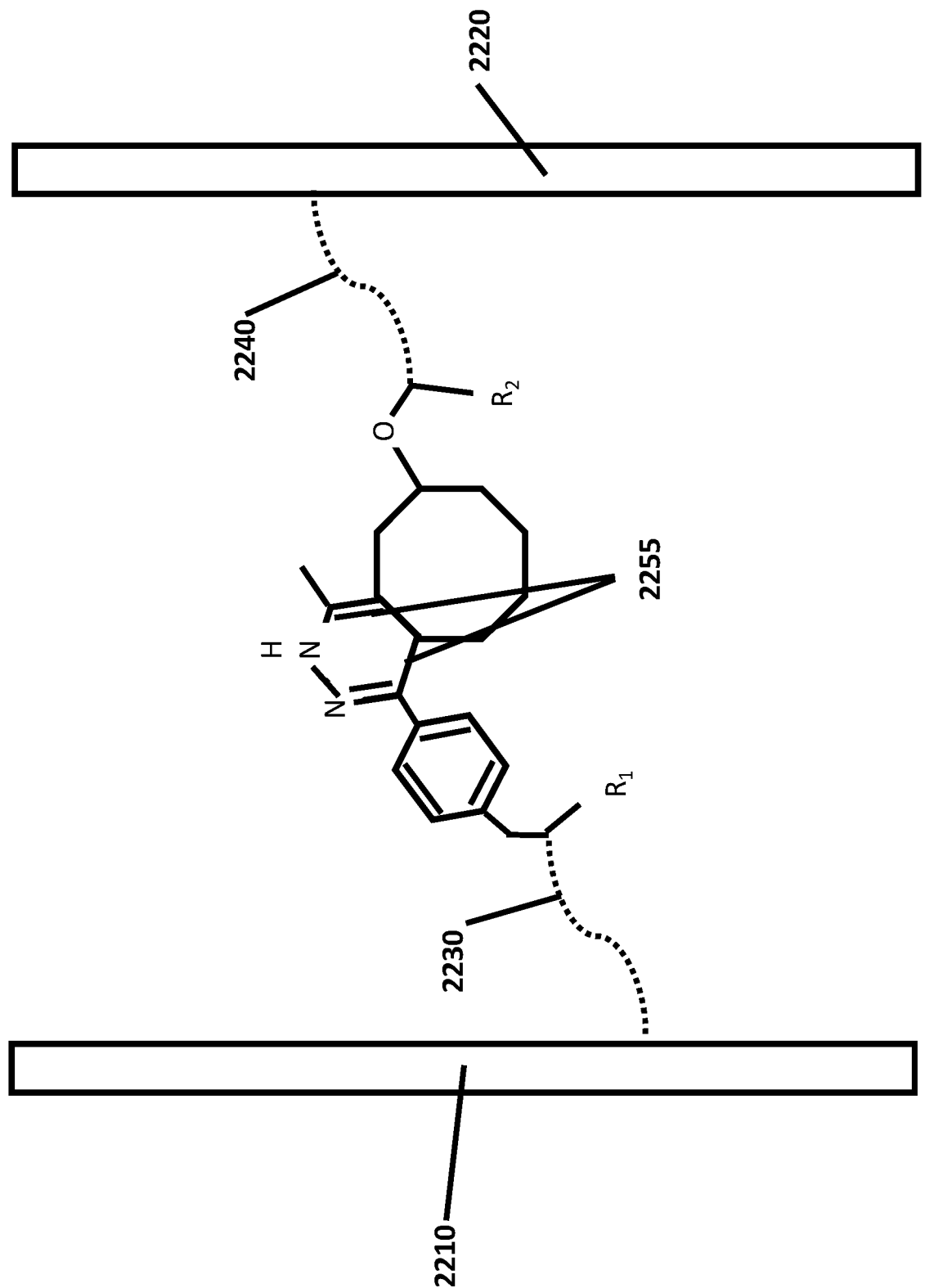
FIG. 22B depicts a cross-sectional schematic of a composition formed between two inorganic substrates by a click reaction between a trans-cyclooctene-containing ligand and a tetrazine-containing ligand.

FIGS. 22A and 22B show exemplary schematics of two inorganic substrates bonded by a click reaction, as is obtained by the above-described methods. FIGS. 22A and 22B show a first organic substrate 2210 containing a first covalently-bound ligand 2230 and, optionally, a linker (e.g., PEG, PEO) and a second organic substrate 2220 containing a second covalently-bound ligand 2240 and, optionally, a linker. The first covalently-bound ligand 2230 and the second covalently-bound ligand 2240 are joined by at least one covalent bond that is formed by the click reaction. FIGS. 22A and 22B show products formed by click reactions that produce heterocyclic compounds, such as dinitrogenous heterocycles (FIG. 22B, bonds 2255) and triazole heterocycles (FIG. 22A, bond 2250). The first covalently-bound ligand 2210 and the second covalently-bound ligand may optionally contain additional functional groups or branched chains, $R_1$ and $R_2$.

While preferred embodiments of the present invention have been shown and described herein, it will be obvious to those skilled in the art that such embodiments are provided by way of example. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered.

Notwithstanding the appended claims, the disclosure set forth herein is also defined by the following clauses:

1. A composition, comprising:
    a first substrate comprising a first covalently-bound ligand, wherein the first covalently-bound ligand comprises a first organic chain and an electrophilic group; and a second substrate comprising a second covalently-bound ligand, wherein the second covalently-bound ligand comprises a second organic chain and a nucleophilic group;
    wherein the electrophilic group is configured to form a bond with the nucleophilic group, and wherein the sum of the length of the first organic chain and the length of the second organic chain is greater than the sum of the average surface roughness of the first substrate and the average surface roughness of the second substrate.
2. The composition of clause 1, wherein the first substrate comprises an inorganic substrate.
3. The composition of clause 2, wherein the inorganic substrate comprises glass, fused silica, or silicon.
4. The composition of clause 2, wherein the inorganic substrate comprises a metal or metal oxide.
5. The composition of clause 1, wherein the second substrate comprises an inorganic substrate.
6. The composition of clause 5, wherein the inorganic substrate comprises glass, fused silica, or silicon.
7. The composition of clause 6, wherein the inorganic substrate comprises a metal or metal oxide.
8. The composition of clause 1, wherein the first covalently-bound ligand comprises an epoxide functional group.
9. The composition of clause 1, wherein the first covalently-bound ligand or the second covalently-bound ligand comprises a silane derivative.
10. The composition of clause 1, wherein the first covalently-bound ligand or the second covalently-bound ligand comprises a phosphate or phosphonate group.
11. The composition of clause 1, wherein the first covalently-bound ligand comprises an acyl halide functional group.
12. The composition of clause 1, wherein the second covalently-bound ligand comprises an amine functional group.
13. The composition of clause 1, wherein the second covalently-bound ligand comprises a thiol functional group.
14. The composition of clause 13, wherein the second-covalently-bound ligand comprises a mercaptosilane.
15. The composition of clause 1, wherein the first covalently-bound ligand or the second covalently-bound ligand comprises a linear organic chain.
16. The composition of clause 1, wherein the first surface roughness or camber is measured by taper-sectioning, profilometry, light-sectioning, specular reflection, diffuse reflection, speckle patterning, optical interferometry, phase shift interferometry, scanning tunneling microscopy, atomic force microscopy, a hydraulic method, pneumatic gauging, a capacitance method, scanning electron microscopy, or electron backscattering.
17. The composition of clause 1, wherein the second surface roughness or camber is measured by taper-sectioning, profilometry, light-sectioning, specular reflection, diffuse reflection, speckle patterning, optical interferometry, phase shift interferometry, scanning tunneling microscopy, atomic force microscopy, a hydraulic method, pneumatic gauging, a capacitance method, scanning electron microscopy, or electron backscattering.
18. The composition of clause 1, wherein the first organic chain comprises at least 5 atoms.
19. The composition of clause 1, wherein the second organic chain comprises at least 5 atoms.
20. The composition of clause 1, wherein the first organic chain is a different length than the second organic chain.
21. The composition of clause 1, wherein the first organic chain or the second organic chain is branched.
22. The composition of clause 1, wherein the first organic chain or the second organic chain is linear.
23. The composition of the clause 1, wherein the first organic chain or the second organic chain comprises a hydrophobic chain.
24. The composition of clause 1, wherein the first organic chain or the second organic chain comprises a hydrophilic chain.
25. A composition, comprising:
    a first substrate comprising a first covalently-bound ligand, wherein the first covalently-bound ligand comprises a first electrophilic group;
    a second substrate comprising a second covalently-bound ligand, wherein the second covalently-bound ligand comprises a first nucleophilic group;
    a cross-linking molecule comprising a second electrophilic group and a second nucleophilic group;

wherein the first and second electrophilic groups are configured to form bonds with the first and second nucleophilic groups.

26. The composition of clause 25, wherein the first substrate comprises an inorganic substrate.

27. The composition of clause 26, wherein the inorganic substrate comprises glass, fused silica, or silicon.

28. The composition of clause 26, wherein the inorganic substrate comprises a metal or metal oxide.

29. The composition of clause 25, wherein the second substrate comprises an inorganic substrate.

30. The composition of clause 29, wherein the inorganic substrate comprises glass, fused silica, or silicon.

31. The composition of clause 29, wherein the inorganic substrate comprises a metal or metal oxide.

32. The composition of clause 25, wherein the first covalently-bound ligand comprises an epoxide functional group.

33. The composition of clause 25, wherein the first covalently-bound ligand or the second covalently-bound ligand comprises a silane derivative.

34. The composition of clause 25, wherein the first covalently-bound ligand or the second covalently-bound ligand comprises a phosphate or phosphonate group.

35. The composition of clause 25, wherein the first covalently-bound ligand comprises an acyl halide functional group.

36. The composition of clause 25, wherein the second covalently-bound ligand comprises an amine functional group.

37. The composition of clause 25, wherein the second covalently-bound ligand comprises a thiol functional group.

38. The composition of clause 37, wherein the second-covalently-bound ligand comprises a mercaptosilane.

39. The composition of clause 25, wherein the first covalently-bound ligand or the second covalently-bound ligand comprises a linear organic chain.

40. The composition of clause 25, wherein the first organic chain comprises at least 5 atoms.

41. The composition of clause 25, wherein the second organic chain comprises at least 5 atoms.

42. The composition of clause 25, wherein the first organic chain is a different length than the second organic chain.

43. The composition of clause 25, wherein the first organic chain or the second organic chain is branched.

44. The composition of clause 25, wherein the first organic chain or the second organic chain is linear.

45. The composition of the clause 25, wherein the first organic chain or the second organic chain comprises a hydrophobic chain.

46. The composition of clause 25, wherein the first organic chain or the second organic chain comprises a hydrophilic chain.

47. The composition of clause 25, wherein the cross-linking molecule comprises an epoxide group.

48. The composition of clause 25, wherein the cross-linking molecule comprises an acyl halide functional group.

49. The composition of clause 25, wherein the cross-linking molecule comprises an amine functional group.

50. The composition of clause 25, wherein the cross-linking molecule comprises a thiol functional group.

51. The composition of clause 25, wherein the cross-linking molecule further comprises an organic chain.

52. The composition of clause 25, wherein the organic chain is branched.

53. The composition of clause 52, wherein the organic chain is linear.

54. The composition of the clause 52, wherein the organic chain comprises a hydrophobic chain.

55. The composition of clause 52, wherein the organic chain comprises a hydrophilic chain.

56. A method of joining a first substrate to a second substrate, comprising:
providing a first substrate comprising a first covalently-bound ligand and a second substrate comprising a second covalently-bound ligand;
contacting the first substrate to the second substrate; and
joining the first substrate to the second substrate by forming a bond between the first covalently-bound ligand and the second covalently-bound ligand;
wherein the first covalently-bound ligand comprises a first organic chain and a electrophilic group, and wherein the second covalently-bound ligand comprises a second organic chain and a nucleophilic group; and
wherein the sum of the length of the first organic chain and the length of the second organic chain is greater than the sum of an average surface roughness of the first substrate and an average surface roughness of the second substrate.

57. The method of clause 56, wherein the first substrate comprises an inorganic substrate.

58. The method of clause 57, wherein the inorganic substrate comprises glass, fused silica, or silicon.

59. The method of clause 57, wherein the inorganic substrate comprises a metal or metal oxide.

60. The method of clause 56, wherein the second substrate comprises an inorganic substrate.

61. The method of clause 60, wherein the inorganic substrate comprises glass, fused silica, or silicon.

62. The method of clause 61, wherein the inorganic substrate comprises a metal or metal oxide.

63. The method of clause 56, wherein the first covalently-bound ligand comprises an epoxide functional group.

64. The method of clause 56, wherein the first covalently-bound ligand or the second covalently-bound ligand comprises a silane derivative.

65. The method of clause 56, wherein the first covalently-bound ligand or the second covalently-bound ligand comprises a phosphate or phosphonate group.

66. The method of clause 56, wherein the first covalently-bound ligand comprises an acyl halide functional group.

67. The method of clause 56, wherein the second covalently-bound ligand comprises an amine functional group.

68. The method of clause 56, wherein the second covalently-bound ligand comprises a thiol functional group.

69. The method of clause 68, wherein the second-covalently-bound ligand comprises a mercaptosilane.

70. The method of clause 56, wherein the first covalently-bound ligand or the second covalently-bound ligand comprises a linear organic chain.

71. The method of clause 56, wherein the first surface roughness or camber is measured by taper-sectioning, profilometry, light-sectioning, specular reflection, diffuse reflection, speckle patterning, optical interferometry, phase shift interferometry, scanning tunneling microscopy, atomic force microscopy, a hydraulic 72. The method of clause 56, wherein the second surface roughness or camber is measured by taper-sectioning, profilometry, light-sectioning, specular reflection, diffuse reflection, speckle patterning, optical interferometry, phase shift interferometry, scanning tunneling microscopy, atomic force microscopy, a hydraulic method, pneumatic gauging, a capacitance method, scanning electron microscopy, or electron backscattering.

73. The method of clause 56, wherein the first organic chain comprises at least 5 atoms.

74. The method of clause 56, wherein the second organic chain comprises at least 5 atoms.

75. The method of clause 56, wherein the first organic chain is a different length than the second organic chain.

76. The composition of clause 56, wherein the first organic chain or the second organic chain is branched.

77. The composition of clause 56, wherein the first organic chain or the second organic chain is linear.

78. The composition of clause 56, wherein the first organic chain or the second organic chain comprises a hydrophobic chain.

79. The composition of clause 56, wherein the first organic chain or the second organic chain comprises a hydrophilic chain.

80. The method of clause 56, wherein the joining occurs at a temperature of no more than about 150° C.

81. The method of clause 56, wherein the joining occurs at a temperature of no more than about 80° C.

82. The method of clause 56, wherein the joining occurs under an exerted pressure.

83. The method of clause 56, wherein the joining occurs under vacuum

84. The method of clause 56, wherein the joining occurs in the presence of a catalyst.

85. The method of clause 56, wherein the joining occurs under acidic or basic conditions.

86. A method of joining a first substrate to a second substrate, comprising:
   providing a first substrate comprising a first covalently-bound ligand and a second substrate comprising a second covalently-bound ligand;
   contacting the first substrate to the second substrate;
   emplacing a cross-linking molecule in a void space between the first substrate and the second substrate; and
   joining the substrate by i) forming a bond between the first covalently-bound ligand and the second covalently-bound ligand, or ii) forming a bond between the cross-linking molecule and both of the first covalently-bound ligand and the second covalently-bound ligand;
wherein the first covalently-bound ligand comprises a first organic chain and a first electrophilic group and the second covalently-bound ligand comprises a second organic chain and a first nucleophilic group; and wherein the cross-linking molecule comprises a second electrophilic group and a second nucleophilic group.

87. The method of clause 85, wherein the first substrate comprises an inorganic substrate.

88. The method of clause 86, wherein the inorganic substrate comprises glass, fused silica, or silicon.

89. The method of clause 86, wherein the inorganic substrate comprises a metal or metal oxide.

90. The method of clause 85, wherein the second substrate comprises an inorganic substrate.

91. The method of clause 89, wherein the inorganic substrate comprises glass, fused silica, or silicon.

92. The method of clause 89, wherein the inorganic substrate comprises a metal or metal oxide.

93. The method of clause 85, wherein the first covalently-bound ligand comprises an epoxide functional group.

94. The method of clause 85, wherein the first covalently-bound ligand or the second covalently-bound ligand comprises a silane derivative.

95. The method of clause 85, wherein the first covalently-bound ligand or the second covalently-bound ligand comprises a phosphate or phosphonate group.

96. The method of clause 85, wherein the first covalently-bound ligand comprises an acyl halide functional group.

97. The method of clause 85, wherein the second covalently-bound ligand comprises an amine functional group.

98. The method of clause 85, wherein the second covalently-bound ligand comprises a thiol functional group.

99. The method of clause 87, wherein the second-covalently-bound ligand comprises a mercaptosilane.

100. The method of clause 85, wherein the first covalently-bound ligand or the second covalently-bound ligand comprises a linear organic chain.

101. The method of clause 85, wherein the first organic chain comprises at least 5 atoms.

102. The method of clause 85, wherein the second organic chain comprises at least 5 atoms.

103. The method of clause 85, wherein the first organic chain is a different length than the second organic chain.

104. The method of clause 85, wherein the first organic chain or the second organic chain is branched.

105. The method of clause 85, wherein the first organic chain or the second organic chain is linear.

106. The method of the clause 85, wherein the first organic chain or the second organic chain comprises a hydrophobic chain.

107. The method of clause 85, wherein the first organic chain or the second organic chain comprises a hydrophilic chain.

108. The method of clause 85, wherein the cross-linking molecule comprises an epoxide group.

109. The method of clause 85, wherein the cross-linking molecule comprises an acyl halide functional group.

110. The method of clause 85, wherein the cross-linking molecule comprises an amine functional group.

111. The method of clause 85, wherein the cross-linking molecule comprises a thiol functional group.

112. The method of clause 85, wherein the cross-linking molecule further comprises an organic chain.

113. The method of clause 111, wherein the organic chain is branched.

114. The method of clause 111, wherein the organic chain is linear.

115. The method of clause 111, wherein the organic chain comprises a hydrophobic chain.

116. The method of clause 111, wherein the organic chain comprises a hydrophilic chain.

117. The method of clause 85, wherein the joining occurs at a temperature of no more than about 150° C.

118. The method of clause 85, wherein the joining occurs at a temperature of no more than about 80° C.
119. The method of clause 85, wherein the joining occurs under an exerted pressure.
120. The method of clause 85, wherein the joining occurs under vacuum.
121. The method of clause 85, wherein the joining occurs in the presence of a catalyst.
122. The method of clause 85, wherein the joining occurs under acidic or basic conditions.
123. A flow cell device, comprising:
a first substrate comprising a microfabricated surface; and
a second substrate comprising a non-patterned surface;
wherein the first substrate is joined to the second substrate to form an enclosure; and
wherein the microfabricated surface comprises at least one chamber, wherein the chamber comprises a microarray of active sites with specific functionalization separated by a resolvable distance and a functionalized surface comprising a passivating group or a blocking group;
and wherein each active site of the microarray of active sites comprises a capture agent.
124. A method of fabricating a flow cell device, comprising:
providing a first substrate comprising a microfabricated surface, wherein the microfabricated surface comprises a first surface and a second surface;
providing a second substrate comprising a non-patterned surface;
joining the first substrate to the second substrate;
linking a capture agent to the first surface; and
linking a blocking group or passivating group to the second surface;
wherein the first surface comprises a microarray of active sites with a specific functionalization separated by an optically resolvable distance.

What is claimed is:
1. A method, comprising:
a) contacting a first inorganic substrate to a second inorganic substrate, wherein the first inorganic substrate comprises a first covalently-bound ligand, and wherein the second inorganic substrate comprises a second covalently-bound ligand, wherein the first covalently-bound ligand or the second covalently-bound ligand comprises a branched chain, a hydrophobic chain, or a hydrophilic chain; and
b) joining the first inorganic substrate to the second inorganic substrate by forming a bond between the first covalently-bound ligand and the second covalently-bound ligand;
wherein the first covalently-bound ligand comprises a first functional group and the second covalently-bound ligand comprises a second functional group, and wherein the first functional group and the second functional group react via a bioorthogonal reaction or a click reaction to form the bond between the first covalently-bound ligand and the second covalently-bound ligand.
2. The method of claim 1, wherein the first covalently-bound ligand or the second covalently-bound ligand comprises a silane derivative.
3. The method of claim 1, wherein the first covalently-bound ligand or the second covalently-bound ligand comprises a phosphate or phosphonate group.
4. The method of claim 1, wherein the first functional group is selected from the group consisting of alkenes, alkynes, azides, epoxides, amines, thiols, nitrones, isonitriles, isocyanides, aziridines, activated esters, and tetrazines.
5. The method of claim 4, wherein the second functional group is selected from the group consisting of alkenes, alkynes, azides, epoxides, amines, thiols, nitrones, isonitriles, isocyanides, aziridines, activated esters, and tetrazines.
6. The method of claim 1, wherein the click reaction is selected from the group consisting of metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norborene cycloaddition, oxanobornadiene cycloaddition, tetrazine ligation, and tetrazole photoclick reaction.
7. The method of claim 6, wherein the click reaction is selected from the group consisting of reacting a dibenzocyclooctyne (DBCO) functional group with an azide functional group, reacting a methyltetrazine (mTz) functional group with a transcyclooctylene (TCO) functional group, and reacting an epoxide functional group with a thiol functional group.
8. The method of claim 7, wherein the first covalently-bound ligand comprises a silane derivative comprising the first functional group, wherein the first functional group is selected from the group consisting of DBCO, azide, mTz, N-hydroxysuccinimide (NHS) ester, TCO, epoxide, and thiol.
9. The method of claim 8, wherein the second covalently-bound ligand comprises a silane derivative comprising the second functional group, wherein the second functional group is selected from the group consisting of DBCO, azide, mTz, NHS ester, TCO, epoxide, and thiol.
10. The method of claim 1, wherein the click reaction occurs in presence of an aqueous fluid medium.
11. The method of claim 1, wherein the first covalently-bound ligand or the second covalently-bound ligand comprises a linear organic chain comprising at least 5 atoms.
12. The method of claim 1, wherein the first covalently-bound ligand comprises a first linear organic chain, wherein the second covalently-bound ligand comprises a second linear organic chain, and wherein the first linear organic chain has a different length than the second linear organic chain.
13. The method of claim 1, wherein the joining occurs at a temperature of no more than about 30° C.
14. The method of claim 1, wherein the joining occurs under an exerted pressure.
15. The method of claim 1, wherein the joining occurs under vacuum.
16. The method of claim 1, wherein the joining occurs in presence of a catalyst.

* * * * *